US00RE43569E

(19) United States
(12) Reissued Patent
Olson

(10) Patent Number: US RE43,569 E
(45) Date of Reissued Patent: Aug. 7, 2012

(54) THREE DIMENSIONAL VECTOR CARDIOGRAPH AND METHOD FOR DETECTING AND MONITORING ISCHEMIC EVENTS

(75) Inventor: Charles W. Olson, Huntington Station, NY (US)

(73) Assignee: ECG-Tech Corp., Huntington Station, NY (US)

(21) Appl. No.: 11/796,152

(22) Filed: Apr. 26, 2007

Related U.S. Patent Documents

Reissue of:
(64) Patent No.: 6,884,218
Issued: Apr. 26, 2005
Appl. No.: 10/419,427
Filed: Apr. 21, 2003

U.S. Applications:
(60) Provisional application No. 60/431,862, filed on Dec. 9, 2002.

(51) Int. Cl.
*A61B 8/06* (2006.01)
*A61B 5/0402* (2006.01)
*A61B 5/044* (2006.01)
*A61B 5/0452* (2006.01)

(52) U.S. Cl. ..... 600/450; 600/512; 600/516; 600/517

(58) Field of Classification Search ..... 600/509, 600/512, 516, 517, 450
See application file for complete search history.

(56) References Cited

U.S. PATENT DOCUMENTS 3,186,403 A 6/1965 Bassett
3,333,580 A 8/1967 Fawcett
3,710,174 A 1/1973 Cerniglia, Jr.
(Continued)

FOREIGN PATENT DOCUMENTS

EP 0 383 697 8/1990
(Continued)

OTHER PUBLICATIONS

PCT/US98/18557 International Search Report (Last three pages).
(Continued)

*Primary Examiner* — Tammie K Heller
(74) *Attorney, Agent, or Firm* — John F. Vodopia PC

(57) ABSTRACT

A method of determining an ischemic event includes the steps of: monitoring and storing an initial electrocardiogram vector signal (x, y, z) of a known non-ischemic condition over the QRS, ST and T wave intervals; calculating and storing a J-point of the vector signal and a maximum magnitude of a signal level over the T wave interval; monitoring a subsequent electrocardiogram vector signal over the QRS, ST and T wave intervals; measuring and storing the magnitude (Mag.) of the vector difference between a subsequent vector signal and the initial vector signal; measuring and storing the angle (Ang.) difference between a subsequent vector and the initial vector at points; regressing a line from points about 25 milliseconds prior to the J point and about 60 milliseconds after the J-point and determining the slope of the regression line and the deviation of the angle difference of the regression line; regressing a line from points about 100 milliseconds prior to the maximum magnitude of the signal level over the T wave interval and determining the slope of the regressing line and the deviation of the angle difference of the regression line; and comparing the slope and deviation of the lines from the J point and the T wave interval to a set of known values to determine the presence of an ischemic event.

20 Claims, 36 Drawing Sheets
(3 of 36 Drawing Sheet(s) Filed in Color)

U.S. PATENT DOCUMENTS

| | | | | | |
|---|---|---|---|---|---|
| 3,816,849 | A | | 6/1974 | Kinoshita et al. | |
| 4,136,690 | A | | 1/1979 | Anderson et al. | |
| 4,175,337 | A | | 11/1979 | Benjo | |
| 4,292,977 | A | | 10/1981 | Krause et al. | |
| 4,478,223 | A | | 10/1984 | Allor | |
| 4,528,988 | A | | 7/1985 | Wong | |
| 4,537,202 | A | | 8/1985 | Mancini et al. | |
| 4,587,976 | A | | 5/1986 | Schmid et al. | |
| 4,697,597 | A | | 10/1987 | Sanz et al. | |
| 4,700,712 | A | | 10/1987 | Schmid | |
| 4,850,370 | A | | 7/1989 | Dower | |
| 4,898,181 | A | | 2/1990 | Kessler | |
| 4,922,920 | A | | 5/1990 | Thie et al. | |
| 4,949,725 | A | | 8/1990 | Raviv et al. | |
| 5,046,504 | A | | 9/1991 | Albert et al. | |
| 5,101,833 | A | | 4/1992 | Schmid | |
| 5,117,833 | A | * | 6/1992 | Albert et al. | 600/515 |
| 5,227,307 | A | * | 7/1993 | Bar-Or et al. | 436/63 |
| 5,284,152 | A | | 2/1994 | Portnuff et al. | |
| 5,458,116 | A | | 10/1995 | Egler | |
| 5,544,656 | A | * | 8/1996 | Pitsillides et al. | 600/450 |
| 5,713,367 | A | * | 2/1998 | Arnold et al. | 600/517 |
| 5,782,773 | A | | 7/1998 | Kuo et al. | |
| 5,803,084 | A | | 9/1998 | Olson | |
| 6,039,690 | A | * | 3/2000 | Holley et al. | 600/440 |
| 6,132,373 | A | * | 10/2000 | Ito et al. | 600/437 |
| 6,339,720 | B1 | * | 1/2002 | Anzellini et al. | 600/517 |

FOREIGN PATENT DOCUMENTS

| | | | |
|---|---|---|---|
| EP | 0 383 697 | A2 | 8/1990 |
| EP | 0 674 873 | | 10/1995 |
| EP | 0 674 873 | B1 | 10/1995 |

OTHER PUBLICATIONS

PCT/US98/18557 International Search Report.

* cited by examiner

Prior Art

Note: The vector offset due to the ischemia is constant over the entire period from prior to the J-point to the end of the T-wave. (T-wave in blue, J-point vector in red, and the purple vectors are just prior to the J-point.)

Flow Chart for J-Point

Flow Chart for Estimating ST Parameters

THREE DIMENSIONAL VECTOR CARDIOGRAPH AND METHOD FOR DETECTING AND MONITORING ISCHEMIC EVENTS

Matter enclosed in heavy brackets [ ] appears in the original patent but forms no part of this reissue specification; matter printed in italics indicates the additions made by reissue.

CROSS REFERENCE TO RELATED APPLICATION

The present application claims the benefits of and priority to U.S. Provisional Patent Application Ser. No. 60/431,862 filed on Dec. 9, 2002, the entire contents of which are incorporated herein by reference.

BACKGROUND

The present disclosure relates to a method for detecting and monitoring electrical signals from the heart for analysis of heart malfunctions. More particularly, the presently disclosed method relates to a technique for distinguishing between ischemic electrocardiograph (ECG) events and patient positional changes during patient monitoring.

Multi-lead ECGs for diagnosing various heart maladies have been used for many years. The most prevalent technique for analyzing and diagnosing heart conditions involves a 12-lead system. The 12-Lead system provides much redundant information in the frontal plane (X, Y) and transverse plane (X, Z) of the ECG vector signal. It permits only a rough visual estimate of the vector direction in theses two planes. Other techniques such as two-dimensional (2-D) vector cardiograms have proven in the past to be quite expensive and cumbersome due to the relative cost and size of the equipment needed to properly display the vector cardiograms, e.g., one cathode ray tube (CRT) oscilloscope was needed for the display of each bodily plane. Further, analysis of the 2-D vector cardiograms typically required a high degree of technical skill and mental agility in interrelating the three displays to formulate a good picture of the 3-D vector. Rules were established on the basis of individual 2-D diagrams and the 3-D vector effect was lost. As a result, the 12-Lead system has become prevalent and widely accepted.

However, in order to teach the 12-lead system, it has always been important for doctors to have a rudimentary knowledge of the relation of the ECG signal to the electrical activity of the heart. This relation is briefly summarized below.

The heart pulse is initiated by the Sino-artial (S-A) node which is generally located in the right atrium and, in a normal heart, acts as the heart's chief pacemaker. The stimulation or depolarization of the entire atria takes place after the occurrence of the S-A node pulse. A graphical representation of the initial depolarization of the atria on the electrocardiogram is represented by a positive deflection on the ECG and is commonly called the P-wave (See FIG. 12).

After an initial electrical pulse from the S-A node, depolarization of the heart muscle spreads to the atrioventicular (A-V) node and is then conducted to the "Bundle of His" (during which time it is slowed down to allow for the atria to pump blood into the ventricles) and thereafter to the "Bundle Branches". This is known as the PR Segment. The P-R Interval represents the time of transmission of the electrical signal from the initial S-A node impulse to the ventricles.

Ventricle depolarization is known on an ECG by the QRS complex which relates to the contraction or depolarization of the heart muscles, in particular, the right ventricle and left ventricle. This is the most studied cycle and is considered to be the most important for the prediction of health and survivability of a patient. It is initiated by the signal from the Bundle of His and then the high speed Purkinje muscle fibers rapidly excite the endocardium of the left ventricle and then the right ventricle. Early experimental work showed the timing of this excitation and the progress of the electrical wave through the right and left ventricles of the heart, however, it was very difficult to determine the net vector effect of this 3-D wave and its relationship to the overall movement of the cardiac muscle. As a result, most textbooks and physicians have adopted a simplified two-dimensional approach to analyzing this problem.

On the graph shown in FIG. 12, ventricular depolarization is clearly discernible. The most easily recognizable deflection (positive deflection—upward movement above the base line on the ECG) of the QRS complex is termed the R-wave. Just prior to this deflection is the Q-wave which is typically represented by an inverted signal deflection (negative deflection—downward movement below the base line on the ECG). The negative deflection after the R-wave is termed the S-wave which is the terminal part of the QRS complex. (See FIG. 12).

Repolarization occurs after the termination of the S-wave and starts with another positive deflection know as the T-wave. The time frame for the initiation of repolarization is termed the S-T segment and is usually represented by an isoelectric signal, i.e., neither positive or negative deflection. This S-T segment is a most important indicator of the health of the ventricular myocardium.

In order to show these electrical signals as they activate and stimulate the heart muscle, a system had to be developed to record the signals as they transverse the cardiac muscle. Einthoven found that by placing electrodes at various positions on the body and completing the circuit between the heart muscle and the electrocardiogram, it was possible to view the electrical activity between two electrodes of the heart. Each view derived from the varying placement of the electrodes was known as a "Lead". For most purposes, a typical ECG screening involves using a 12-Lead system in which the leads are arranged at various points of the body, e.g., outer extremities, and the signals are recorded across each "Lead". A physician is trained to analyze and interpret the output from these Leads and make a diagnosis. In order to help a physician make an accurate diagnosis, various formulas and methods have been developed which translate the output of the 12-Lead system into workable solutions, e.g., Einthoven's Law and 2-D Vector Cardiography.

In order to better explain the novel aspects and unique benefits of the present invention, a brief explanation of vector cardiographic analysis and the numerous steps and processes a physician typically undergoes in order to offer a somewhat accurate diagnosis is relevant.

Vector Cardiography uses a vector description of the progress of the signal through the heart during a QRS interval. This vector representation forms the basis upon which a doctor is trained to understand and explain the outputs received at the various electrodes in the 12-Lead system. Typically within a period of about 0.08 seconds (one normal QRS interval), both ventricles are depolarized and, as a result an electrical force is generated which is characterized by a vector which depicts both the size and direction of the electrical force. In electrocardiography, these vectors are created sequentially over the entire QRS interval. The normal plane for these vectors (i.e., the normal plane of activation) is the same as the QRS cycle, i.e., perpendicular to the X, Y plane (frontal) and slanted along the axis of the heart.

In actuality, the muscle depolarizes from cell to cell and forms an electrical wave front (a plane which separates tissue of different electrical potential) as a function of time. This wave front can be used to determine the resultant or mean vector whose magnitude, direction and location can be determined by the summation of all the small vectors which can be drawn perpendicular to the wave front. The resultant or mean vector of all these vectors is the resultant vector which is measured by the external electrodes and is called the QRS vector. As can be appreciated, other mean vectors are created over the other intervals in the ECG cycle in much the same manner are termed appropriately, namely, the mean T-vector and the mean P-vector.

Traditionally, it has been found that the force and direction of the QRS vector would give an accurate representation of how the heart was functioning over the period of the QRS interval. In order to help determine the QRS vector in the frontal plane, a law was developed by Einthoven which interrelated three (3) electrodes specifically oriented on the body (right arm, left leg and left arm). The signals between each two of the electrodes constituted a "Lead". These leads formed a triangle known as Einthoven's triangle and it was that these Leads could always be related to a single vector in the frontal plane, i.e., any two signals when added vectorally give a third vector. For diagnostic purposes these Leads were later graphically translated into a triaxial system. Other Leads were subsequently added to the triaxial system (i.e., termed unipolar leads—a VR, a VL, and a VF) and a Hexial system was developed. For simplification purposes, the system was displayed out on a circle and degrees were later assigned to the various leads of the system. FIG. 1a shows the circle which was developed to represent the six Leads. This system is highly redundant.

In order for a physician to determine the mean QRS vector, the physician would line up the various leads around the circle according to their positivity or negativity and mark the transition from positive to negative on the circle. This area of transition is typically referred to as the "transition" area which when analyzing a single plane, e.g., the frontal plane, is represented by a line on the circle which separates the circle into positive and negative halves. (See FIG. 1b). The mean QRS vector is positioned at a right angle to the transition line on the positive side. (See FIG. 1b).

Using the above methodology, the direction and location of the mean QRS vector on the circle determines how the heart is functioning and allows a physician to ascertain typical heart malfunctions. For example, in a normal adult, the mean QRS vector is usually located between 0° and 90°, i.e., between leads I and a VF on the circle. However, a left axis deviation (LAD) is characterized by the mean QRS vector being located in the 0° to −90° area and with right axis deviation (RAD) the mean QRS vector is located in the 90° to 180° area.

The mean T-vector and the mean P-vector are determined in a similar manner. In fact, physicians have determined that one of the more important elements of graphically illustrating the means QRS vector and the mean T-vector is that the angle between the two vectors can be easily ascertained. This angle relates the forces of ventricular depolarization with the forces of ventricle repolarization. In a normal adult, the angle between the mean QRS vector and the mean T-vector is rarely greater than 60° and most often below 45°.

Similarly, the mean P-vector can be determined. This enables a physician to isolate the location of the electrical direction of the excitation of the cardiac muscle of the atria.

The above analysis has been described using a single plane, namely the frontal plane characterized by the superior, inferior, right and left boundaries of the human body. In order for a physician to analyze the overall movement of the heart muscle during depolarization and repolarization, the physician needs to analyze the vector forces along another plane, namely the horizontal plane which is characterized by the posterior, anterior, right and left boundaries of the human body.

Much in the same manner as described above, six leads are positioned about the body to measure the electrical currents across the heart muscle in the horizontal plane. These leads are typically called the precordial leads and are represented as V1-V6, respectively. Using the same methodology as described above with respect to the frontal plane, the location and direction of the mean QRS vector in the horizontal plane can also be determined.

When the two planes are analyzed simultaneously, the mean QRS vector (and the other vectors) projects perpendicularly from the transition "plane" rather than the transition "line" of the single plane system. In other words, when the frontal plane and the horizontal plane are isolated and individually analyzed, the mean QRS transition appears as a line across the diameter of the circle. In actuality this "line" is actually a "plane" when both systems (frontal and horizontal) are analyzed simultaneously and the mean vectors (QRS, T and P) project perpendicularly from this plane into both systems.

As can be appreciated from the above summary, the analytical process of determining the resultant QRS vector and the other vectors can be quite cumbersome and requires a physician to interpret various graphs and/or solve various formulas which tend only to frustrate the diagnostic process and which can lead to erroneous conclusions if analyzed improperly. For simplicity, most physicians analyze each system individually at first and then combine the results. However, as often is the case, the determination of the mean vectors (QRS, T and P) in one plane is still both time consuming and somewhat confusing. Further, trying to determine how the mean vectors project into two planes and how the angles between the vectors relate can be even more confusing.

Moreover, even if a physician can adequately analyze the various graphs and solve the various formulas to arrive at a diagnosis, three-dimensional representation of the location of the mean QRS vectors (and the other vectors) must be mentally visualized which requires a high degree of mental agility and can lead to misdiagnosis. Further, mentally visualizing the angles between mean vectors would be virtually impossible for even the most skilled physician. The additional problem of how these vectors change in time over the QRS interval is believed to be nearly impossible to consider by the prior methods.

In the past, several attempts have been made at resolving the above problems. For example, 2-D vector cardiograms isolated the various signals from the leads and used several oscilloscopes to show the results in three planes (frontal, transverse (horizontal) and sagittal). This has been studied in great detail and many texts have been written to relate these diagrams to various heart maladies. However, as far as is known no one has ever attempted to display the signal as a series of 3-D vectors plotted at intermittent time intervals over the duration of the signal, much less represent these vectors on a single display and on a single 3-D coordinate system thereby producing a more easily identifiable 3-D view of the 12-Lead ECG signal or QRS complex as it progresses through the cardiac muscle over time.

As can be appreciated, the above issues are exacerbated during continual heart monitoring, e.g., monitoring patients in the telemetry unit of a hospital. For example and as mentioned above, continual heart monitoring utilizing a standard 12-lead display system is a demanding process. As a result, heart monitoring is usually automated such that slight changes in the electrical signal from the heart are typically registered. A set of conditions are programmed into the heart monitor and upon reaching a predetermined threshold a bell or buzzer alerts the hospital staff. As is often the case, false signals are generated which, as can be appreciated, can be a tremendous waste of hospital resources. For example, simple positional changes (i.e., a patient turns over to lie on his/her side) often trips the heart monitoring alarm to alert the staff of an ischemic condition. As can be appreciated, this can be stressful on the hospital staff.

It would therefore be desirable to provide a device which can overcome many of the aforesaid difficulties with diagnosing, analyzing and monitoring heart malfunctions and provide devices and methods which display heart maladies in an easily recognizable, distinguishable, consistent and effective manner allowing even an untrained observer to easily visualize, isolate and analyze common heart conditions.

SUMMARY OF THE INVENTION

Accordingly, it is an object of the present invention to provide a novel device and method which uses a vector description of the progress of the signal through the heart during the QRS interval which forms the basis upon which the doctor is trained to understand the outputs received at the various electrodes in the 12-Lead system. The present disclosure relates to a of determining an ischemic event and includes the steps of: monitoring and storing an initial electrocardiogram vector signal (x, y, z) of a known non-ischemic condition over the QRS, ST and T wave intervals; calculating and storing a J-point of the vector signal and a maximum magnitude of a signal level over the T wave interval; monitoring a subsequent electrocardiogram vector signal over the QRS, ST and T wave intervals; measuring and storing the magnitude (Mag.) of the vector difference between a subsequent vector signal and the initial vector signal; measuring and storing the angle (Ang.) difference between a subsequent vector and the initial vector at points; regressing a line from points about 25 milliseconds prior to the J point and about 60 milliseconds after the J-point and determining the slope of the regression line and the deviation of the angle difference of the regression line; regressing a line from points about 100 milliseconds prior to the maximum magnitude of the signal level over the T wave interval and determining the slope of the regressing line and the deviation of the angle difference of the regression line; and comparing the slope and deviation of the lines from the J point and the T wave interval to a set of known values to determine the presence of an ischemic event.

In one embodiment, the step of measuring and storing the magnitude (Mag.) of the vector difference includes the steps of: accessing the stored initial electrocardiogram vector signal (x, y, z) of a known non-ischemic condition over the QRS, ST and T wave intervals; measuring the subsequent electrocardiogram vector signal (x, y, z) over the QRS, ST and T wave intervals; calculating the change (Δ) in the vector signal over the QRS, ST and T wave intervals by the following formula:

$$\Delta x = x2 - x1$$

$$\Delta y = y2 - y1$$

$$\Delta z = z2 - z1; \text{ and}$$

calculating the magnitude of the vector difference ($Mag_{vd}$) over the QRS, ST and T wave intervals by the following formula:

$$Mag_{vd} = \sqrt{(\Delta x^2 + \Delta y^2 + \Delta z^2)}$$

In another embodiment, the step of measuring and storing the angle of the vector difference (Ang.) includes the steps of: accessing the stored initial electrocardiogram vector signal (x, y, z) of a known non-ischemic condition over the QRS, ST and T wave intervals; measuring the subsequent electrocardiogram vector signal (x, y, z) over the QRS, ST and T wave intervals; calculating the change (Δ) in the vector signal over the QRS, ST and T wave intervals by the following formula:

$$\Delta x = x2 - x1$$

$$\Delta y = y2 - x1$$

$$\Delta z = z2 - x1;$$

calculating an azimuth angle (Az. Ang.) of the angle vector difference over the QRS, ST and T wave intervals by the following formula:

$$\text{Az. Ang.} = \text{arc tan}(\Delta z/\Delta x); \text{ and}$$

calculating an elevation angle (El. Ang.) of the angle vector difference over the QRS, ST and T wave intervals by the following formula:

$$\text{El. Ang.} = \text{arc tan}(\Delta y/\sqrt{(\Delta x^2 + \Delta z^2)}).$$

In still yet another embodiment according to the present method, the step of calculating the J point includes the steps of: calculating the magnitude of the initial vector signal ($Mag_{vs}$) over the QRS, ST and T wave intervals by the following formula:

$$Mag_{vs} = \sqrt{(x^2 + y^2 + z^2)};$$

filtering the magnitude of the vector signal ($Mag_{vs}$) over the QRS, ST and T wave intervals through a low pass filter to establish a smooth vector signal ($VS_{sm}$) and a maximum value and time of the QRS interval ($QRS_{max}$ and $QRS_{maxtime}$); differentiating the smooth vector signal ($VS_{sm}$) from the magnitude of the vector signal ($Mag_{vs}$) over the QRS, ST and T wave intervals and establishing a derivative vector signal ($dVS_{sm}$); calculating a set of initial parameters from the QRS interval including: the magnitude of the maximum QRS signal ($QRS_{max}$); the maximum of the QRS time interval ($QRS_{maxtime}$); and the end point of the initiation of the QRS signal ($QRS_{EndInit}$); calculating a set of initial parameters from the T wave interval including: the magnitude of the maximum T wave signal ($Twave_{max}$); and the maximum of the T wave time interval ($Twave_{maxtime}$); calculating an initial estimate of the end of the QRS interval ($QRS_{EndInit}$); fitting the vector signal along a cubic polynomial curve; calculating the change in the derived vector signal ($dVS_{sm}$) over a prescribed time period to establish a smooth test interval ($S_{Test}$); fitting a first order polynomial curve to the initial vector signal ($Mag_{vs}$) starting at the end of the QRS interval (QRS_EndInit) to a point which is equal to the end of the QRS interval (QRS EndInit) plus the smooth test interval ($S_{Test}$); and calculating the intersection of the cubic polynomial curve and the first order polynomial curve and selecting a point of intersection that is furthest from the time of the maximum QRS value ($QRS_{maxtime}$)to establish the J point.

The step of monitoring and storing an initial electrocardiogram vector signal (x, y, z) of a known non-ischemic condition over the QRS, ST and T wave interval may also include the step of: estimating a magnitude and angle of the ST offset at the J point and the J point plus sixty milliseconds (60 ms).

While apparently generally acceptable for their intended purposes, so far as is known, none of the prior art devices display an electrocardiograph heart signal in vector format within a single three-dimensional coordinate system sampled at incremental time intervals which comprises a point of origin and a three-dimensional coordinate system comprising an x-axis, a y-axis and a z-axis extending from the point of origin. The present disclosure further includes a frontal plane defined by the area between the x-axis and the y-axis, a sagittal plane defined by the area between the z-axis and the y-axis and a transverse plane defined by the area between the x-axis and the z-axis. The magnitude and location of the signal are displayed within the coordinate system at incremental time intervals using a plurality of vectors, the displaying mechanism emanating from the point of origin.

It is also an object of the present invention to provide a device which interprets the sampled data from an ECG digitally recorded signal at certain time intervals and projects this signal as a vector from a point of origin to a point in 3-D space as related to the X, Y and Z axes. Such display information can include various intervals and critical parameters relating to the ECG signal, e.g., P-wave, QRS interval including the initiation and end points of the QRS interval, ST segment, J point, T wave, etc. In addition, other information relating to the magnitude of the vector differences and the angle (elevational and azimuth values) may also be displayed relating to two ECG signal taken over a period of time. It is envisioned that measuring, calculating and displaying this information may lead to better analysis and heart monitoring techniques.

The present disclosure also eliminates the step-by-step analytical process of determining heart conditions and ischemic events and provides a new techniques and new displays which are intended to enhance recognition of the presence and type of malfunctions related to the cardiac muscle.

As mentioned above, it is envisioned that the display can integrate other information about the heart onto the same display which it is believed will further enhance diagnostic analysis, e.g., a calibrated display of the magnitude of the vector (Magnitude=squareroot $(X^2+Y^2+Z^2)$) for easier evaluation of hypertrophy and possibly other conditions; displaying the change in Magnitude from one vector to the next, which is believed to be an indication of the continuity of heart muscle cell activation and an additional indicator of disease; and displaying the change in the angle of the heart vectors over the same time interval which is believed to be a further indicator of muscle cell activation and smoothness of transition of the depolarization of cells over the myocardium.

By visually projecting the results of the 3-D heart vectors (and accompanying information relating thereto) onto three planes, namely, the frontal, the transverse and the sagittal planes, heart analysis is greatly simplified and further enhanced. The display is preferably color-coded to distinguish the vector sequence over the QRS cycle, e.g., by color coding the time of occurrence of the events in the QRS cycle, the ST offset, and the T-wave to clearly show their interrelationship and timing which is important to the recognition of normal versus diseased conditions.

Further embodiments of the display allow a physician or medical technician to manipulate the vector display to facilitate more detailed examination of any portion of the vector sequence as a function of time, e.g., the vector display may be expanded or magnified to highlight and allow closer examination of certain areas; the vector display may be shifted in steps both horizontally and vertically from its present location; the vector display may be rotated about the vertical axis 360 degrees, and elevated or declined about the X-axis in steps; and the T-wave, P-wave or other portion of the display may be removed if it interferes with the observation of other portions of the signal.

These and other aspects of the present invention are described in greater detail below.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

In the drawings, wherein similar reference characters denote similar elements throughout the several views.

DETAILED DESCRIPTION

Conventional cardiographs display electrocardiograph heart signals in vector format within a conventional coordinate system comprising the "x" and "y" axes. The present disclosure relates to a vector cardiograph coordinate system sampled at incremental time intervals which comprises a point of origin and a three-dimensional coordinate system comprising an x-axis, a y-axis and a z-axis extending from the point of origin. As defined, the three dimensional coordinate system includes a frontal plane defined by the area between the x-axis and the y-axis, a sagittal plane defined by the area between the z-axis and the y-axis and a transverse plane defined by the area between the x-axis and the z-axis. One such system is described in commonly-owned U.S. Pat. No. 5,803,084 the entire contents of which is incorporated herein in its entirety. The '084 patent discloses a displaying mechanism which displays the magnitude and location of the signal within a three dimensional coordinate system at incremental time intervals using a plurality vectors wherein the displaying mechanism emanates from the point of origin. For the purposes herein, only a brief explanation of the above-identified patent is described as it relates to the present disclosure.

Figure 1A:
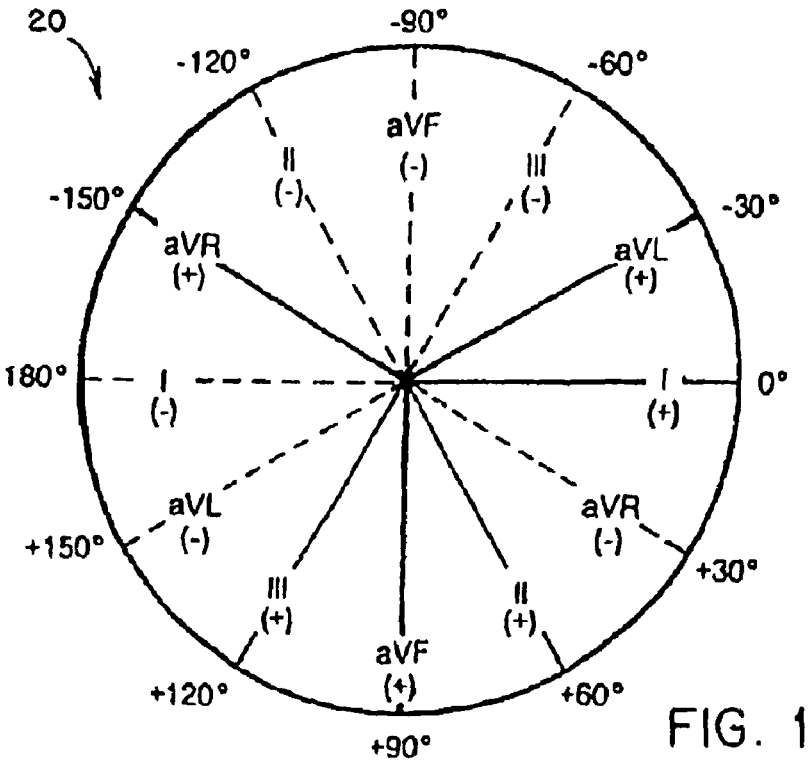
FIG. 1A is an illustration of the Hexial System showing the six leads in the frontal plane.
Figure 1B:
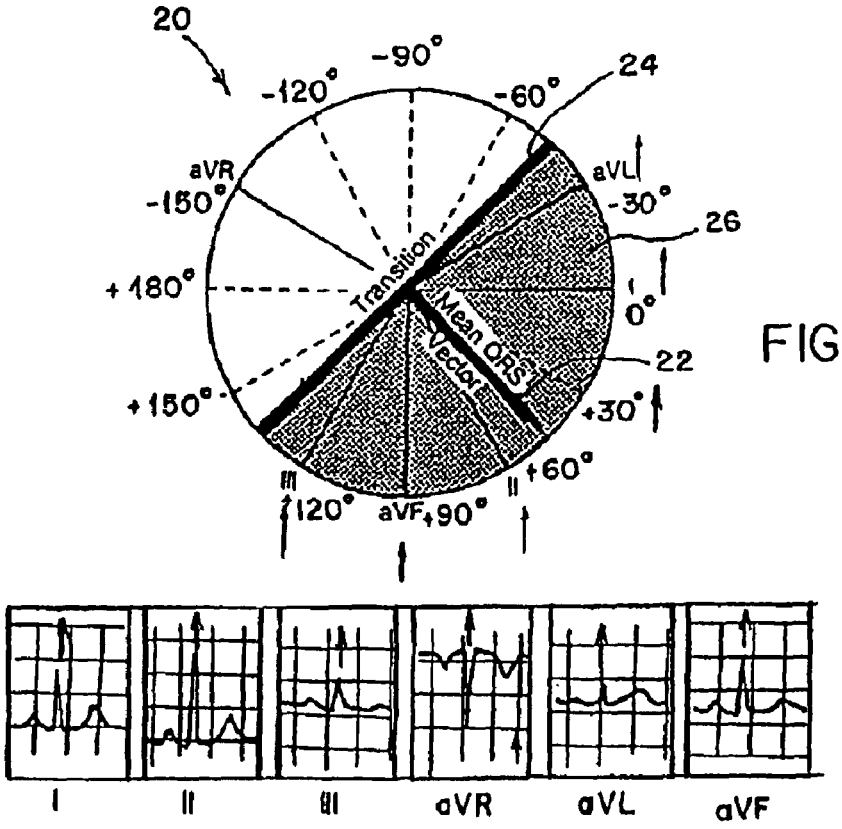
FIG. 1B illustrates how the six Leads, I, II, III, a VR, a VL and a VF are translated onto the IIexial System of FIG. 1a to graphically depict the mean QRS Vector, the Transition Line, and the positive side of the Transition Zone.
Figure 2A:
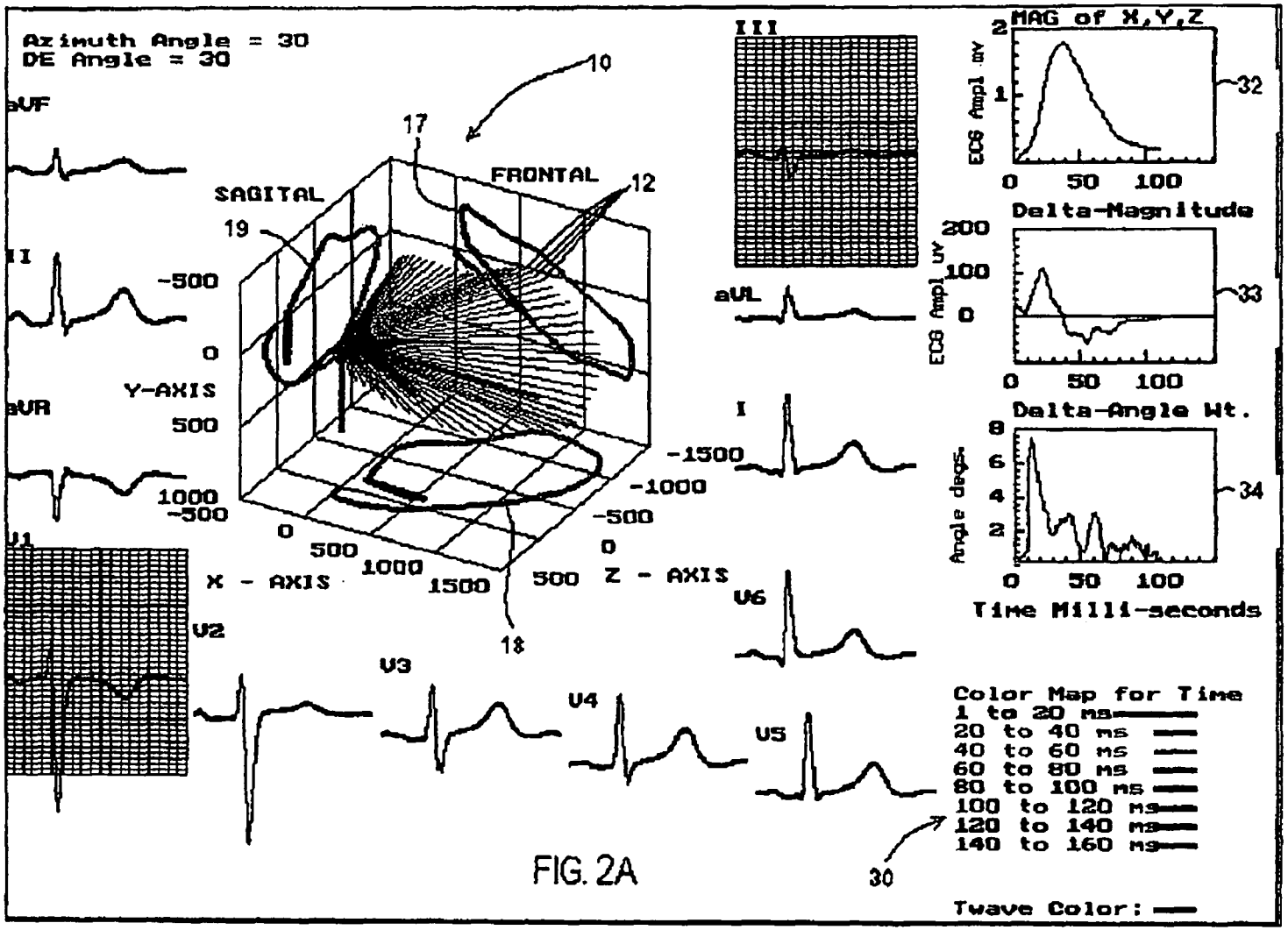
FIG. 2A is a 3-D vector cardiographic display of a normal heart shown with several accompanying displays on a single screen.
Figure 2B:
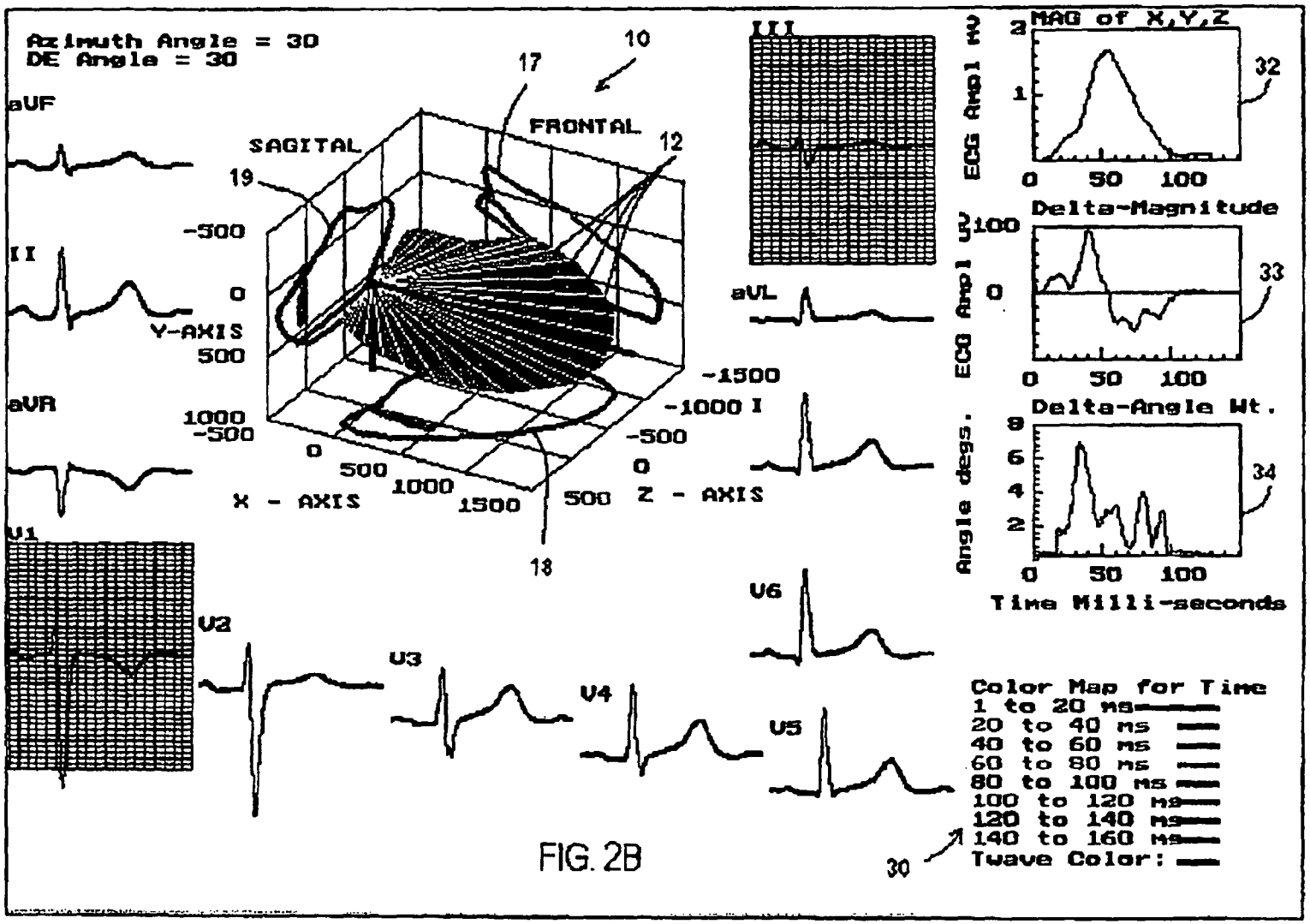
FIG. 2Bb is the 3-D vector cardiographic display of FIG. 2a showing the integration of surface modeling techniques between vectors.

FIGS. 2A and 2B show an example of a 3-D vector cardiographic display 10 of the QRS interval of a normal heart. In this particular case, the heart vectors 12 for the QRS interval are determined at 1 ms intervals. The vectors 12 are color-coded over 20 ms time intervals so the sequence of the vectors 12 over the entire QRS interval can be easily discerned. The color coding sequence or map 30 can be selectively displayed by a physician when needed.

It is believed that displaying the heart vectors 12 in this novel fashion enables a physician to visually perceive critical information for the diagnosis of heart disease. Displaying the heart vectors 12 in this fashion also provides a good visual clue as to the plane of the vectors 12 over the entire QRS interval, which is also important for diagnosing heart disease. It is also much easier to interpret the results of a 3-D vector representation, since it relates directly to the orientation of the heart in the body, and the deviation from a normal pattern becomes immediately obvious even to the untrained observer.

FIG. 2A also combines the standard displays of the 12-Lead system, the 2-D vectorgrams and the 3-D vector display. Preferably, the accompanying displays do not interfere with the 3-D vector display 10 and are generally positioned at various locations around the display 10. For example, in FIG. 2A the various Leads from the 12-Lead system are positioned around the 3-D vector display in a general counterclockwise manner starting with the a VF lead at the upper left corner of the display 10 following to the III lead at the upper right corner of the display 10. Preferably, it is possible for a physician to selectively manipulate any or all of the lead displays or other accompanying displays to various positions on the screen. Other accompanying displays can include various graphs 32, 33, 34 representing, e.g., the changes in magnitude and angle of the heart vectors and/or a display of the color map for readily distinguishing the various vectors.

As can be appreciated from the present disclosure, a physician can selectively determine which display he wants to view at any particular time during the diagnosis. Further, it is within the scope of the present invention to allow a physician to selectively manipulate, e.g., magnify (zoom in), color, or rotate any one of the displays at any given time. Although the 3-D vector display 10 is believed to be far superior than the other displays, by combining the 3-D vector display 10 with theses other displays on a single screen, it is believed that most, if not all, known heart conditions can be readily observed. For example, by also projecting the results or terminal points of the vectors 12 simultaneously onto each of the three respective planes (frontal, transverse and sagittal) of the 3-D vector display thereby forming 2-D vector cardiographic projections 17, 18 and 19 on the same screen as shown in FIGS. 2A and 2B, it is much easier for a physician to visualize conditions that may be hidden on the 3-D display 10 without rotating or expanding the display 10.

FIG. 2A illustrates the normal heart of FIG. 2A with the spaces between vectors 12 filled and/or shaded. Preferably, these spaces are color mapped in a manner similar to the vectors. Advantageously, surface modeling and hidden line representation techniques are employed to further enhance the picture.

Figure 3:
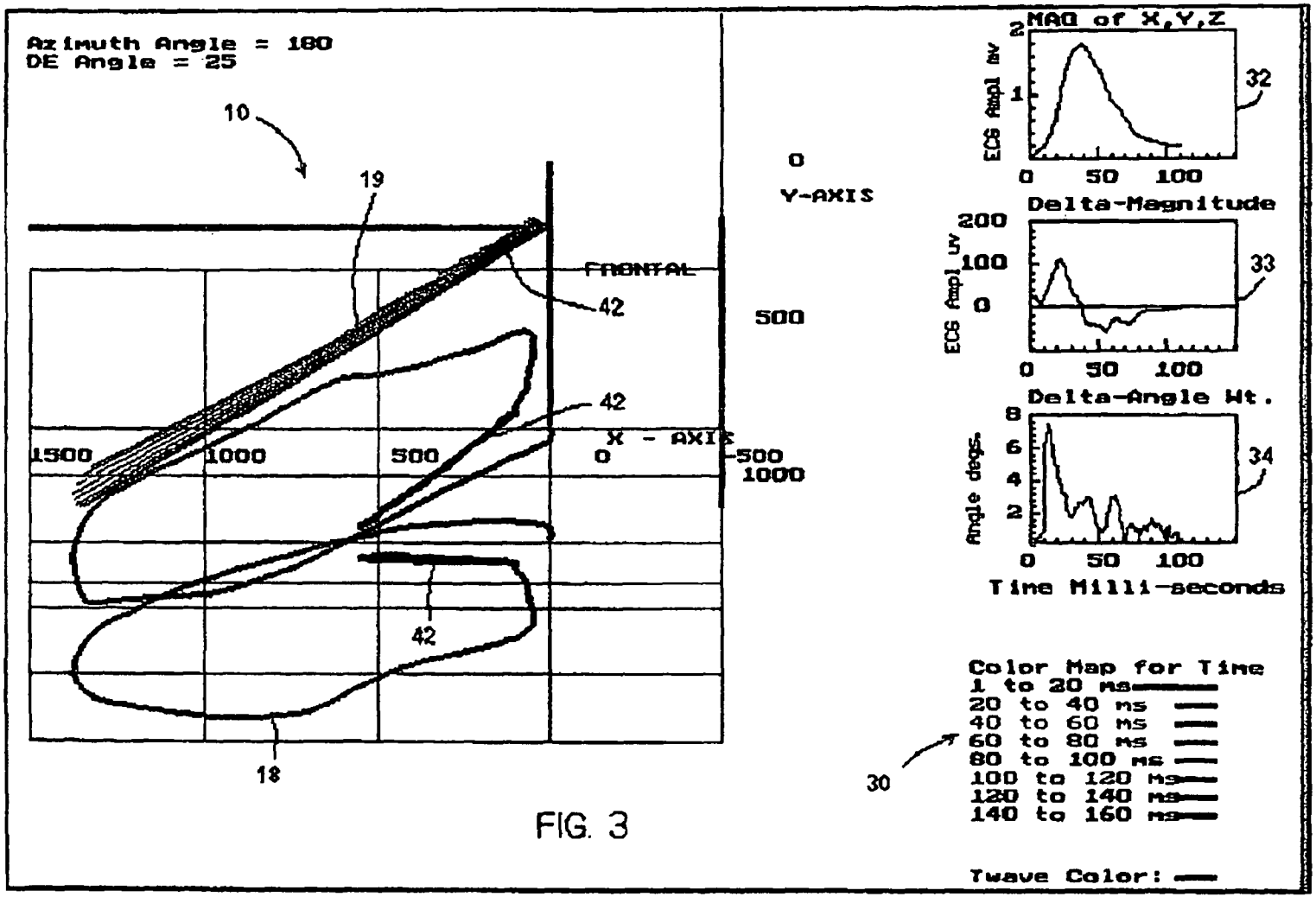
FIG. 3 is a 3-D vector cardiographic display of a normal heart of FIG. 2 at a 180° azimuth showing the slant of the plane of heart vectors.

FIG. 3 shows the normal heart of FIG. 2 which is rotated about a 180° azimuth. As can be appreciated from the present disclosure, a physician is able to manipulate the 3-D vector cardiogram 10 for viewing purposes. For example, by rotating the vector display of FIG. 2A, it is possible to observe that the vectors 12 fall within a single plane. The angle of this plane can be easily measured as an indicator of the orientation of the axis of the heart in the body. As can be appreciated from the present disclosure, the 3-D vector cardiogram 10 can be manipulated in many fashions to view or highlight certain aspects of the display, e.g., the T-wave 42 can be readily observed as being oriented along the same axis as the main axis of the QRS complex which characteristic of a normal heart.

Figure 4A:
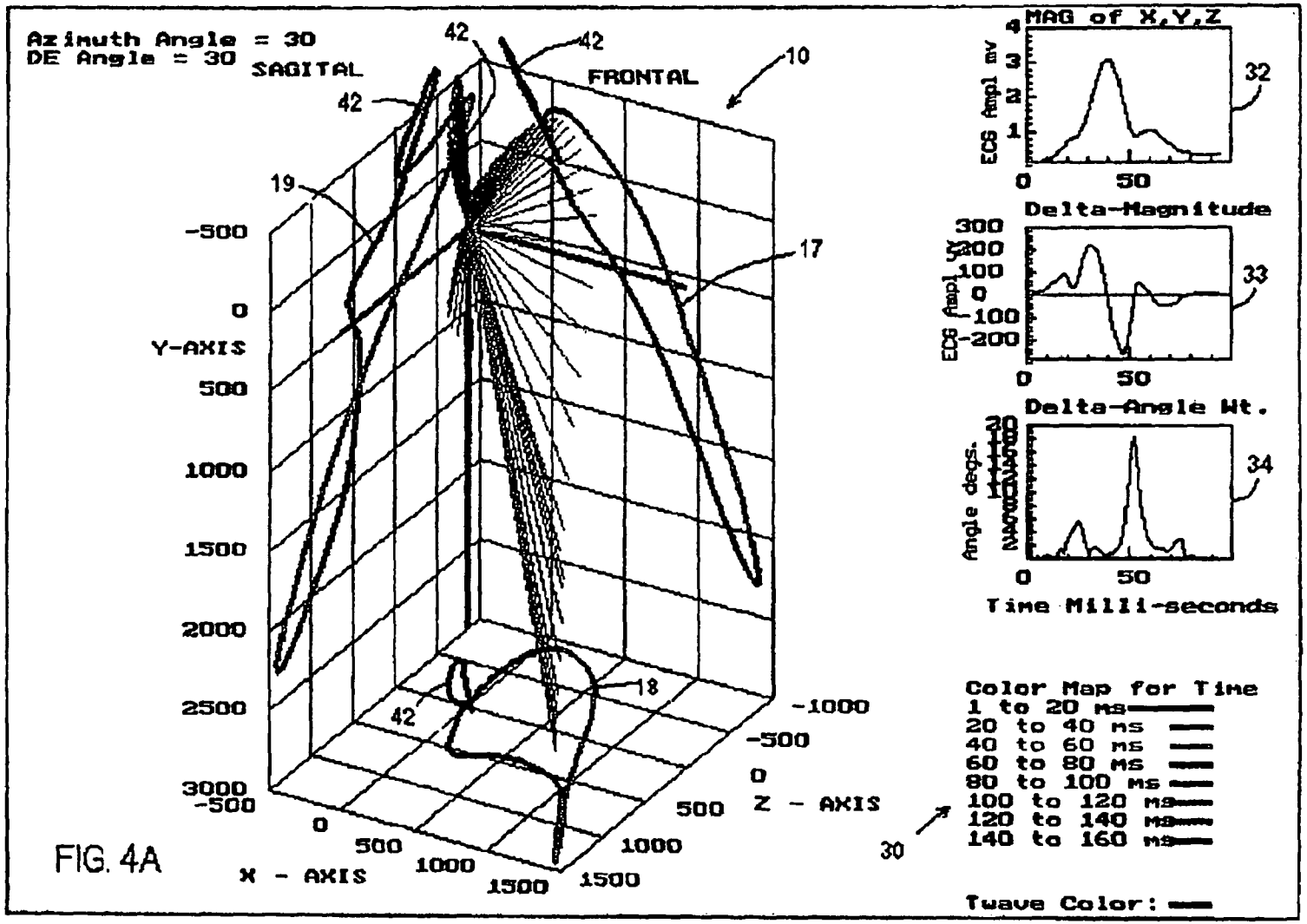
FIG. 4A is a 3-D vector cardiographic display of a heart with left ventricular hypertrophy.
Figure 4B:
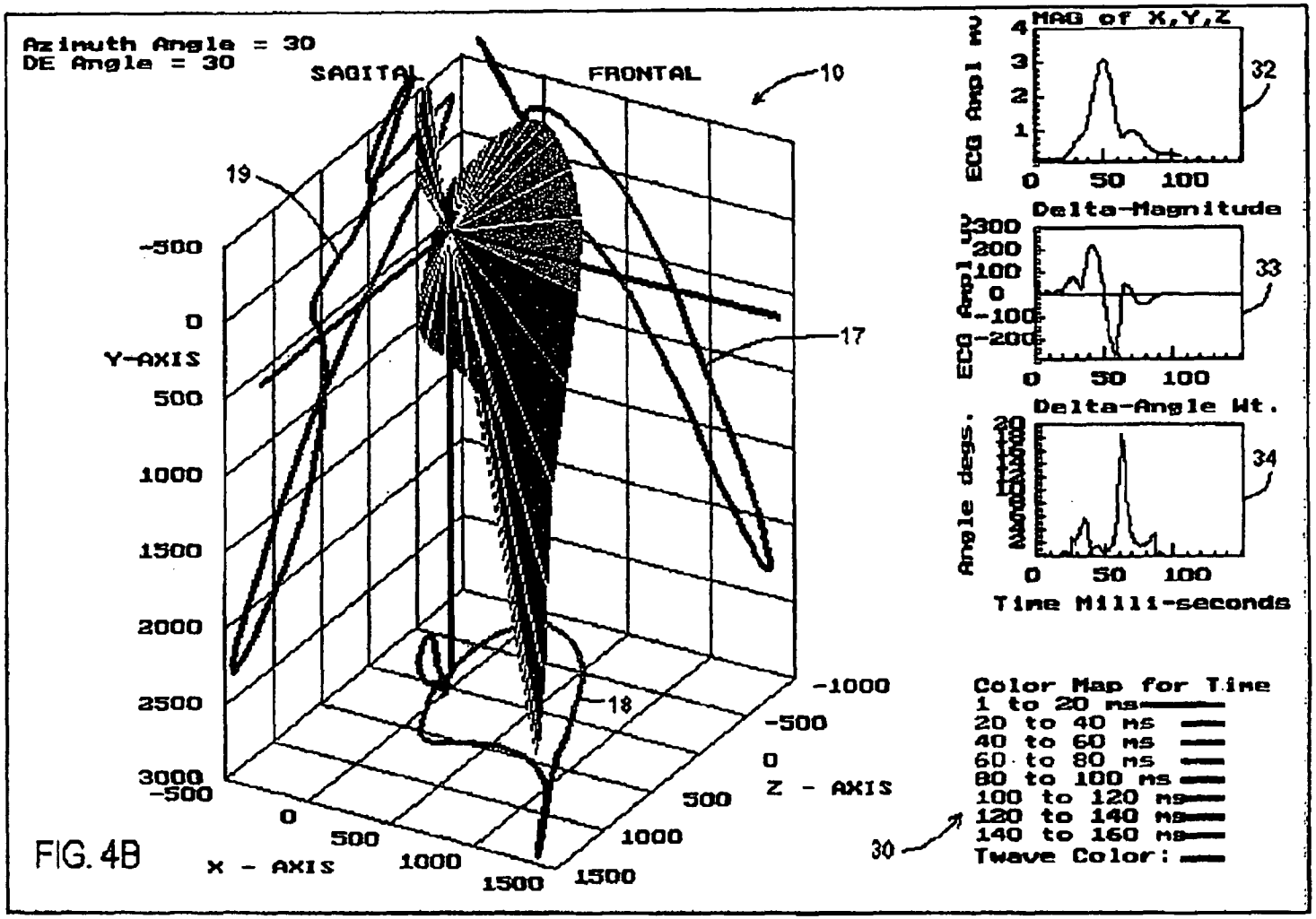
FIG. 4B is the 3-D vector cardiographic display of FIG. 4a showing the integration of surface modeling techniques between vectors.

In contrast to this normal heart we show the case of a heart with hypertrophy—i.e. enlarged heart muscle—shown in FIGS. 4A and 4B. The QRS complex starts out in a normal manner over the first 25 milliseconds, then the magnitude increases very rapidly to a maximum of 3 millivolts. As can be appreciated, an abnormal condition is easily and immediately discernible which was not necessarily the case with displays of the past.

In the case of FIG. 4A, the vector direction of this maximum (anterior, inferior and left) and its time of occurrence could indicated a enlargement of the muscles in the apex of the heart. Diagnosis is left ventricular hypertrophy. Other parts of the ECG signal and their respective locations and directions over the time interval can also be easily and immediately identified. For example, in FIG. 4A, the T-wave 42 is in the reverse vector direction of the main axis of the heart, which is also an indicator of hypertrophy. FIG. 4B illustrates the same heart using surface modeling and hidden line techniques.

As can be appreciated from the present disclosure, the size, shape and smoothness of this vector plane allows a doctor or technician to immediately determine whether the patient has a healthy or unhealthy heart, thereby expediting the task of making a proper diagnosis. For example, if the display shows colors that represent intervals of time over 100 ms, a physician will immediately know that there is a problem, e.g., "Bundle Branch Block". Further, if the physician observes that the plane of the heart vector diagram is split into two planes, or, if the plane is above the x-axis, again, the physician immediately recognizes that there is a problem which is believed to be a myocardium infarction (as related to coronary heart disease). As can be appreciated from the present disclosure, analysis of the 3-D vector cardiographic display can identify any number of other maladies more quickly that conventional methods and may more accurately recognize maladies previously unobserved. In addition, it is envisioned that the presently disclosed 3-D vector cardiographic display coupled with one or more of the presently-disclosed methods described herein may enable more accurate analysis of non-ischemic versus ischemic conditions during heart monitoring.

The vector direction of the T-wave 42 is important for diagnostic purposes and, as can be appreciated, is immediately apparent from the various figures, in particular, FIG. 4A. If the T-wave 42 points in the opposite direction to the main body of the QRS, a problem is indicated. It is believed that the T-wave's 42 direction is indicative of the location of infarction or ischemia that exists in the diseased heart, i.e. anterior, lateral, inferior, or posterior or combinations of these. The P-wave (not shown) can also be integrated into the display (in a similar manner as the QRS interval). This P-wave has diagnostic potential for functions of the atrium of the heart, e.g., the initial electrical pulse form the S-A node, and careful study of the P-wave when displayed in the manner of the present invention may enable a physician to easily pinpoint the location and/or problems with the atria.

Figures 24A, 24B:
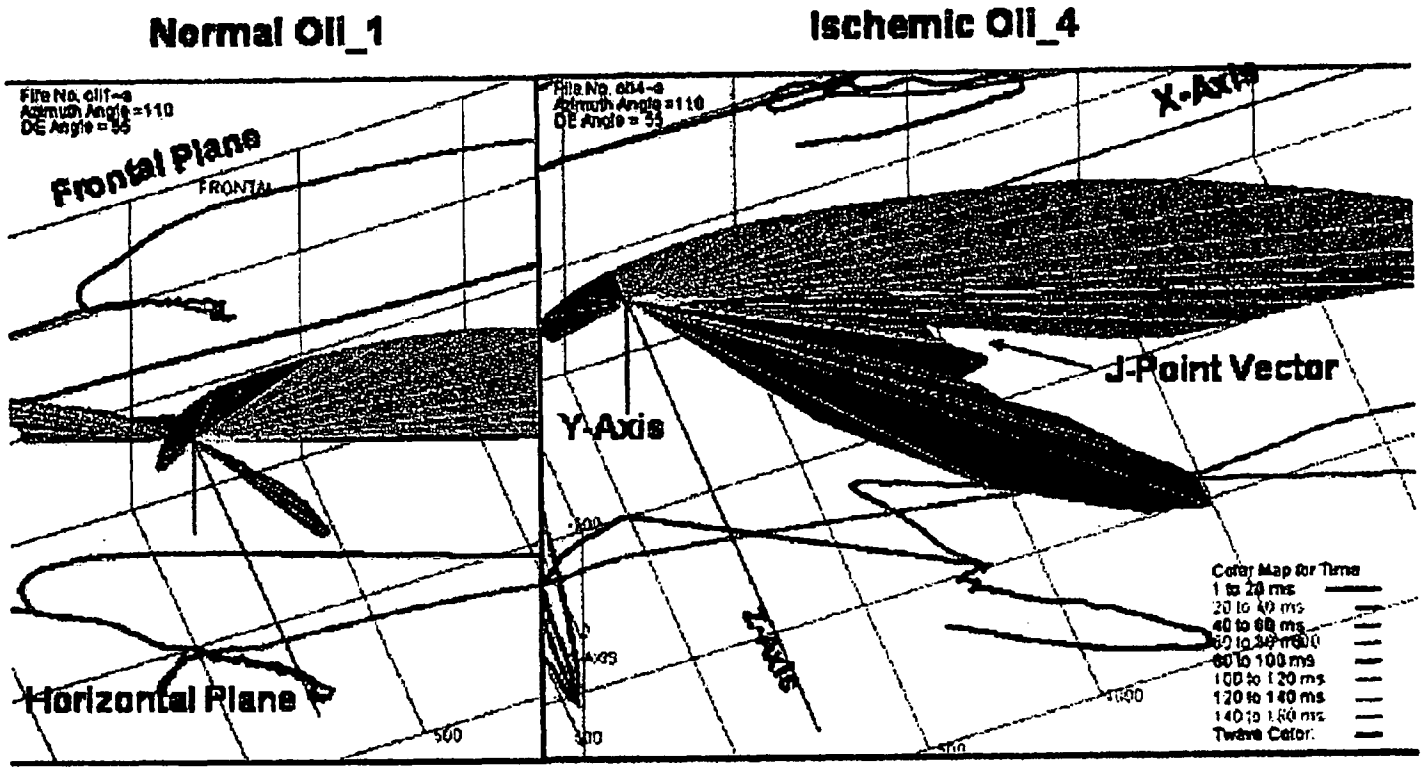
FIG. 24A is an enlarged 3-D cardiographic vector display highlighting a vector offset of a normal heart condition.
FIG. 24B is a greatly-enlarged 3-D cardiographic vector display due to an ischemic condition highlighting a time period of prior to the J point to the end of the T-wave.

Moreover, the detection (and display) of a patient's J-point (i.e., the junction between the end of the QRS and the beginning of the ST segment) is a critical parameter for determining if a patient has had an ischemic event (See FIGS. 24A and 24B). Typically, measuring the J-point is a part of an initial screening process in the Emergency Room at a hospital if the patient thinks that he/she has had an ischemic event. A patient is typically put on an ECG to determine if the J-point is elevated above his/her normal J-point amount (if known or determinable) or the changes in the J-point over time reach a certain threshold. In addition, as explained in more detail below, the detection of the J-point is important for other reasons as well, in particular, to help ascertain a false ischemic condition (i.e., change in patient position) from a true ischemic condition (e.g., heart attack).

It is believed that the display of the vectors 12 in small time intervals, e.g., from about 0.5 ms to about 10 ms, provides potential for diagnosing early signs of potential for ventricular fibrillation and/or Ventricular tachycardia (VT). In has been seen in some of the cases which exhibit severe myocardial infarction that the vectors 12 over these regions are very irregular, i.e., the changes in magnitude and angle of the vectors are not smooth. Studies of the movement of the excitation of heart muscle cells in the region of infarction show that barriers exist to the smooth conduction of muscle excitation. Several of the illustrated cases of the present invention display these effects, namely, the fluctuation of these vectors, which can be seen from their spatial irregularity.

As mentioned above, additional displays 32, 33 and 34 can also be selectively combined with the 3-D vector cardiograph 10 to show the amplitude and angle fluctuations between successive vectors 12 of the 3-D display 10. These displays 32, 33 and 34 are a measure of the smoothness of the vector 12 motion and may provide additional information of the degree of damage that may exist in the heart muscle. The displays 32, 33 and 34 are calibrated in time with the QRS interval and thus can be readily associated with the 3-D vector display 10 to identify areas of roughness.

The magnitude of the vectors 12 calibrated in time over the QRS interval is selectively displayed by graph 32 as seen in several of the illustrations, e.g., FIG. 2A. As described in more detail below, it is believed that the magnitude of the vectors 12 provides a good measure of the maximum amplitude of the heart signal which is an important tool in the diagnosis of heart conditions, e.g., left ventricular hypertrophy. Moreover and as explained in more detail below, calculating the vector magnitude is an important step for determining false heart conditions from true ischemic events. In the case of the 12-Lead system, it is necessary to add the levels from a number of the electrodes in order to gain an idea of this amplitude, whereas this graphic display gives a direct unambiguous measure.

Display 33 shows the change in magnitude between successive vectors. It is believed that this change is a measure of the smoothness of the traveling of the muscle cell excitation wave front through the myocardium. Erratic changes are an indication of disrupted or infarcted tissue and thus provides a qualitative indication of tissue health. In addition and as explained in more detail below with respect to FIGS. 13-23, calculating the difference in magnitude between two ECG signals (e.g., an initial or control ECG signal and a later monitored ECG signal (or parts of each of the same)) is an important step in determining false heart conditions and true ischemic events.

Display 34 shows the change in angle between successive vectors. This is another measure of the character of the muscle cell excitation wave front. This display reveals erratic changes which are believed to be indicative of diseased tissue. This display also shows rapid and fast changes in vector direction which it is believed is indicative of the end of muscle excitation in one region of the heart and transfer to another region. Measuring the angle difference between an initial or base ECG signal and a subsequent ECG signal is also an important step in determining false heart conditions and true ischemic events.

Figure 5A:
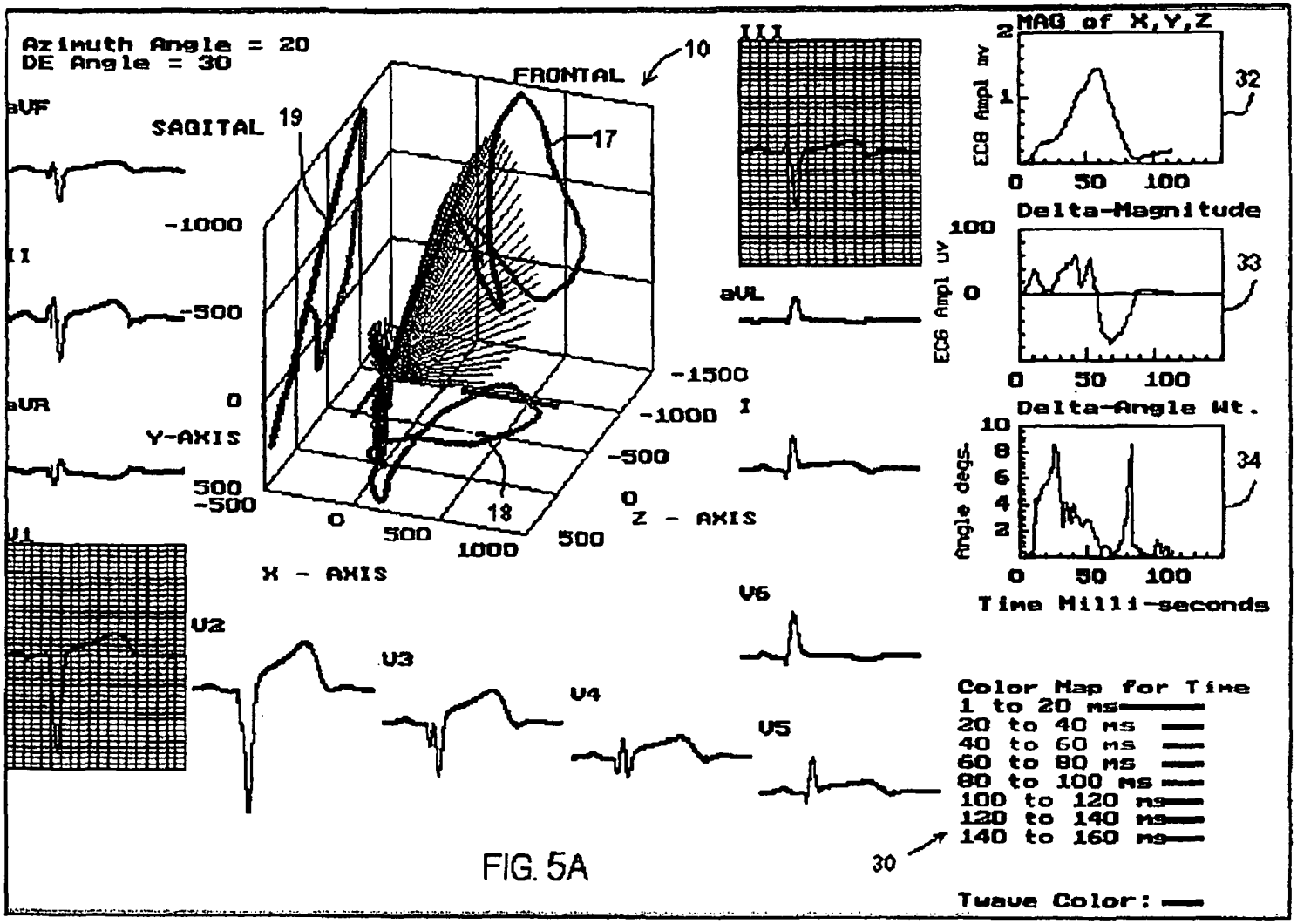
FIG. 5A is a 3-D vector cardiographic display of a heart showing anterior/inferior infarct along with several accompanying displays.
Figure 5B:
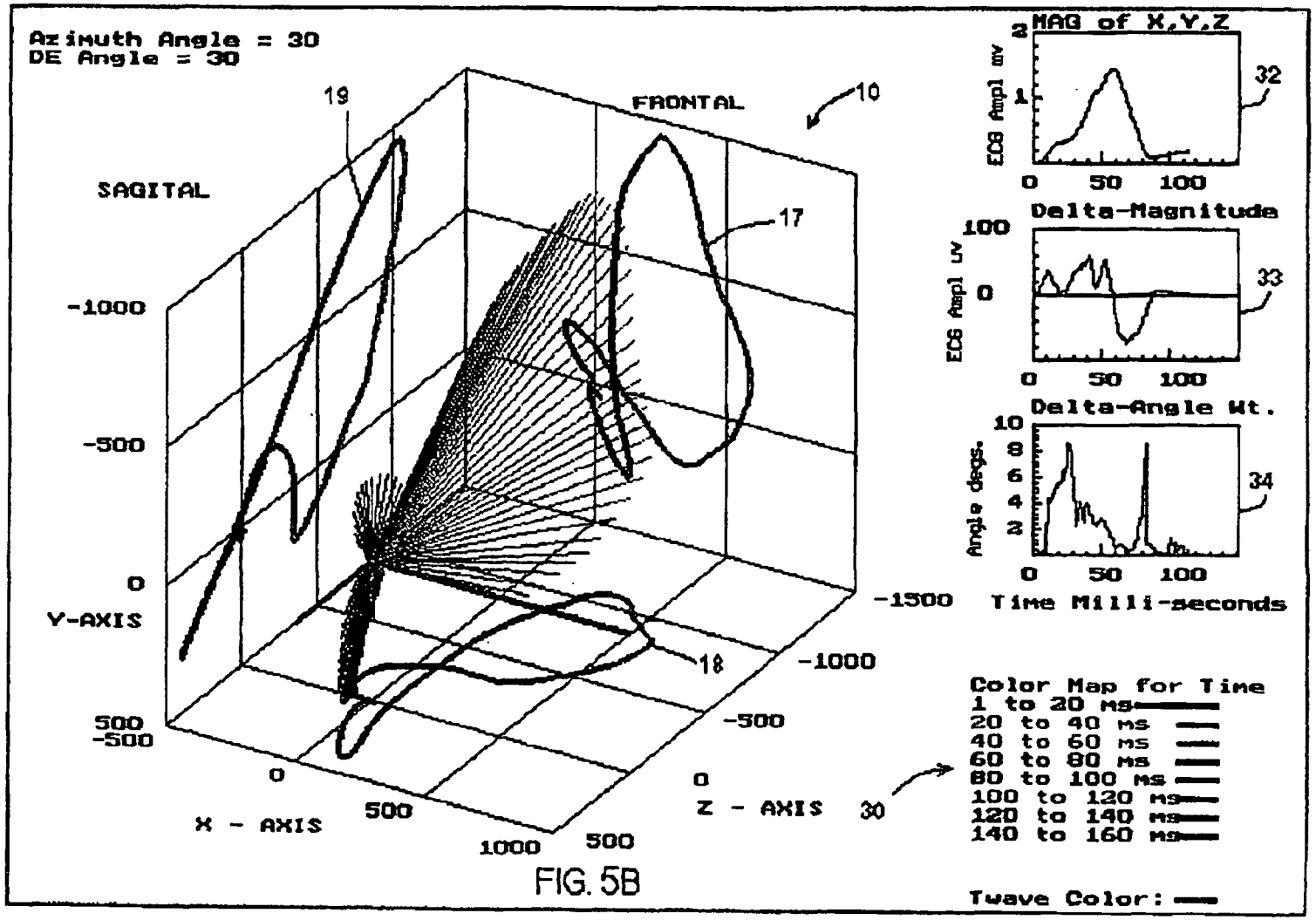
FIG. 5B is an enlarged view of the 3-D vector cardiographic display of FIG. 5a shown without the 12-Lead displays.
Figure 5C:
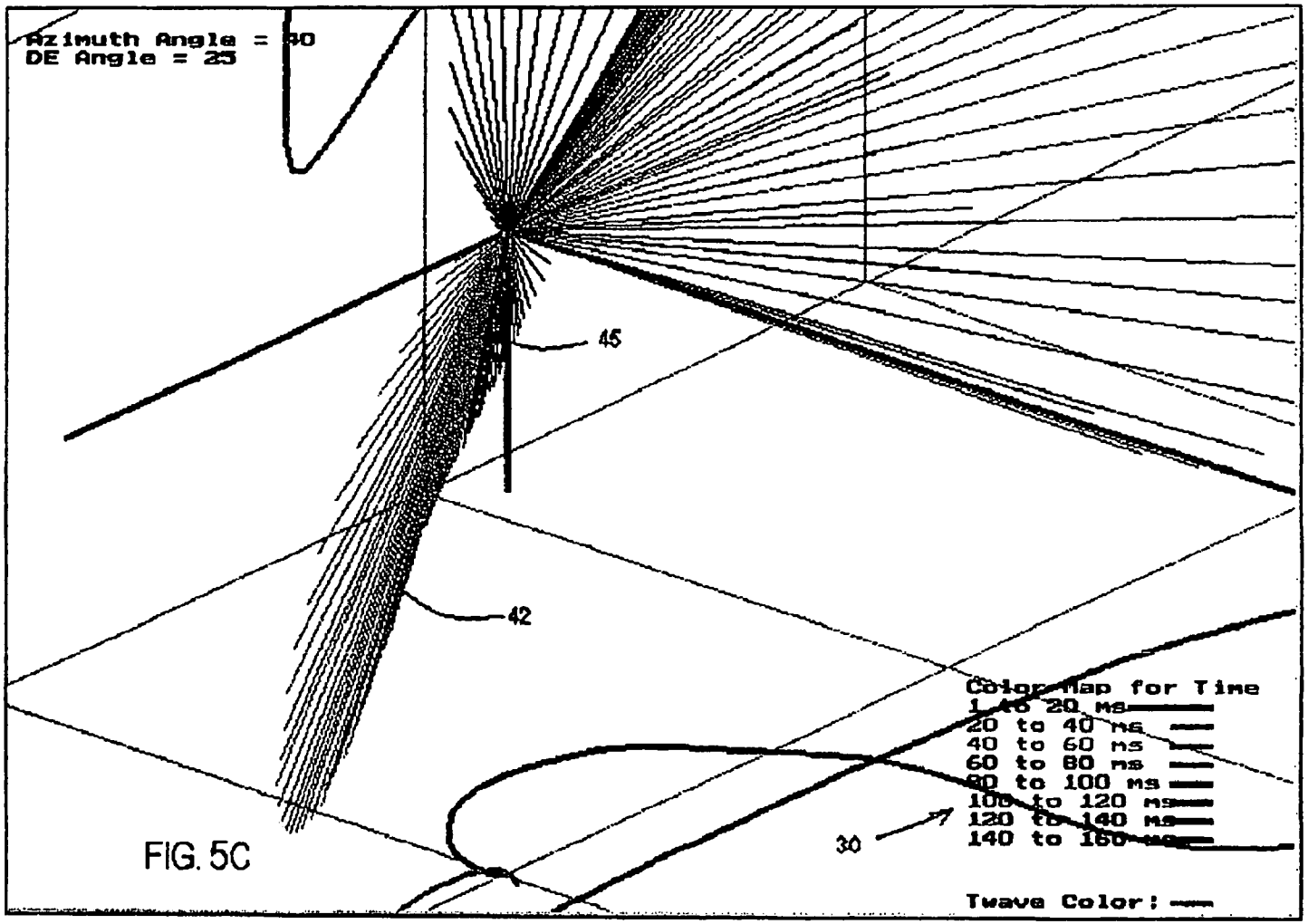
FIG. 5C is a highly enlarged view of the 3-D vector cardiographic display of FIG. 5a highlighting the ST vector in the color red.

Another illustration of heart disease is shown in FIG. 5A. In this case there is definite indication of anterior heart disease. This has been diagnosed from the 12-Lead data that is shown. The deviation of the vector diagram 10 is also clearly shown. The initial vector direction is right, then posterior, then a progression towards the left, followed by a large increase to the posterior, superior direction. This is shown in FIG. 5B and FIG. 5C in larger display. The entire diagram could be produced by taking a normal heart vector diagram and adding a vector in the opposite direction of the anterior and inferior region of the heart whose vectors are not being generated due to a loss of function. When the QRS is completed it docs not return to zero but has an offset. This offset can be incorporated into the 3-D display via an additional vector 45 (color coded in bright red) as seen best in FIG. 5C. This vector represents the end of the QRS interval and the very beginning of the ST interval. It is believed that this vector 45 can be useful in the diagnosis of the location of ischemia or infarction. As depicted by vector 45 in FIG. 5C, the magnitude and direction of the ST voltage offset, if any, is easily recognizable on the display because it is distinguished in color. In addition, it is believed that the position and orientation of the vector 45 offset is useful for determining the location in the heart of the failure, such as the coronary artery that is blocked, e.g., the direction of the vector 45 points to the location of the ischemia. The magnitude of this vector 45 is also useful since it has been seen to relate to a recent ischemic episode. For example, in the case illustrated in FIGS. 5A-5C, the vector 45 points to the anterior and inferior location, which confirms the original diagnosis from the direction of the disturbed QRS vector diagram. As can be appreciated from the present disclosure, other indicators than color may be employed to distinguish vector 45 or any other vector 12, e.g., shading and/or varying the line weight and type.

Figure 6:
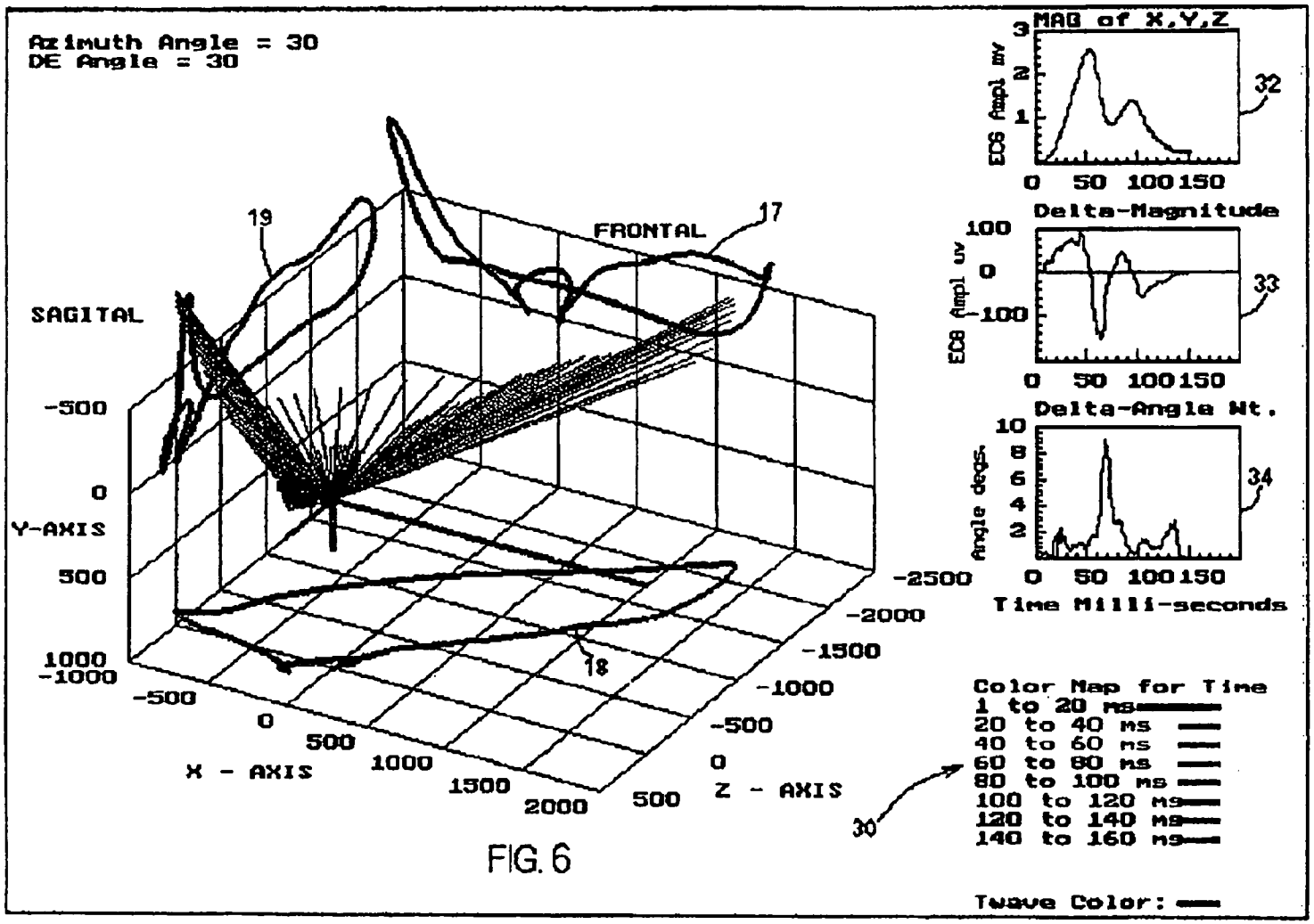
FIG. 6 is a 3-D vector cardiographic display of a heart showing left bundle branch block.

Another case is shown in FIG. 6 of a patient with LBBB (Left Bundle Branch Block). This illustration shows the large amount of detail that is available from the vector display 10 concerning the sequence of excitation of the heart muscle in these cases. In the case of LBBB the right ventricle is excited first by the Purkinje right bundle. The muscle cells then conduct the depolarization process to the left ventricle. The paths established in this manner are different from the case of normal excitation. As a result, the vector diagram is different from the normal case (See FIGS. 2A, 2B and 3) as is obvious from the appearance of the display 10. One result which is immediately perceivable is the fact that the duration of the QRS signal is much longer than the normal QRS process, which is the first criteria for BBB—i.e. the QRS complex is longer than 110 ms.

It is also possible to apply the 3-D vector display 10 to data taken in real time. FIGS. 7-11 shows some examples as a series of 3-D cardiograms shown from real time QRS and T-wave data shown for a normal heart. These were consecutive heart cycles and are interesting for the possible assessment of changing vector 12 characteristics from beat to beat as may be the case for ischemic or infarcted tissue.

Figure 7:
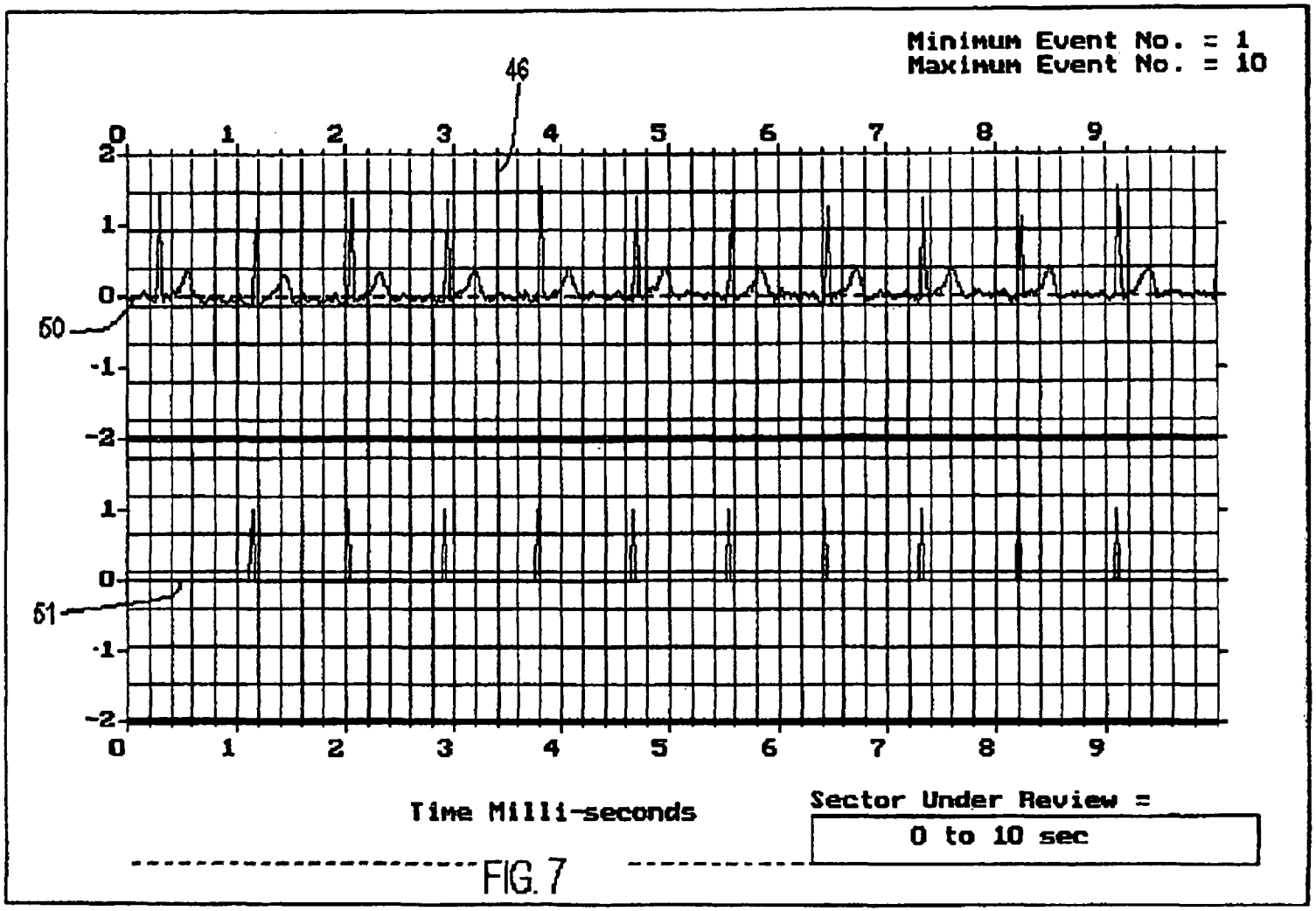
FIG. 7 is a graphical display of a series of detectors of events over 10 seconds for selection of a real time event to be displayed in 3-D vector cardiographic format.
Figure 8:
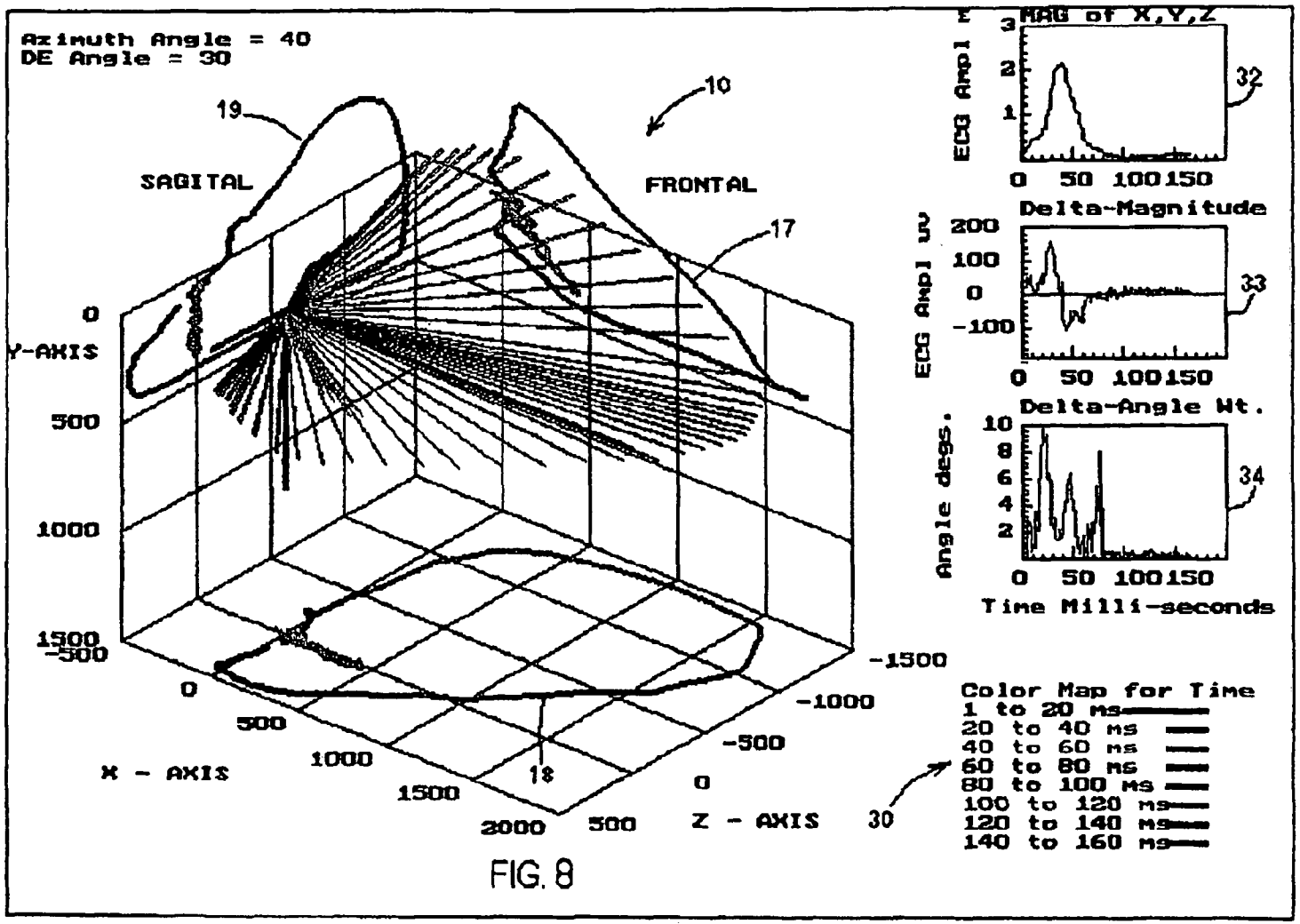
FIG. 8 is a 3-D cardiographic vector display of event No. 6 of FIG. 7.
Figure 9:
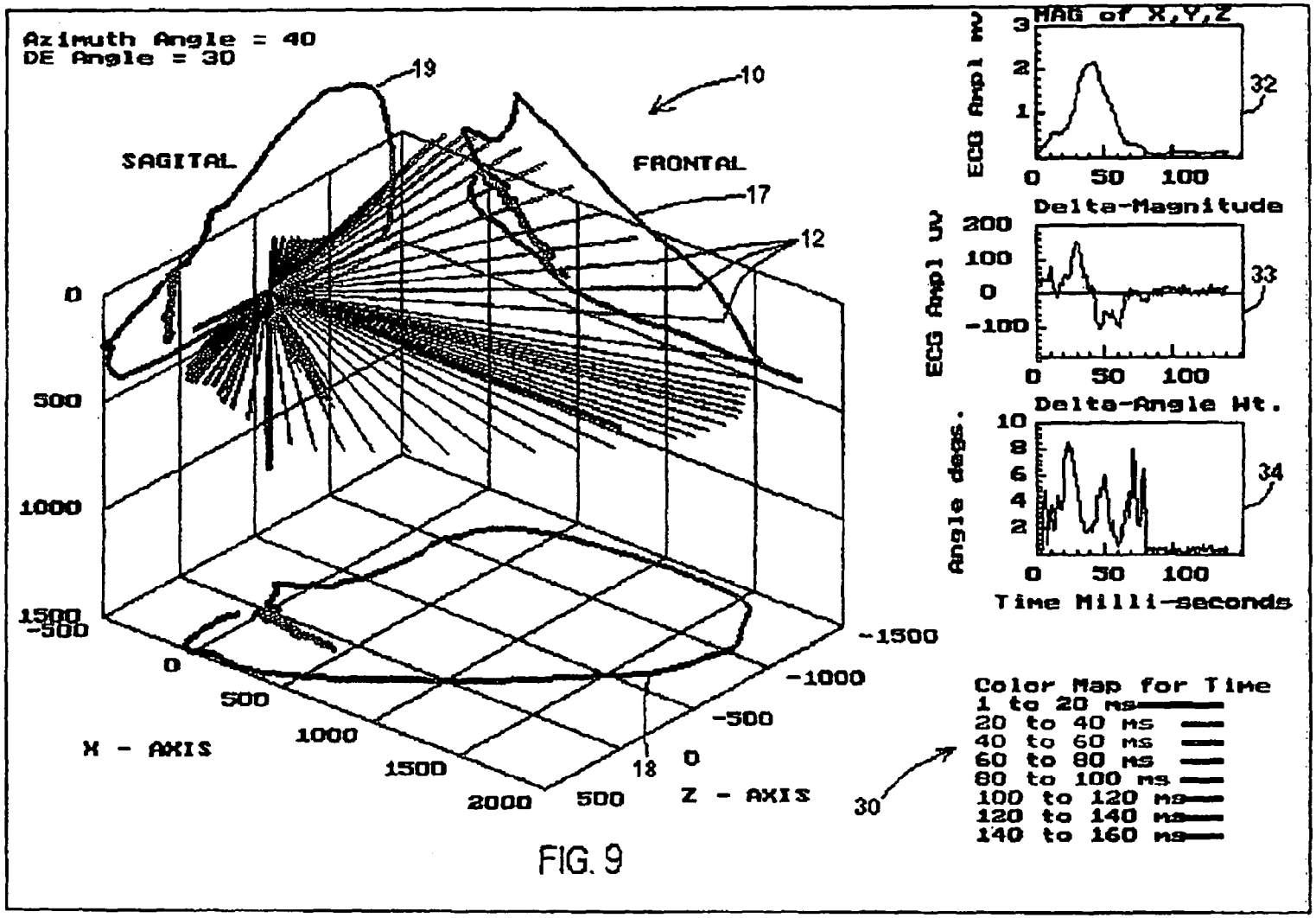
FIG. 9 is a 3-D cardiographic vector display of event No. 7 of FIG. 7.
Figure 10:
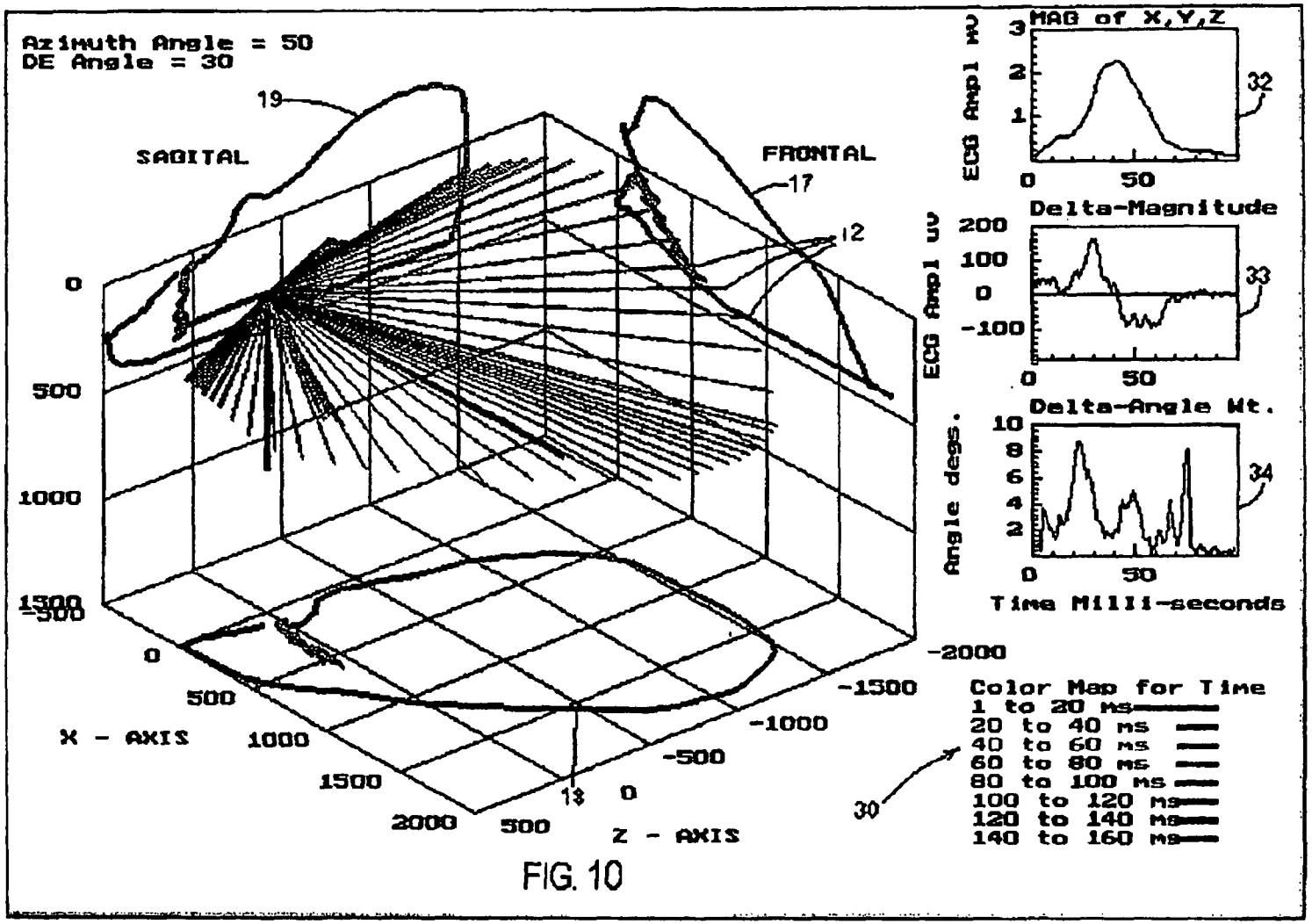
FIG. 10 is a 3-D cardiographic vector display of event NO. 8 of FIG. 7.
Figure 11:
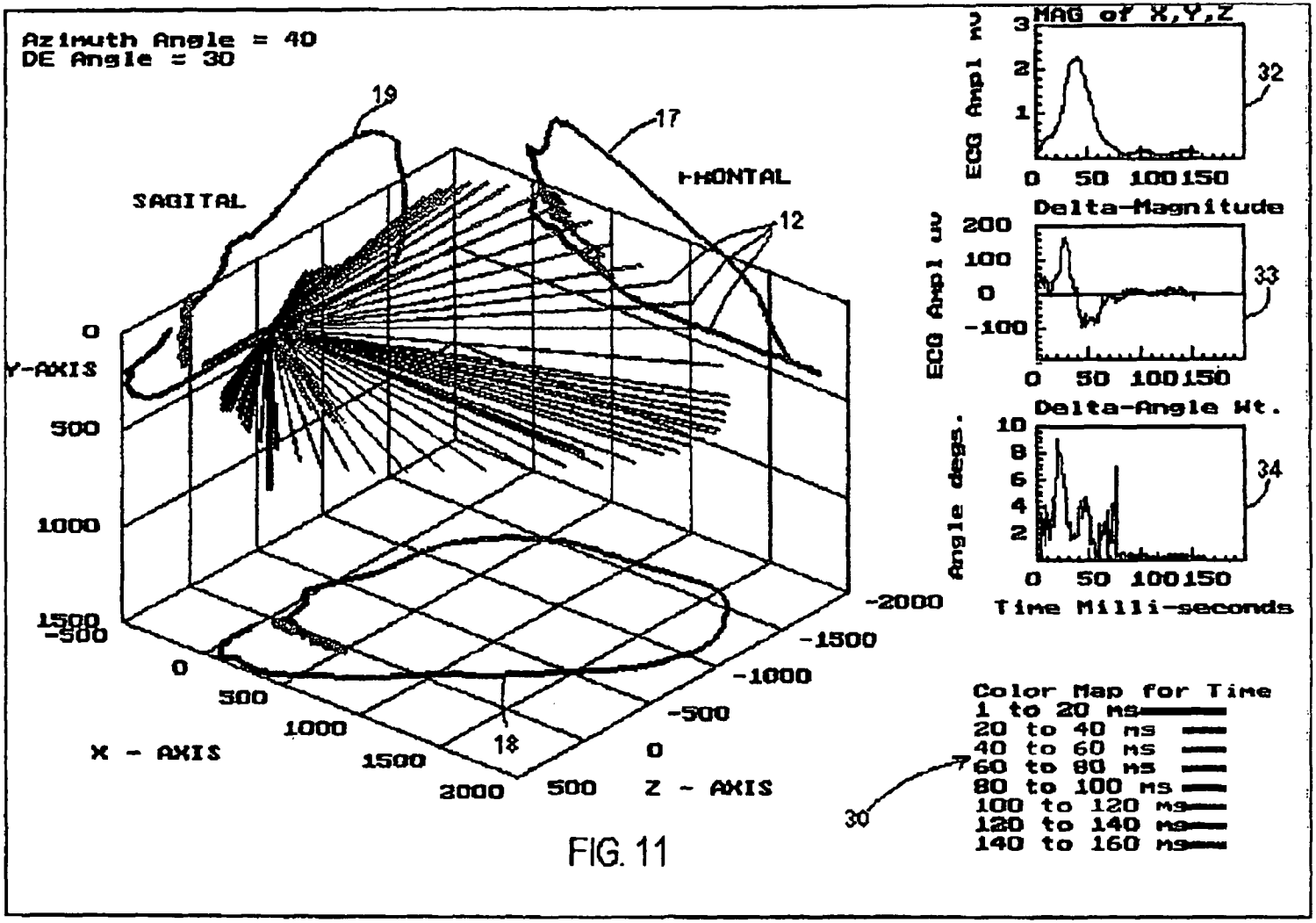
FIG. 11 is a 3-D cardiographic vector display of event No. 9 of FIG. 7.

FIG. 7 shows the detection of the heart QRS complex by an algorithm 46 that looks at one of the X, Y or Z axis signals that has the most rapid increase in signal level at the outset. The signal being used is shown in the upper trace, in this case the X channel 50, and the detector output 52 in shown in the lower trace. A ten second interval is shown. The next four figures, i.e., FIGS. 8-11, show the 3-D vectorgram 10 for events 6 through 9 depicted on FIG. 7. As can be appreciated from the present disclosure, there are small variations from one 3-D display 10 to the next which it is believed may prove to be useful in diagnosing certain disease conditions.

FIGS. 13-28 relate to a method for detecting and monitoring ischemic events. More particularly, the presently disclosed method involves a so-called screening tool (Automatic or visual) which allows physicians and hospital staff to quickly and accurately distinguish between a true ischemic event and a false condition due to patient positional changes.

Figure 25A:
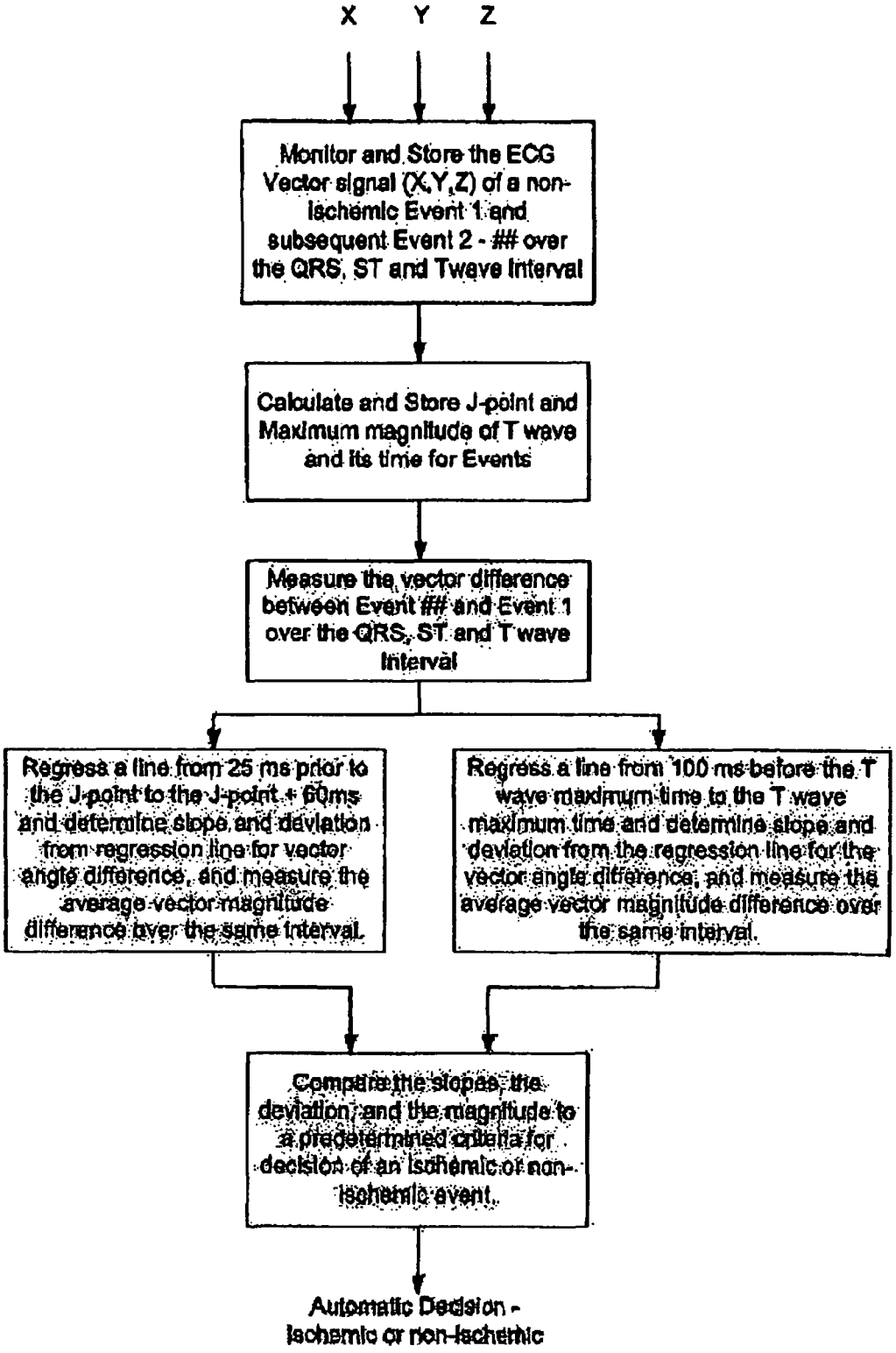
FIGS. 25A-28 show various flow diagrams of the presently described methods disclosed herein.
Figure 25B:
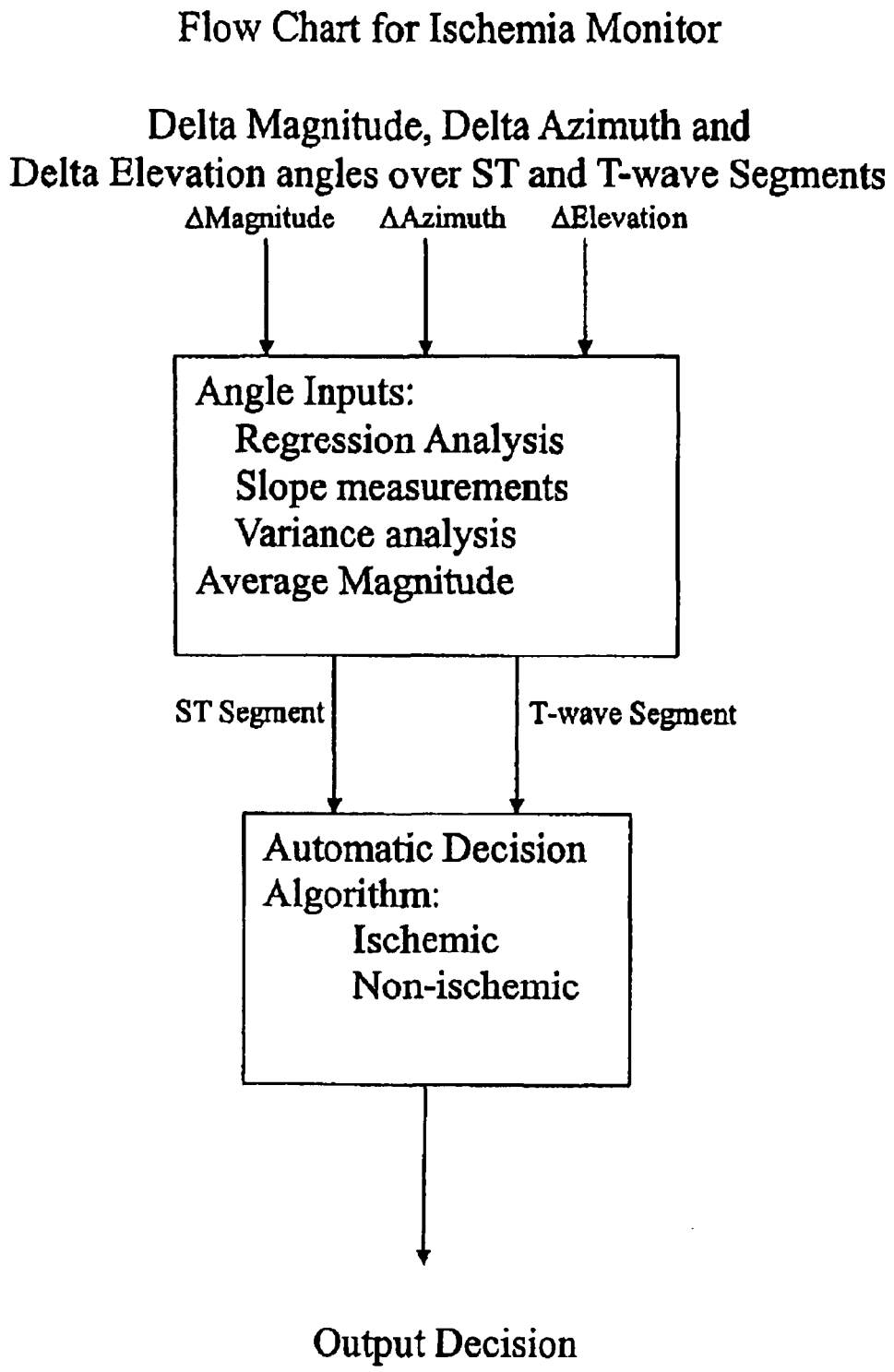
Figure 26:
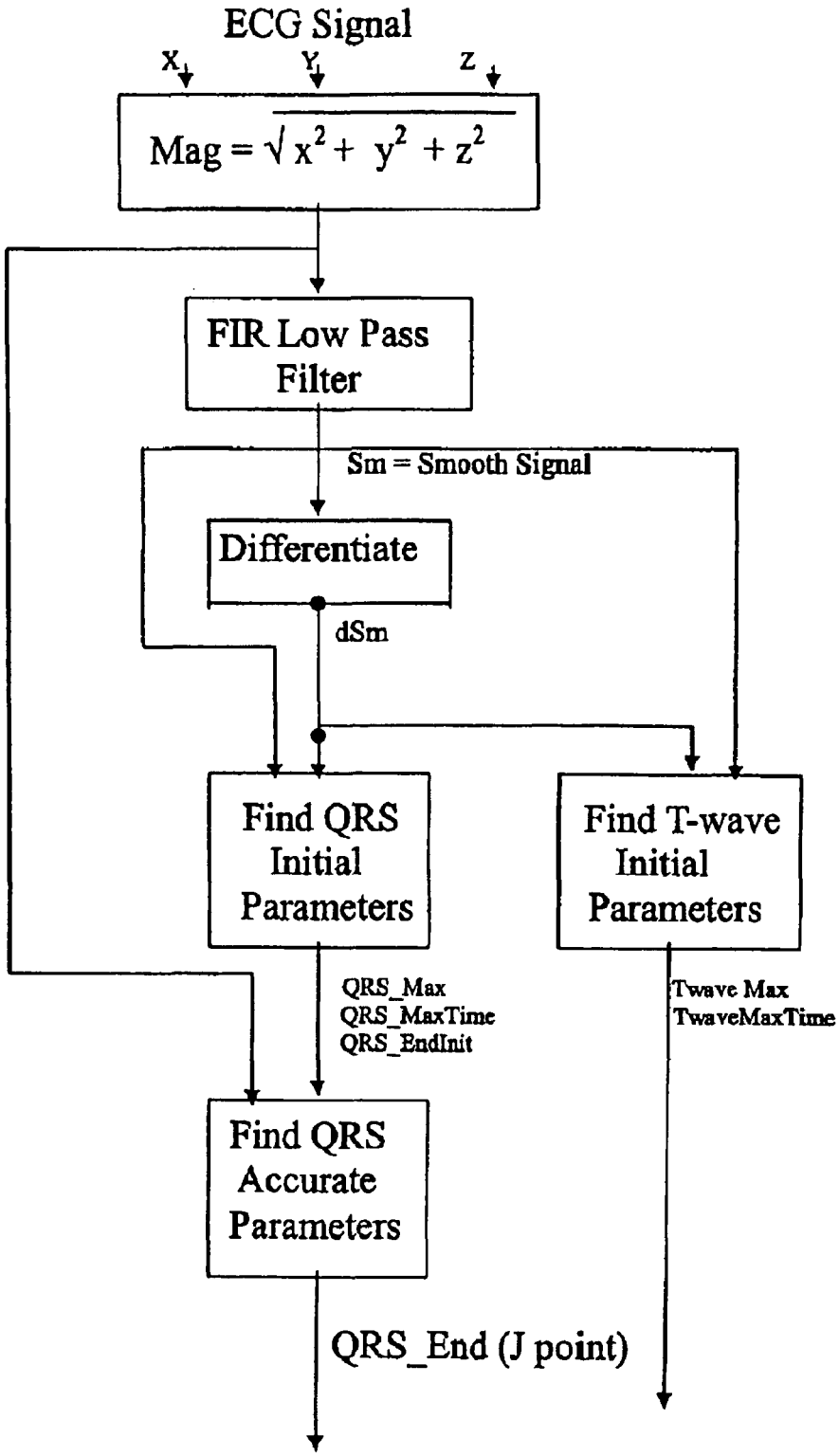
Figure 27:
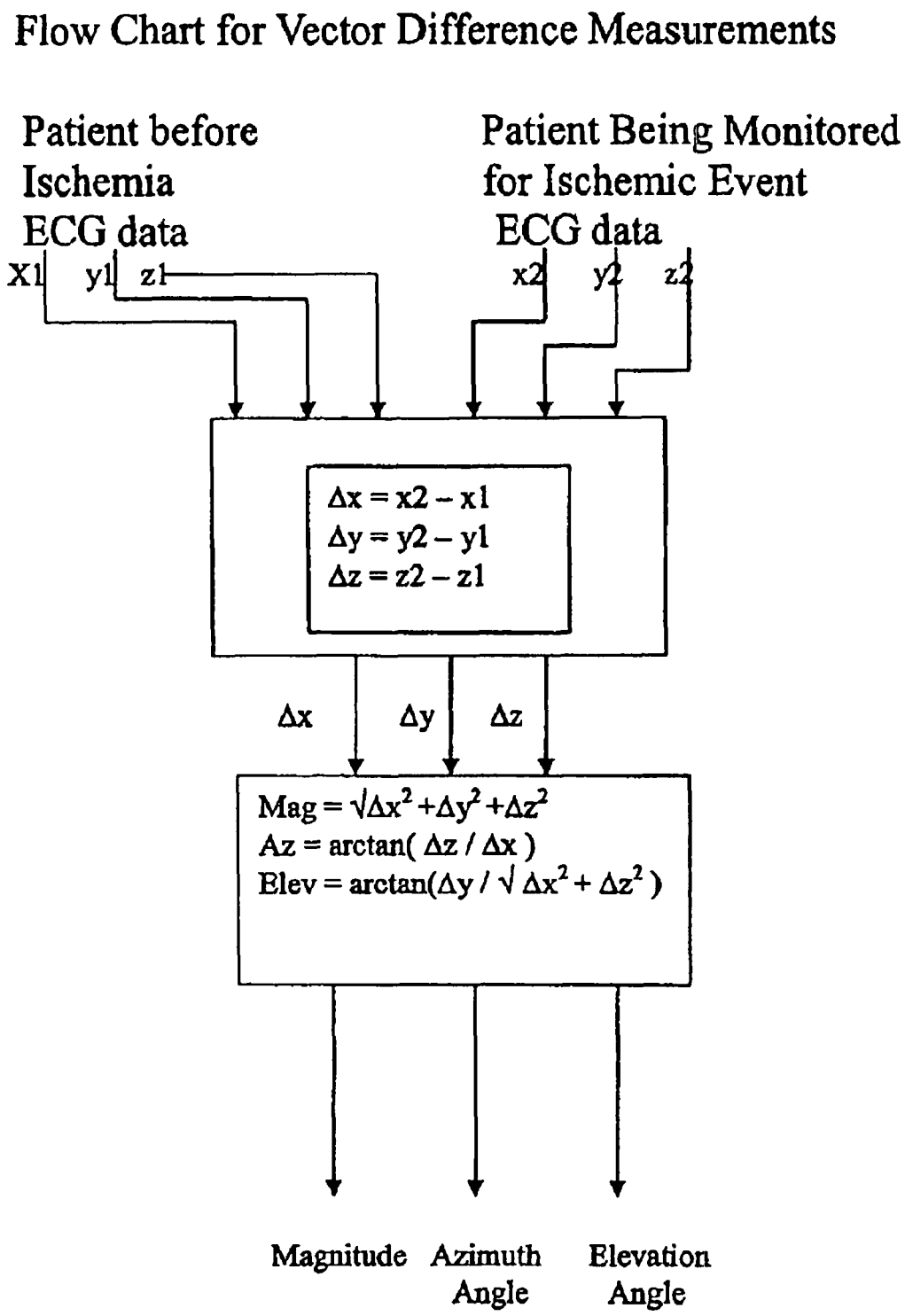
Figure 28:
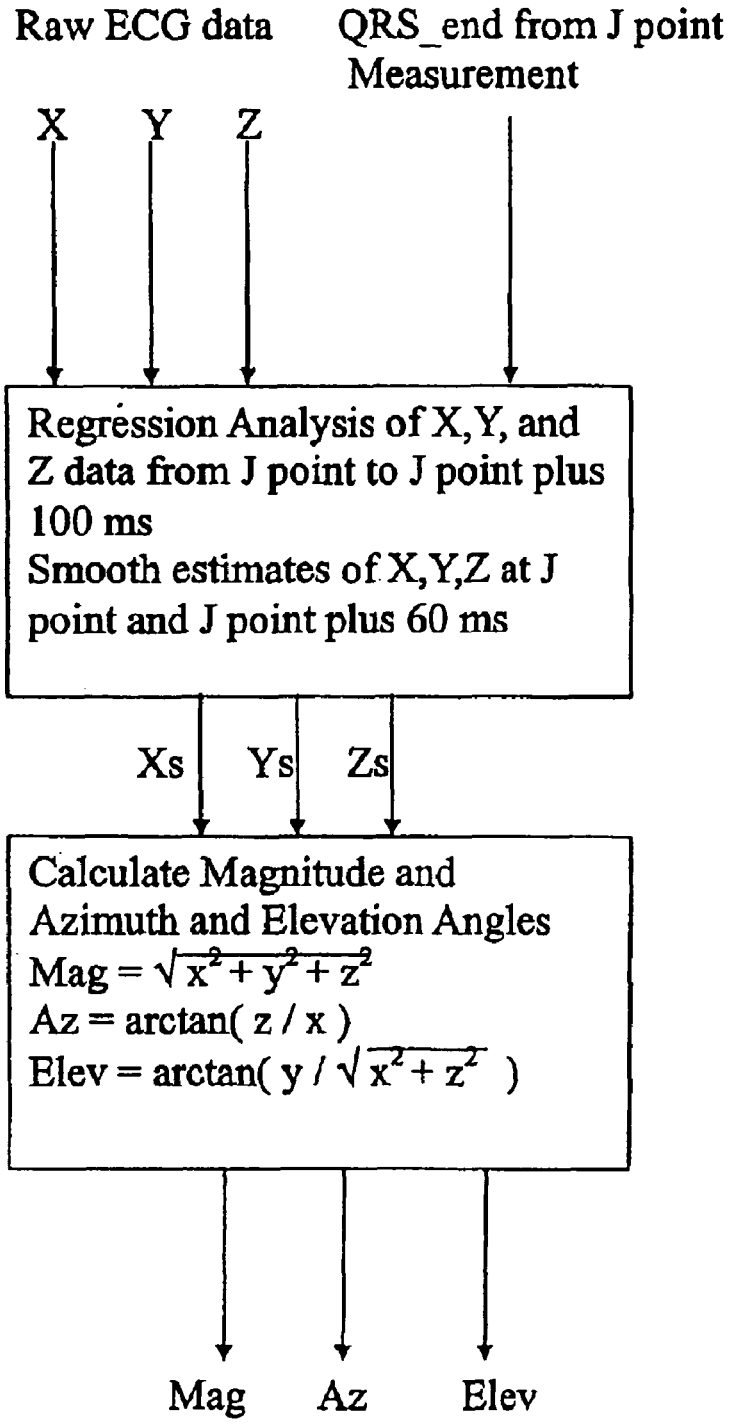

The presently disclosed method involves the steps of: monitoring and storing an initial electrocardiogram vector signal (x1, y1, z1) of a known non-ischemic condition over the ECG signal (QRS, ST and T wave intervals); calculating and storing a J-point of the vector signal and a maximum magnitude of a signal level over the T wave interval; monitoring a subsequent electrocardiogram vector signal (x2, y2, z2) over the QRS, ST and T wave intervals; measuring the magnitude (Mag.) of the vector difference between a subsequent vector signal (x2, y2, z2) and the as initial vector signal (x1, y1, z1); measuring the angle (Ang.) difference between a subsequent vector (x2, y2, z2) and the initial vector signal (x1, y1, z1); regressing a line from points about 25 milliseconds prior to the J point and about 60 milliseconds after the J-point and determining the slope of the regression line and the deviation of the angle difference of the regression line; regressing a line from points about 100 milliseconds prior to the maximum magnitude of the signal level over the T wave interval and determining the slope of the regressing line and the deviation of the angle difference of the regression line; and comparing the slope and deviation of the lines from the J point and the T wave interval to a set of known values to determine the presence of an ischemic event (See Flow chart FIGS. 25A and 25B). A more detailed explanation of the presently disclosed method is described below with reference to FIGS. 13-24.

Other flow charts (See FIGS. 25-28) show the various additional steps of the presently-disclosed method. For example, the step of measuring and storing the magnitude (Mag.) of the vector difference may include the steps of: accessing the stored initial electrocardiogram vector signal (x1, y1, z1) of a known non-ischemic condition over the QRS, ST and T wave intervals; measuring the subsequent electrocardiogram vector signal (x2, y2, z2) over the QRS, ST and T wave intervals; calculating the change (Δ) in the vector signal over the QRS, ST and T wave intervals by the following formula: $\Delta x = x2 - x1$; $\Delta y = y2 - y1$; $\Delta z = z2 - z1$; and calculating the magnitude of the vector difference ($Mag_{vd}$) over the QRS, ST and T wave intervals by the following formula: $Mag_{vd} = \sqrt{(\Delta x^2 + \Delta y^2 + \Delta z^2)}$.

The step of measuring and storing the angle of the vector difference (Ang.) may include the steps of: accessing the stored initial electrocardiogram vector signal (x, y, z) of a known non-ischemic condition over the QRS, ST and T wave intervals; measuring the subsequent electrocardiogram vector signal (x, y, z) over the QRS, ST and T wave intervals; calculating the change (Δ) in the vector signal over the QRS, ST and T wave intervals by the following formula: $\Delta x = x2 -$ x1; Δy=y2−y1; Δz=z2−z1; calculating an Azimuth angle (Az. Ang.) of the angle vector difference over the QRS, ST and T wave intervals by the following formula: Az. Ang.=arc tan (Δz/Δx); and calculating an Elevation angle (El. Ang.) of the angle vector difference over the QRS, ST and T wave intervals by the following formula: El. Ang.=arc tan(Δy/√(Δx²+Δz²)).

As explained in more detail below with respect to FIGS. 13-24, the step of calculating the J point includes the steps of: calculating the magnitude of the initial vector signal ($Mag_{vs}$) over the QRS, ST and T wave intervals by the following formula:

$$Mag_{vs} = \sqrt{(x^2 + y^2 + z^2)};$$

filtering the magnitude of the vector signal ($Mag_{vs}$) over the QRS, ST and T wave intervals through a low pass filter to establish a smooth vector signal ($VS_{sm}$) and a maximum value and time of the QRS interval ($QRS_{max}$ and $QRS_{maxtime}$); differentiating the smooth vector signal ($VS_{sm}$) from the magnitude of the vector signal ($Mag_{vs}$) over the QRS, ST and T wave intervals and establishing a derivative vector signal ($dVS_{sm}$); calculating a set of initial parameters from the *smooth vector signal* ($V_{sm}$) *in the* QRS interval including: the magnitude of the maximum QRS signal ($QRS_{max}$); the maximum of the QRS time interval ($QRS_{maxtime}$); and the initial estimate of the end point of the QRS signal ($QRS_{Endinit}$), *the parameters also including the initial estimated time of the start of the QRS signal* ($QRS_{startInit}$) *by finding the time before the time of occurrence of the maximum smooth vector signal* ($VS_{sm}$) *in the QRS interval* ($QRSVS_{maxtime}$) *that the derivative of the smooth vector signal* ($dVS_{sm}$) *changes polarity from negative to positive* (*see FIG. 19*)*; and the initial estimated time of occurrence of the end point of the QRS signal* ($QRS_{EndInit}$) *by finding the time of occurrence after the time of occurrence of the maximum smooth vector signal* ($VS_{sm}$) *in the QRS interval* ($QRSVS_{maxtime}$) *at which the derivative of the smooth vector signal* ($dVS_{sm}$) *changes polarity from negative to positive* (*see FIG. 19*); calculating a set of initial parameters from the T wave interval including: the magnitude of the maximum T wave signal ($Twave_{max}$); and the maximum of the T wave time interval ($Twave_{maxtime}$); fitting the vector signal along a cubic polynomial curve ($a_3x^3+a_2x.^2+a_1x+a_0$) *from a point that extends from a point about midway between the time of occurrence of the maximum smooth vector signal* ($VS_{sm}$) *in the QRS interval* ($QRSVS_{maxtime}$) *through the initial estimated time of occurrence of the end point of the QRS signal* ($QRS_{EndInit}$) *plus about 20 milliseconds* (*ms*) *at a sample rate of 1 sample per millisecond* (*ms*); calculating the change in the [derived] *derivative of the smooth* vector signal ($dVS_{sm}$) over a prescribed time period *after the initial estimated time of occurrence of the end point of the QRS signal* ($QRS_{EndInit}$) *when the derivative of the smooth vector signal* ($dVS_{sm}$) *exhibits a substantially constant magnitude* to establish a smooth test interval ($S_{Test}$) (*See FIG. 19*); determining a point where the polynomial curve begins to turn upward (point of inflection which indicates the presence of the QRS) by examining the coefficients of the fitted polynomial, i.e., $a^0$ and $a^1$ where $a^1$ is the slope of the curve (μv/ms) and $a^0$ is the offset at the start of the curve; fitting a first order polynomial curve to the initial vector signal ($Mag_{vs}$) starting at the end of the QRS interval (QRS_EndInit) to a point which is equal to the end of the QRS interval (QRS_EndInit) plus the smooth test interval ($S_{Test}$); and calculating the intersection of the cubic polynomial curve and the first order polynomial curve and selecting a point of intersection that is furthest from the time of the maximum QRS value ($QRS_{maxtime}$)to establish the J point *as the end of the QRS interval* ($QRS_{end}$).

Figure 22:
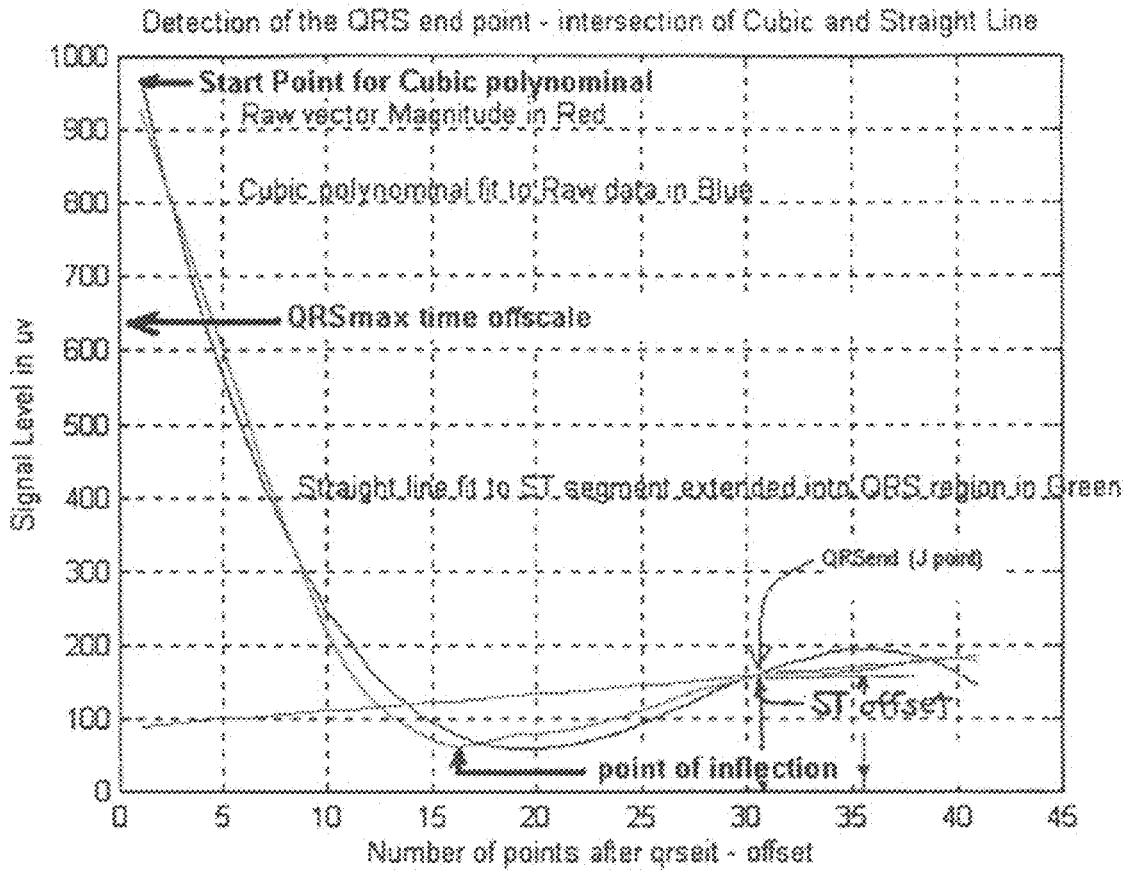
FIG. 22 is a plot showing the raw magnitude of the ECG signal and a cubic polynomial fit to the raw magnitude of the signal to find the end of the QRS interval of the ECG signal which is the J point.

*Referring to FIG. 22, it should be noted with respect to the fitting of the vector signal along a cubic polynomial curve* ($a_3x^3+a_2x.^2+a_1x+a_0$) *that the time of occurrence of the maximum smooth vector signal* ($VS_{sm}$) *in the QRS interval* ($QRS\text{-}VS_{maxtime}$) *is offscale to the left of the vertical axis "Signal Level in μv" as illustrated by the arrow designated "QRSmax time offscale". The point that extends from a point about midway between the time of occurrence of the maximum smooth vector signal* ($VS_{sm}$) *in the QRS interval* ($QRS\text{-}VS_{maxtime}$) *is illustrated by the arrow "Start Point for Cubic Polynomial". The point of inflection that indicates the presence of the QRS is with respect to the "Raw vector magnitude in Red" as illustrated by the arrow "point of inflection".*

After the step of monitoring and storing an initial electrocardiogram vector signal (x1, y1, z1) of a known non-ischemic condition over the QRS, ST and T wave intervals, the method may include the step of estimating a magnitude and angle of the ST offset at the J point and the J point plus sixty milliseconds (60 ms). A more detailed explanation of estimating the magnitude of the ST interval is explained below with reference to FIGS. 23 and 28.

Turning now in detail to the presently disclosed method of detecting and monitoring ischemic events as best shown in FIGS. 13-24, the basic method utilizes one of the characteristics of ischemic tissue which tends to produce a current of injury with a vector magnitude and direction. This underlying vector exists over the entire QRS complex and the T-wave when the difference between the action of the normal heart tissue and ischemic heart tissue are compared. Put briefly, the vector difference between a non-ischemic event and an ischemic event is used as a means of detecting the ischemic event in an ECG monitoring environment. More particularly, even though the vector difference exists over the entire QRS and T-wave cycle in the case of extensive ischemia, a more sensitive measurement for incipient ischemia is found by limiting the examination to regions near the J point and prior to the peak of the T-wave.

The analysis of the vector difference between a patient's reference ECG (or initial ECG vector signal taken during his/her initial emergency room visit or upon admission to a telemetry unit) and the case of ischemia provides a magnitude and angular difference which is found to be different in the case of a patient positional change (e.g., supine to upright) and the case of ischemic events. The presently-disclosed method includes a process for measuring, detecting and exploiting these differences to distinguish between non-ischemic events and ischemic events. It has been determined that once the signals are analyzed, the key differences between the two vector differences are the following: 1) the magnitude differences tend to be smaller for non-ischemic events (e.g., positional changes); 2) the angular characteristic of the vector difference over the region of the J point and the T-wave tend to be substantially constant for the ischemic case and substantially variable for non-ischemic events; 3) the fluctuations about the mean square fit to the vector angle over the same regions tend to be substantially large for non-ischemic events and relatively small for the ischemic events.

Turning now in detail to the specifics of the presently disclosed method, the ST offset that is normally used to distinguish the presents of an ischemic event can be measured as vector offset to the normal ECG. This vector offset exists for much of the QRS cycle and also for the ST and T-wave segments of the ECG. Thus, it is possible to use more data from the ECG signal for the detection of the presence of an ischemic event. The method described herein utilizes the x, y, z leads of the ECG (as described above with respect to FIGS. 1-12) which are orthogonal axes for the measurement of the ECG. These signals may be derived from the 12 lead signals by a number of transformation formulas (as described above) and the x, y and z signals can be used to generate a vector for each instant of time. This resulting vector can be represented as a Magnitude and an Azimuth and Elevation angle. The presently disclosed method utilizes a vector difference between non-ischemic signals (from an initial or base ECG from a patient's initial or from a known non-ischemic condition) and the ECG of the same patient under observation such as in a telemetry unit of a hospital. As can be appreciated, the presently disclosed technique is particularly useful for monitoring those patients which tend to have intermittent ischemic events. The reference pattern of x1, y1 and z1 signals over the QRS, T-wave interval are saved and recalled to determine the difference in the actual x2, y2 and z2 signals and the reference signal. Using a series of techniques described herein, an ischemic vector over a portion of the QRS, T-wave interval is ascertained to help distinguish between non-ischemic and ischemic conditions.

Figure 29:
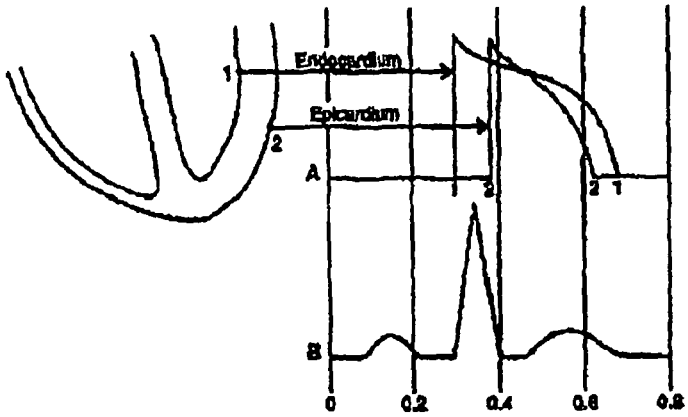
FIG. 29 shows the action potential across myocardial cells.
Figure 30:
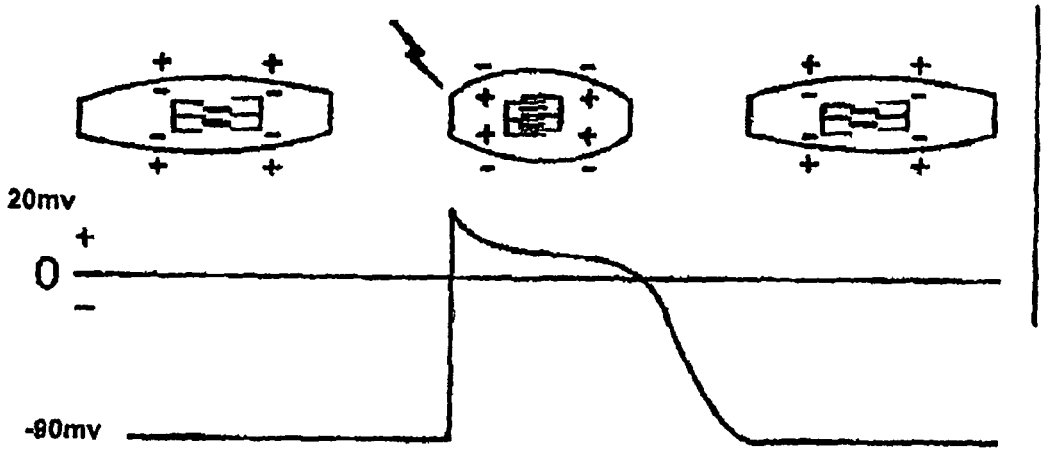
FIG. 30 shows the action potential of a single cell at three points in time.
Figure 31:
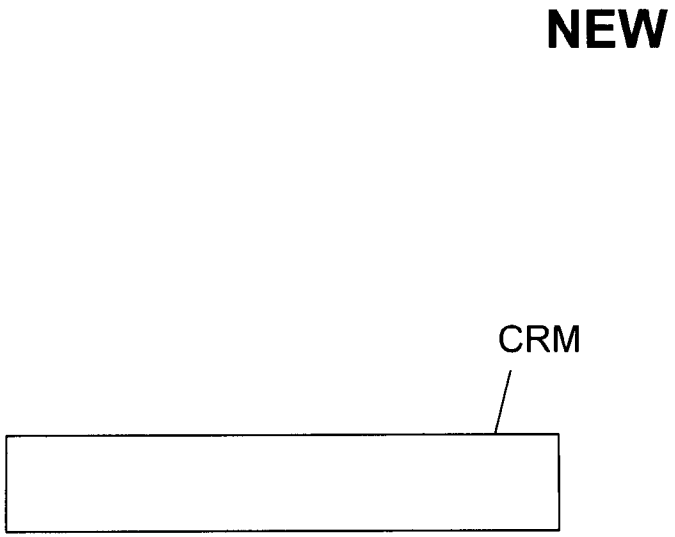
*FIG. 31 shows a computer readable medium (CRM) for storing computer programmable instructions.*

More particularly, it is possible to look at the changes in the vector between the non-ischemic heart condition and an ischemic heart over the entire cycle from the beginning of the QRS to the end of the T-wave. It has been shown that the electrical signal from individual heart cells is altered by ischemia and is manifested in the reduction of the electrical amplitude of the intercellular voltage. The QRS cycle represents the period over which myocardial cell activation begins. This reduction takes place over the time from the beginning of the activation of the cell depolarization to the cell's polarization. The cell action potential remains at this elevated level for most of the time from the beginning of the cell's activation over the QRS cycle to the end of the cell's activation over the last part of the T-wave (See FIGS. 29 and 30). Thus, it is possible to observe this effect for the entire period when the non-ischemic reference state is "subtracted" from the ischemic state. The most stable period is near the end of the QRS cycle to the peak of the T-wave. FIGS. 13-15B shows an example of a subtraction technique which can be used for this purpose using the orthogonal x, y, and z leads.

Figure 13:
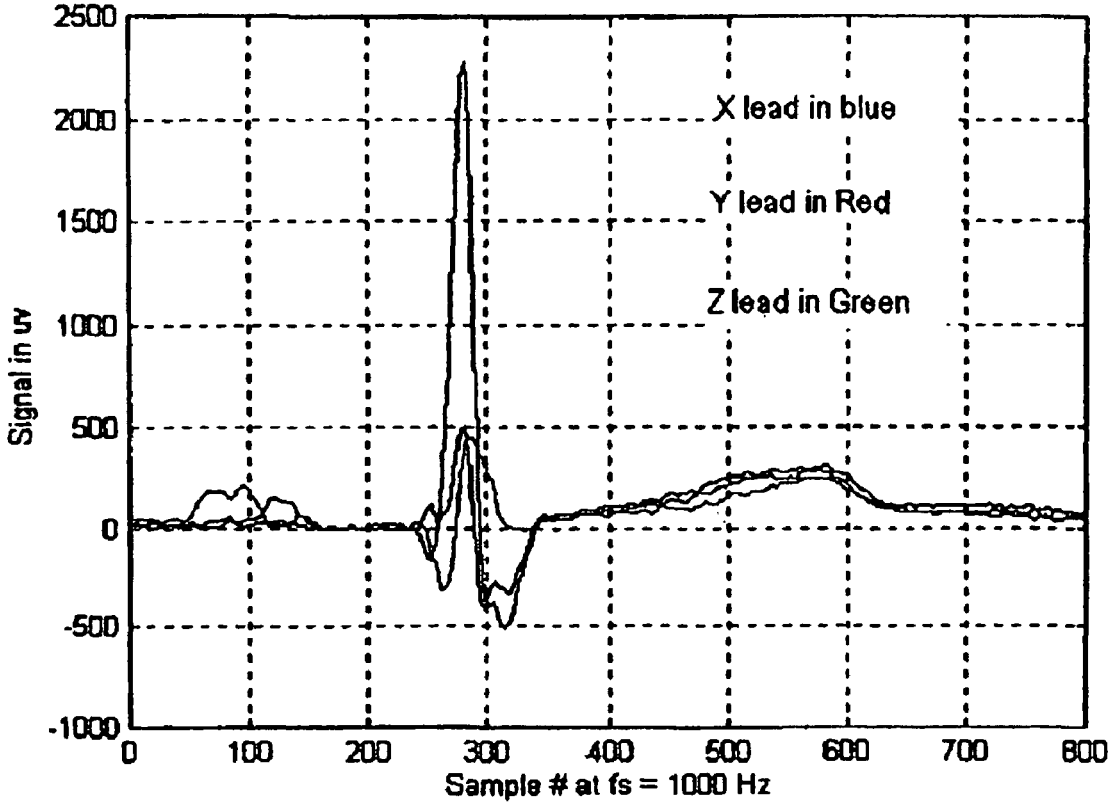
FIG. 13 is a graphical illustration of the x, y and z signal of an ECG for an entire cycle with a J-point value of about 0.08 millivolts.
Figure 14:
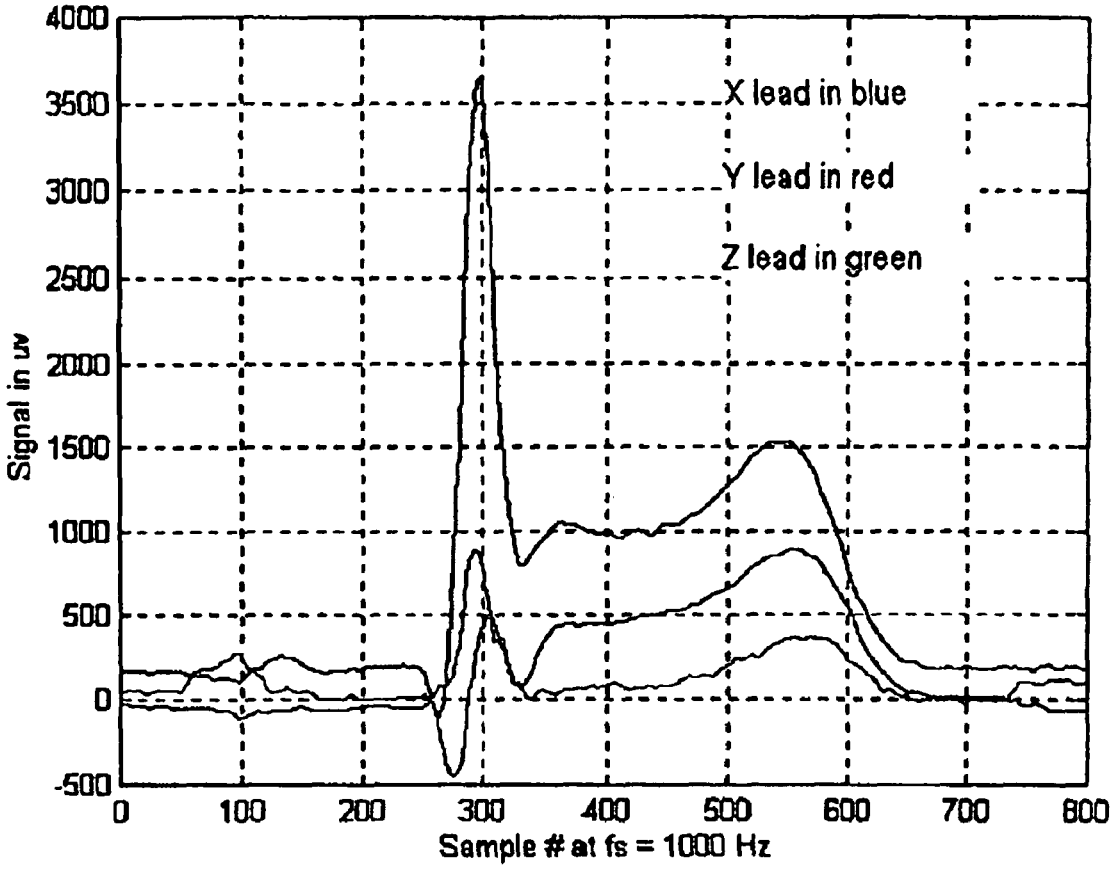
FIG. 14 is a graphical illustration of the x, y and z signal of an ECG for an entire cycle with a J-point value of about 0.99 millivolts.
Figure 15A:
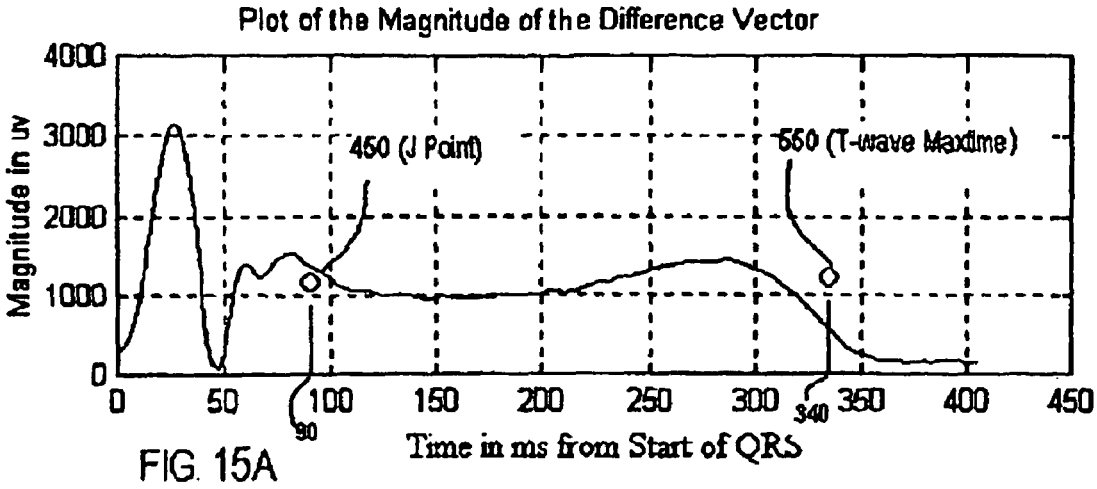
FIG. 15A is a plot of the magnitude of the vector difference between a patient's normal ECG vector signal and an ischemic vector signal.
Figure 15B:
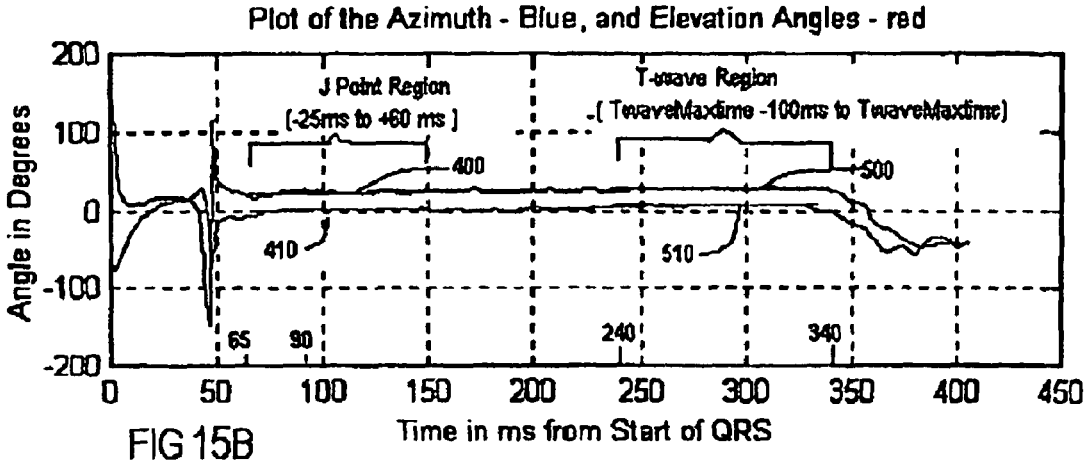
FIG. 15B is a plot of the elevation angle and azimuth angle vector difference between a patient's normal ECG vector signal and an ischemic vector signal.

FIG. 13 shows a normal level of ST at the J point, i.e., a non-ischemic condition having an ST offset at the J point of about 0.08 millivolts. FIG. 14 shows an ST magnitude of about 0.99 millivolts at the J point which is very high representing an ischemic condition. The x1, y1, z1 data from the non-ischemic condition is subtracted point for point from the x2, y2, z2 data from FIG. 14 and the results show a difference vector which is variable in amplitude but fairly constant in angle. ST offset signals are called "currents of injury" and have been described as the difference in the action potential in the normal cell and the ischemic cell (See FIGS. 29 and 30). This action potential begins at the point of excitation of the cell and ends when the cell is fully re-polarized. Thus, the action potential starts at times over the QRS interval and ends at times over the end of the T-wave. The difference in the magnitude of the vector of the components is shown in FIG. 15A. As can be appreciated, the signal is maximum during the QRS, is slightly less at the J-point and increases again at the peak of the T-wave. This may vary depending on the type of ischemic condition that exists. FIG. 15B shows the azimuth and elevation angles of the difference vector. More particularly, FIG. 15A shows the magnitude of the vector difference between the patients normal ECG and the ischemic ECG over the QRS and T wave intervals. FIG. 15B shows the Azimuth angle of the vector difference in blue and the elevation angle of the vector difference in red. Superimposed on these curves are two straight-line fits 400, 410 and 500, 510 to both the J point region and the T-wave region, respectively. These are the best estimates for the curves in region around the J point −25 ms to +60 ms, and around the T wave maximum point to a point negative 100 milliseconds (−100 ms) from the maximum.

As is evident, the ischemic cell structure is located in one region which results in a vector signal in one direction. The initial vector is very slightly different in angle which is believed to represent an initial cell excitation pattern. Since the heart myocardial cells are activated over the entire QRS cycle. The initial action potential is very high and then levels off to a slightly lower level. Even though this particular patient has a very strong ischemic signal which is most likely also easy to detect by conventional means, the strong ischemic signal also illustrates that in an ischemic condition the vector difference points in a substantially constant direction over the entire region from about 25 milliseconds before the J point to the peak of the T wave.

Figure 16A:
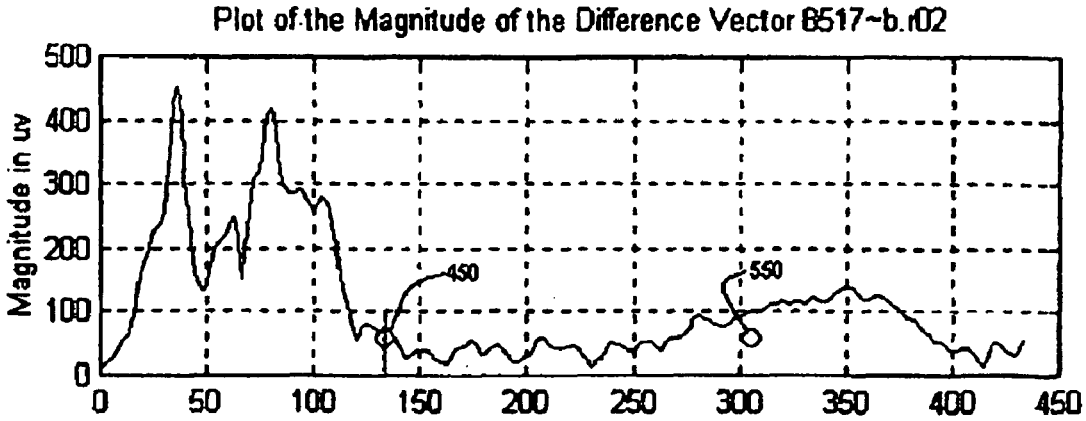
FIG. 16A is a plot of the magnitude of the vector difference of a patient in a supine position and patient in lying on his right side having circles denoting the average value over the J point and the T wave regions, respectively.
Figure 16B:
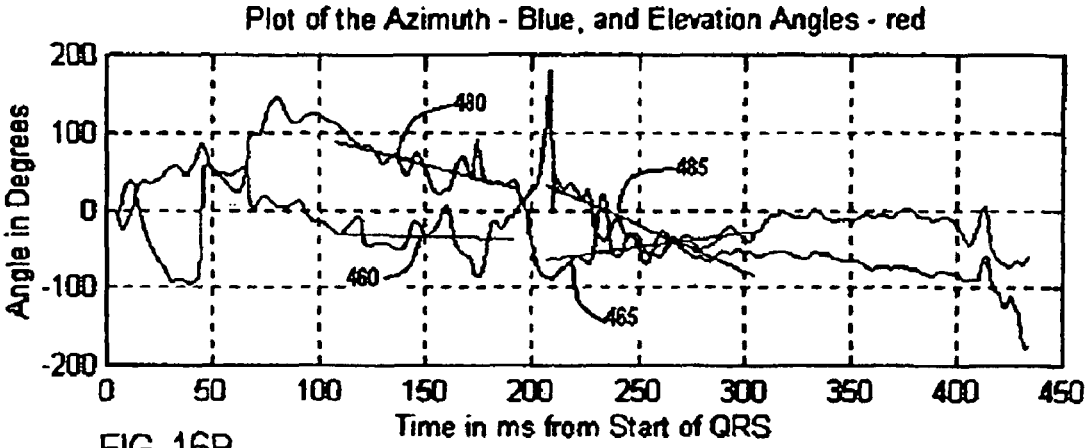
FIG. 16B is a plot of the elevation and azimuth angles of a patient in a supine position and patient in lying on his right side having a series of linear regression lines to fit the J-point region and the T wave region.

By applying this technique, the detection of an ischemic condition at the onset (i.e., initial stages of ischemia) may be detected. Moreover, this technique enables a physician, hospital staff or automatic monitor to easily distinguish between those offsets caused by the patient turning on his/her side and those offsets caused by a true ischemic condition which is often a source of false detection in the hospital monitoring situation. For example, FIGS. 16A and 16B shows a patient who changed position from supine to laying on his right side. As a result there is a change of the ECG vectors over the period of the QRS to the end of the T wave. FIG. 16A shows the magnitude of the difference vector where there is a large change in the region of the QRS and then becomes small at the J point. This is indicated by a first circle 450 and a light vertical green line. The plot also shows an increased magnitude over the T wave region. A second circle 550 shows the peak of the T wave. The center of the circles 450, 550 is located at the average level of the magnitude over the region of the straight-line fit to the angle measurements shown FIG. 16B. The straight line fit to the J point region (−25 ms before and 60 ms after) is shown as a red line 480 for the Azimuth and a green line 460 for the Elevation angle. These same colors are used for the straight line fit to the T wave region, namely 485 (Az.) and 465 (El.). It is seen that there is considerable fluctuation in these measurements and that the slope is large. It has been determined that a substantially large slope and a substantial amount of fluctuation is typical during patient positional changes. It is contemplated that a slope (or absolute magnitude of the slope) is greater than about 0.9 $\mu$v/ms and a fluctuation is greater than about 15 $\mu$v (micro-volts).

Figure 17A:
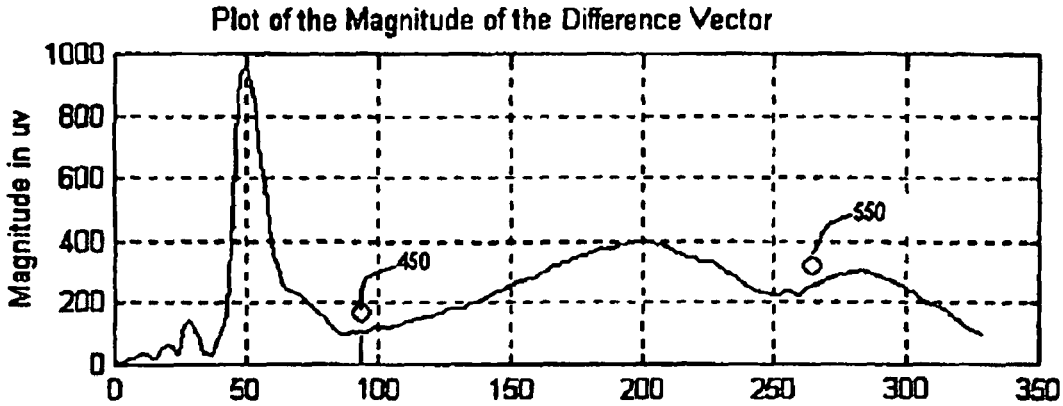
FIGS. 17A and 17B are plots of the magnitude difference and the angle vector difference between a patient without ischemia followed by an ischemic event.
Figure 17B:
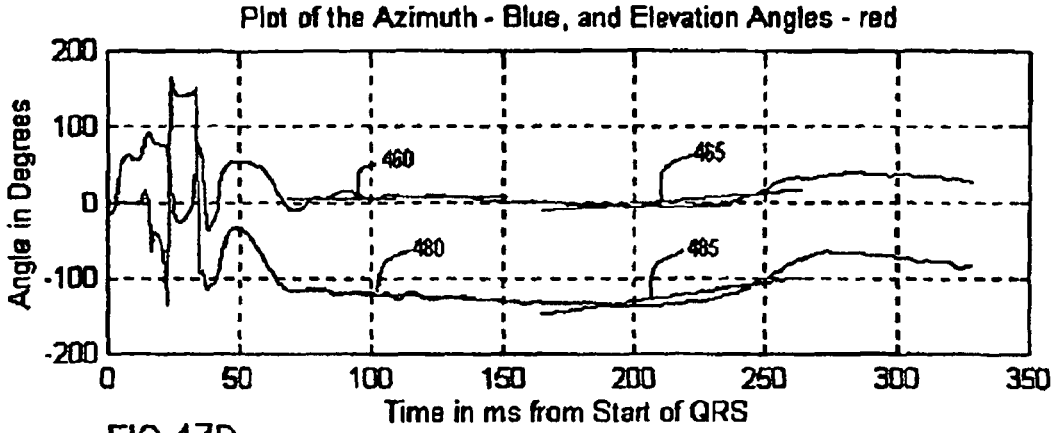

FIGS. 17A and 17B illustrate a true ischemia condition (this ischemic condition is to a much smaller extent than the file shown in FIGS. 15A and 15B). The magnitude of the difference vector is shown in FIG. 17A and is taken as the difference in the two conditions of the patient before (i.e., non-ischemic) and after the occurrence of an ischemic event. The straight line fit to the Azimuth and Elevation angles (shown in red and green, respectively) show a slope near zero and a small fluctuation of the raw data about these estimates. It has been determined that a small slope and small fluctuation in the angle difference is an indication of a true ischemic condition. It is contemplated that during an ischemic event, the slope (i.e., the absolute magnitude of the slope) is less than about 0.9 $\mu$v/ms and the fluctuation is less than about 15 $\mu$v (micro-volts).

Table 1 below illustrates a comparison of Patient 1 (non-ischemic event) and Patient 2 (true ischemic event) over 85 millisecond across the J point and over the T wave.

| | J Point Measurements over 85 ms | | | | | T-wave Measurements over 100 ms | | | | |
|---|---|---|---|---|---|---|---|---|---|---|
| Patient | ST Az Slope | ST Az Std | ST Elev Slope | ST Elev. Std | ST Avg Ampl | T-wave Az Slope | T-wave Az Std | T-wave Elev Slope | T-wave Elev. Std | T-wave Avg Ampl |
| 1 | −0.69022 | 15.171 | −0.06584 | 21.486 | 58.4 | −1.1975 | 29.69 | 0.36566 | 18.612 | 57.9 |
| 2 | −0.1712 | 2.218 | 0.02425 | 5.696 | 166.3 | 0.50109 | 10.439 | 0.28949 | 8.706 | 324.8 |

The table above shows the clear distinction between Patient 1 and 2. Patient 1 represents a non-ischemic condition (e.g., a positional change) and has high slope values and high standard deviation about the straight line fit. The ST average amplitude for Patient 1 is also small. The opposite is true for Patient 2, who is having a true ischemic event. As can be appreciated, automating these measurements of these key parameters makes it possible for automatically monitoring these patients and reliably detecting the onset of ischemic conditions. It is envisioned that this analysis may be performed for each ECG signal which enables early detection of a true ischemic condition and eliminates false ischemic events.

One of the important features of the above process is the determination of the ST offset and the J point at various timeframes. It is contemplated that the detection of the J point in an ECG is a critical parameter to enable proper measurement of the ST offset which, in turn, enables a physician to reliably determine if a patient has had an ischemic event. Typically, the detection of the J point is part of a screening process which takes place in an emergency room when a patient is admitted. These patients are frequently put on an ECG monitor to determine if the J point is elevated above a typical or normal amount (or the J point changes from a patient's initial reading by a specific amount).

One of the major issues of ascertaining a good J point measurement and the resulting ST offset is noise corruption typically associated with other electronic equipment in an emergency room setting. The presently proposed technique and method overcomes noise issues utilizing a variety of smoothing and averaging techniques which make use of the basic properties of the ECG signal to differentiate between noise and the true ECG signal.

Figure 18:
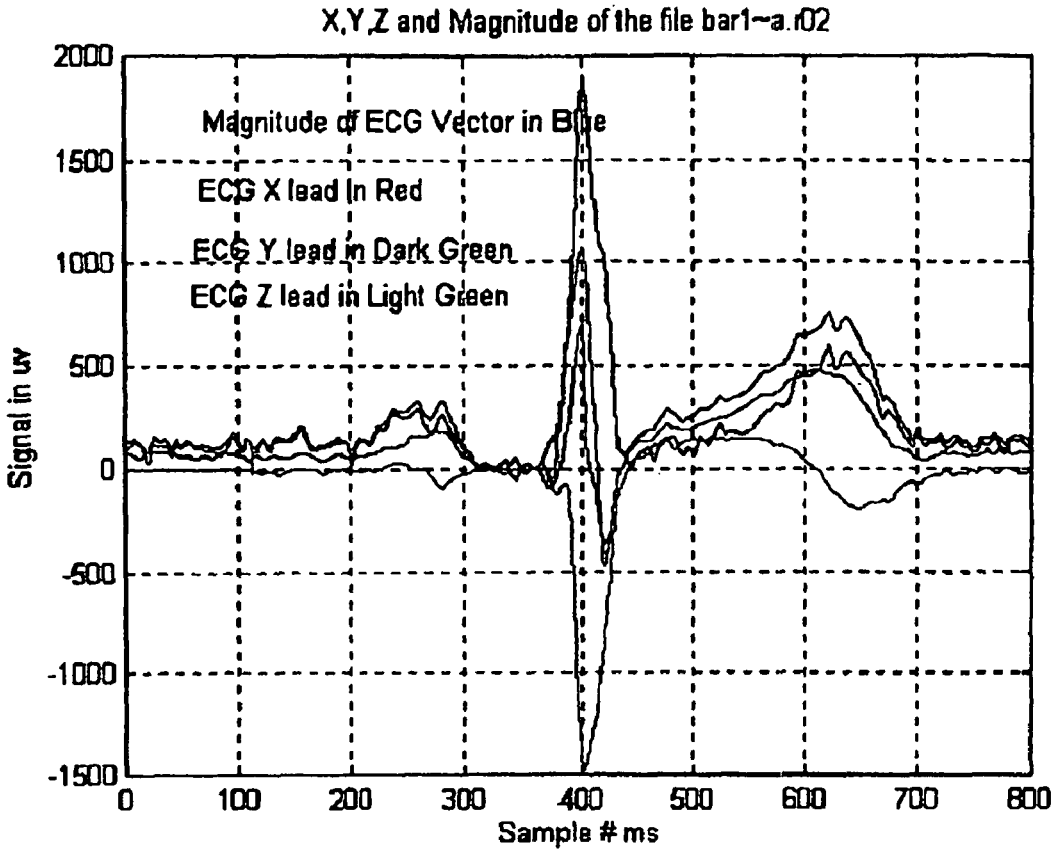
FIG. 18 is a plot showing an example of an ECG signal with an x-lead, y-lead and z-lead and showing the magnitude of the vector sum.
Figure 19:
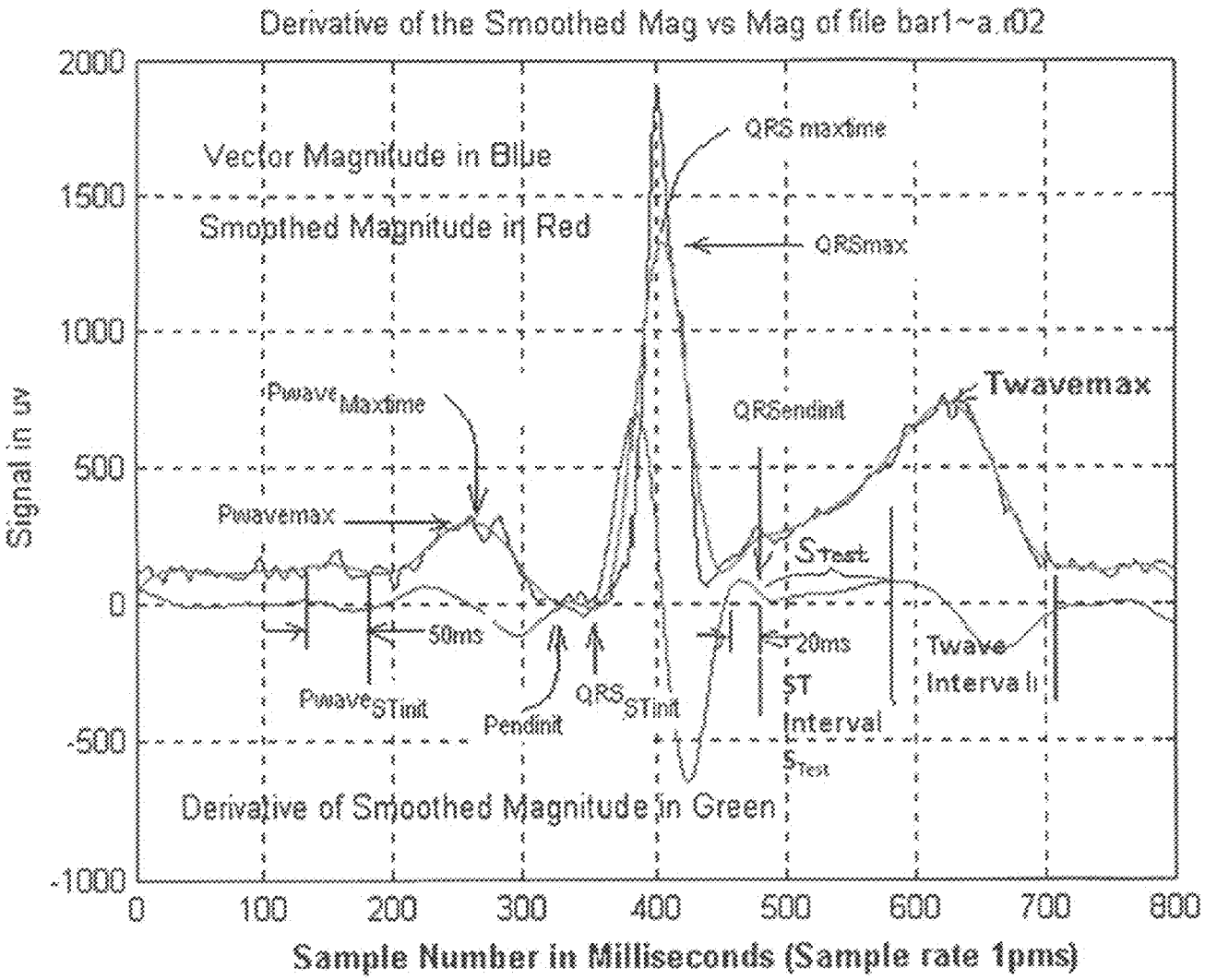
FIG. 19 is a plot showing the raw magnitude of an ECG signal, a filtered ECG signal and a derivative of the filtered signal.

As mentioned above, in order to measure ST offset, an accurate J point needs to be ascertained (as well as other critical points of the ECG as explained below). A typical ECG recording is shown in FIG. 18 and includes the x lead signal (red), the y lead signal (dark green), the z lead signal (light green) and the Magnitude of the vector (blue). The Magnitude (Mag.) of the vector is equal to the square root of the sum of the squares of the x, y and z signals:

$$\text{Magnitude}=\sqrt{(x^2+y^2+z^2)}$$

All of these signals tend to be very noisy, mostly in the regions other than the QRS interval. It is known that the critical region for a good measurement of the ST offset is immediately after the end of the QRS interval (See FIG. 12), which tends to be a relatively "noisy" region for all the leads (x, y, z) and the Magnitude.

The presently disclosed method described herein improves the noise level by passing the ECG signal through a low pass filter. Preferably, a 10-Hertz Low Pass Remez FIR filter is used to convolve the ECG signal with a balanced window function (See FIG. 19). The advantage of utilizing this type of filter is a good smoothing effect without a phase shift which results in minimum distortion of the true ECG signal by the low pass filter. Other low pass filters known in the art are also envisioned. These filtered signals provides reliable measurement points which may be used for determining the best estimate of the start and end of the P-wave, the QRS and the T-wave (See FIG. 19).

The maximum value of the QRS ($QRS_{Max}$) is found from the filtered signal since it is the largest of the signals to be found in a single cycle of the ECG inclusive of the P-wave, the QRS interval, *the ST interval* and the T-wave. Substantially at the same time, a sample point of the maximum value of the ECG *in the QRS interval* is found along with its [maximum value] *magnitude* (*QRSmax*) and time ($QRS_{MaxTime}$) (*See FIG. 19*). From [this point forward] *the time of occurrence of the maximum value of the QRS interval* (*QRSmax*) *going in a reverse direction in time towards the start of the single cycle of the ECG*, the first "zero" of the derivative of the smoothed [line] *vector signal* ($dVS_{sm}$) is determined (i.e., the first sample point where the derivative of the [smooth] *smoothed vector* signal, *or "Derivative of Smoothed Magnitude in Green"*, is zero) and that point is deemed the preliminary *or initial* start of the QRS signal ($QRS_{StInit}$). The next maximum of the ECG is then designated as the peak of the P-wave ($P_{waveMax}$) along with the P wave's time of occurrence ($P_{waveMaxTime}$). From this point, sample points are identified where the derivative of the [smooth] *smoothed vector* signal ($dVS_{sm}$) is zero. This provides additional points of departure for a more accurate measurement of the P-wave start time ($P_{waveStInit}$).

The initial point for the end of the P-wave ($P_{EndInit}$) is determined by looking forward (i.e., later in time) from the $P_{waveMaxTime}$ and finding the sample point where the derivative of the smooth curve is at its second "zero" or second minimum value.

Figure 20:
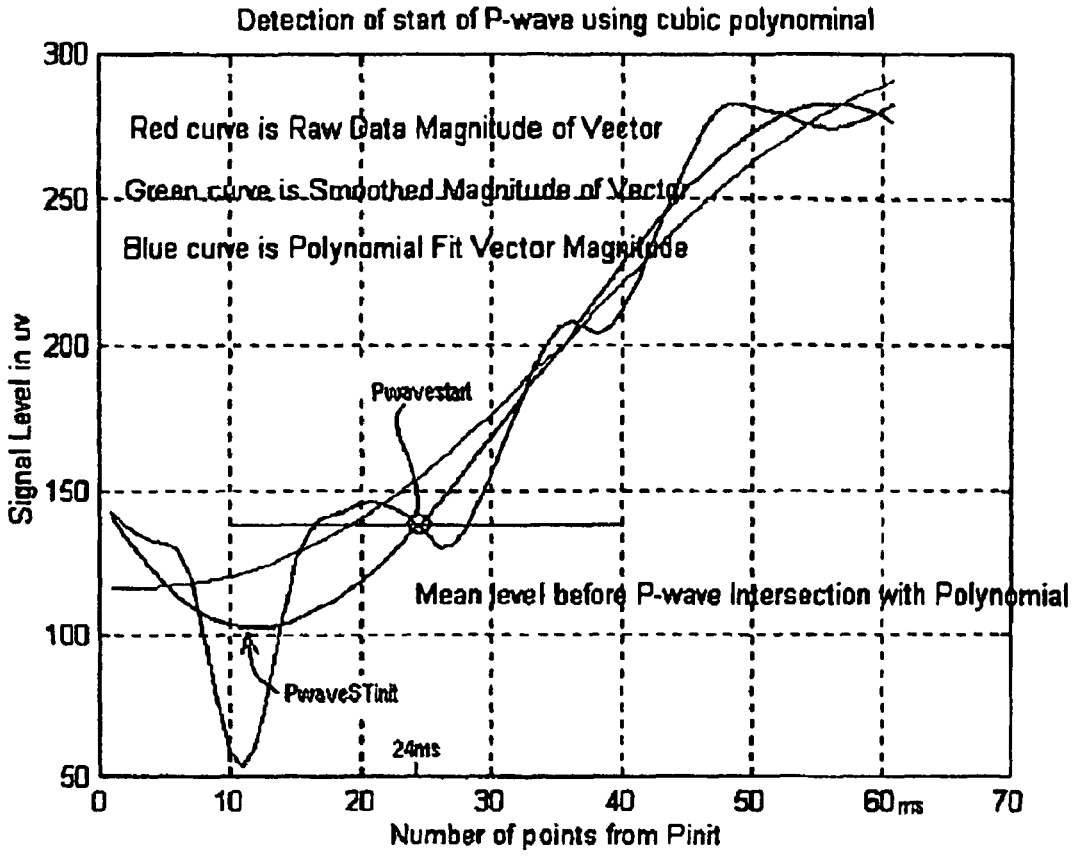
FIG. 20 is a plot showing the raw magnitude of the ECG signal, the ECG signal after a smoothing technique has been employed and a cubic polynomial fit to the raw magnitude of the ECG signal which is utilized to find a start point of the P wave of the ECG signal.

Using the $P_{waveStInit}$ value as a starting point, a polynomial function is fitted in a least squares manner to the raw Magnitude data (Mag.). By using the raw Magnitude data (Mag.), a best smooth fit is determined to this section of the data which is adequately approximated by a cubic polynomial. The results of this analysis for a typical case are shown in FIG. 20. As shown in this figure, the noise of the raw Magnitude (Mag.) curve is quite erratic whereas the cubic polynomial fit is provides a central balanced estimate of these sample points. The sample points located before the beginning of the initial point $P_{waveStInit}$, are used to determine an average value of the signal before the P-wave. For example, fifty sample points may be used to form the estimate of the prior DC level (See FIG. 19) with the polynomial curve to find a so-called "first crossing". This first crossing point is determined as the start of the P-wave ($P_{waveStart}$) which is shown in FIG. 20 as the intersection of the horizontal magenta line and the blue curve at point 24. This is the first point of intersection of the P-wave curve starting at the maximum and progressing to the start of the P-wave, which is found by the presently-disclosed smoothing process.

Another similar technique may be used to find the end of the P-wave ($P_{waveEnd}$). In this case the end of the region between the $P_{endInit}$ and the $QRS_{stInit}$ is averaged to find the reference for the end of the P-wave ($P_{QRSavg}$). At a point after the peak of the P-wave, the maximum negative slope of the smoothed Magnitude curve is determined. A line with the same slope is projected from the point of this maximum negative slope to the intersection with the $P_{QRSavg}$. This intersection point is then determined to be the end of the P-wave.

Figure 21:
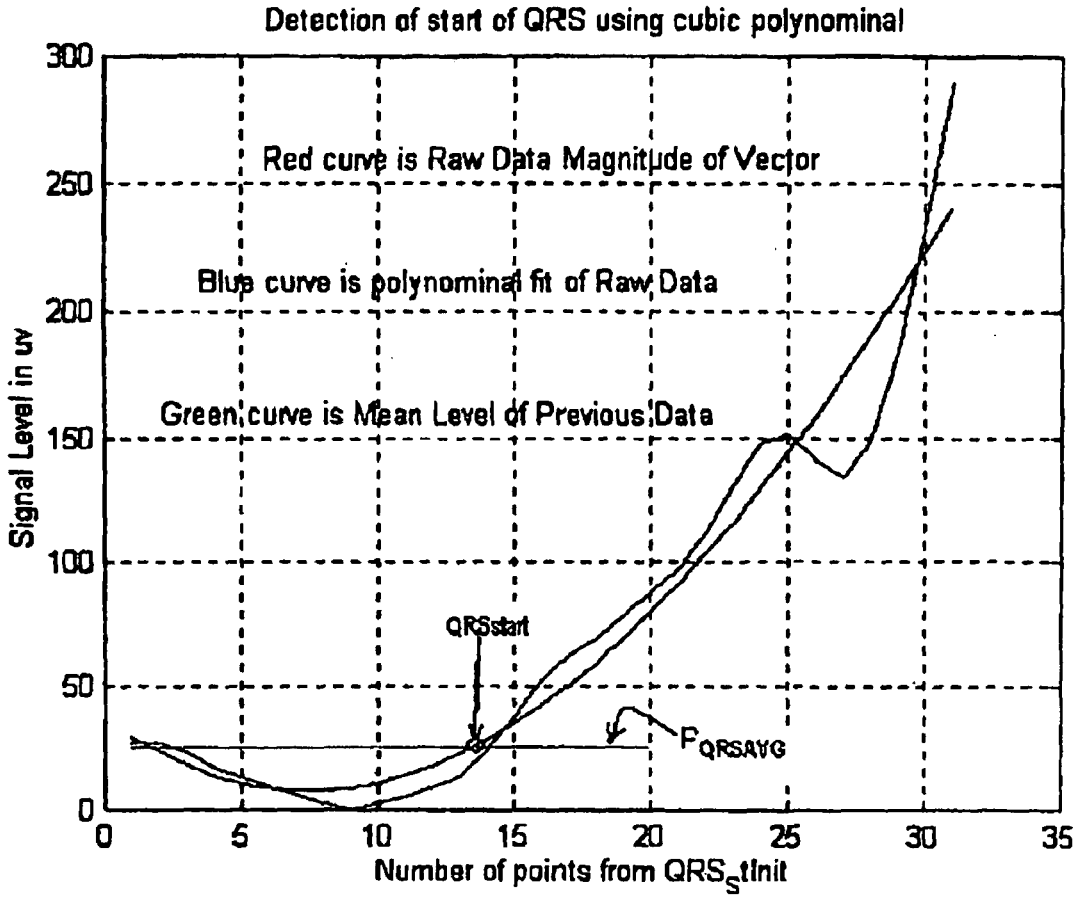
FIG. 21 is a plot showing the raw magnitude of the ECG signal and the polynomial fit to the raw magnitude of the ECG signal to find the start of the QRS interval of the ECG signal.

The start of the QRS ($QRS_{Start}$) can be found in the same manner as the P-wave start ($P_{waveStart}$). The intersection of the $P_{QRSavg}$ as a horizontal line with a polynomial fit to the raw magnitude data (Mag.) is the start point for the QRS. An example of these curves is shown in FIG. 21.

The detection of the end of the QRS interval is very important because it is the point at which the ST offset is measured, i.e., the J point. The presently disclosed method utilizes the combination of two (2) polynomial fittings: 1) the last part of the QRS interval is fitted with a cubic polynomial due to the double curvature of the data; and 2) the beginning of the ST curve of the T-wave is best fitted with a straight line (linear regression). It has been determined that the intersection of these two curves defines the J-point which is considered the end of the QRS interval and the beginning of the ST segment.

The initial sample point which is used at the onset of the analysis is found from a smooth estimate of the raw magnitude vector (Mag.) and the derivative of this smooth vector $dVS_{sm}$. The sample point after the peak of the QRS interval when the derivative of the smooth vector magnitude $dVS_{sm}$ becomes a positive value plus ~20 ms (same as sample points at 1000 Hz sample rate) may be used for the QRS interval end initiation point ($QRS_{EndInit}$). A cubic polynomial is thereafter fitted to the raw vector magnitude data (Mag.) starting at the $QRS_{EndInit}$ and going back in smaller values in steps of ~10 ms. When the magnitude of the polynomial coefficients of the so-called "$a^1$" term is greater than ~30 $\mu$v/ms (slope) or the magnitude of the so-called "$a^0$" term (constant term) minus the magnitude level at the $QRS_{EndInit}$ is greater than ~100 $\mu$v (micro-volts) the routine is stopped and the cubic polynomial coefficients from the above analysis are later used for further analysis. A straight line is fitted to the points beyond the $QRS_{EndInit}$ using initially 100 ms.

If the smoothed derivative of the smoothed data at the $QRS_{EndInit}$ plus 100 ms minus the smoothed derivative at the $QRS_{EndInit}$ point is greater than 2 $\mu$v 1 ms then the straight line estimate is recalculated over 50 ms instead of 100 ms. It is believed that this step helps rectify the unusual situation when the ST segment of the T-wave has an initial curvature (i.e., not a straight line).

The coefficients that are found using the above analysis for the ST estimate are then extended beyond the initial point $QRS_{endInit}$ to intersect the cubic curve. The point of intersection of these two curves that is furthest from the QRS interval is chosen as the final estimate of the end of the QRS interval and the beginning of the ST segment ($QRS_{End}$ or J point). This is illustrated in FIG. 22, where the intersection is found at point 30 ms.

Figure 12:
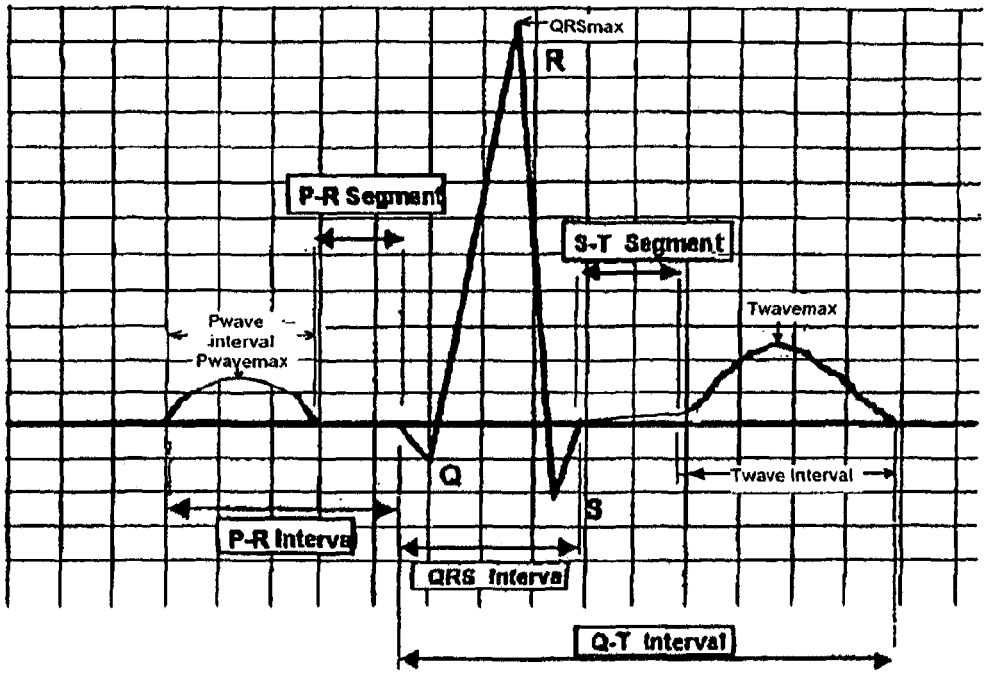
FIG. 12 is a graphical representation of an electrocardiogram showing the depolarization and repolarization of the heart muscle.

*As mentioned above and with particular respect to the T-wave, it may be desirable to utilize the methods described above to obtain an accurate and repeatable measure of the termination of the T-wave. Such a measure may be easily accomplished by applying the same principles utilized in the measurement of the beginnings and endings of the P-wave and the QRS cycle. The T-wave has many of the properties of the P-wave in that the T-wave changes slowly in time and the low passed filtered signal does not deviate very far from the true curve. For example, FIG. 12 illustrates the P wave interval and the maximum value of the P wave (Pwavemax), which can be seen as being similar to the T wave interval and the maximum value of the T wave (Twavemax). The QRS cycle and the maximum value of the QRS (QRSmax) occur between the P wave interval and the T wave interval. These characteristics of the P wave, the QRS cycle or interval, and the T wave can also be seen in FIG. 19. This allows one to get a good estimate of the peak of the T-wave from the derivative of the smooth estimate and to get a good starting point for the estimate of the end of the T-wave (TwEndInit) from the point where the smooth derivative of the vector signal ($dV_{sm}$) goes to zero. Similar to measuring the end of the QRS, two polynomials are most suited to best measure the end of the T-wave: (1) a cubic polynomial for the region of the T-wave before the end which has a double curvature; and (2) a first order polynomial to fit a straight line to the region after the end of the T-wave (a post T-wave smooth test interval (Post-Twsmoothtestinterval)). That is, the first order polynomial is fitted to the post T-wave smooth test interval (Post-Twsmoothtestinterval). The intersection of these two curves can then be used as a repeatable and accurate measure of the end of the T-wave.*

Figure 22A:
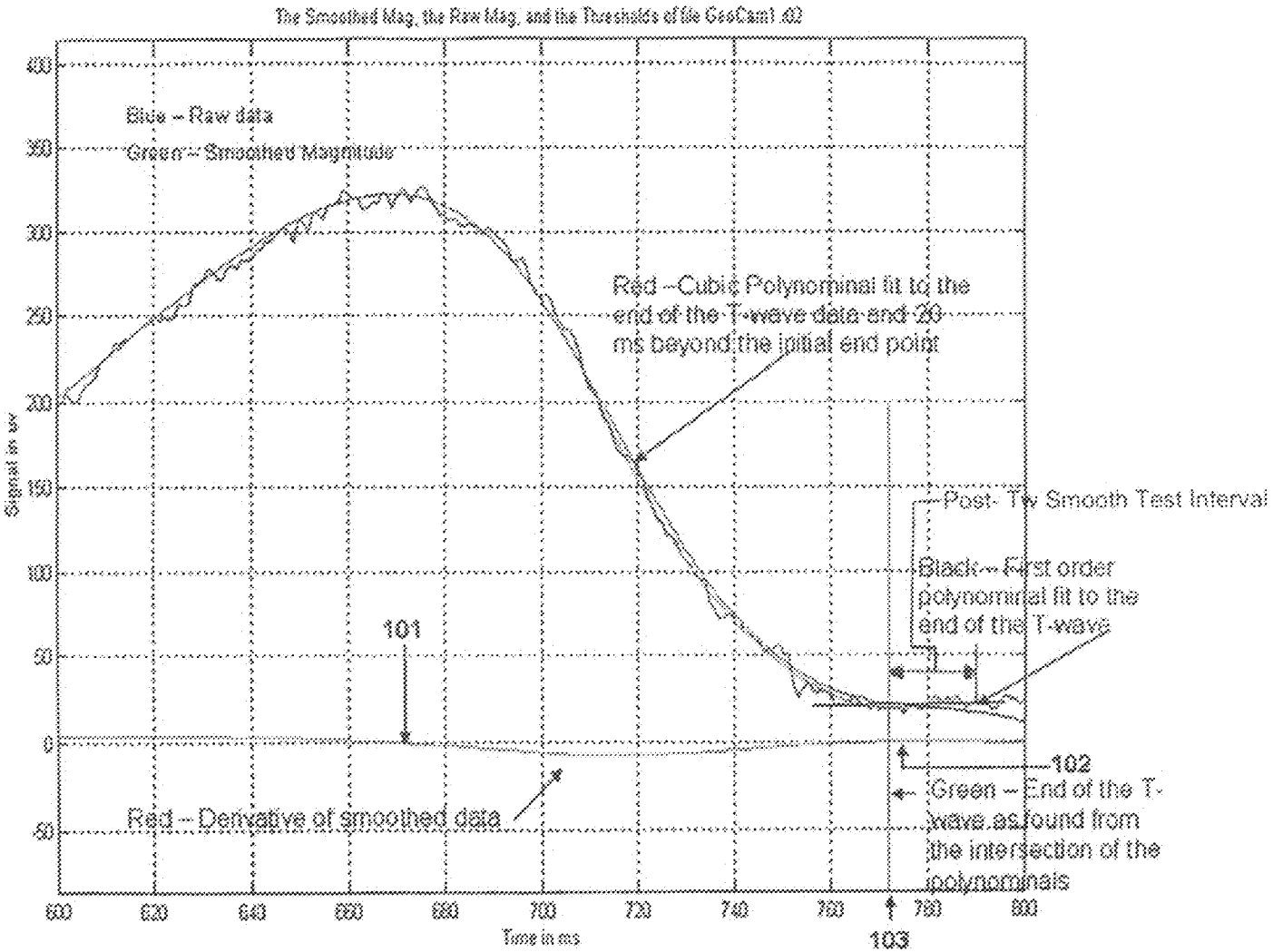
*FIG. 22A is a plot showing the raw magnitude of the ECG signal and a cubic polynomial fit to the raw magnitude of the signal to find the end of the T wave;*

*This method is illustrated in FIG. 22A which shows the T-wave of a typical ECG in which the Vector magnitude of the measured X, Y and Z signals is drawn. Also shown is the smoothed magnitude of the raw data in green. At the bottom part of the figure, the derivative of the smoothed magnitude is shown in red. The peak of the T-wave, (Twmax), is found at, or coincides with the time at which, the point 101 on the red curve at which the derivative of the smoothed magnitude curve is zero, i.e., about 670 milliseconds. At the next point 102 on the red curve at which the derivative of the smoothed magnitude ($dV_{sm}$) curve is zero, i.e., about 774 milliseconds, is found the initial or starting point for the analysis of the end of the T-wave (TwTimeEndInit). At this point 102, an initial or starting point is determined for the analysis of the end of the T-wave (TwTimeEndInit). A cubic polynomial is fitted to the last part of the T-wave curve to obtain an accurate measure of the true value of the T-wave signal without noise, i.e., the derivative of the smoothed data curve shown in red. The noisy signal or raw data curve shown in blue is seen to be a deviation from the cubic polynomial curve shown in red. The red cubic polynomial curve is extended beyond the initial end point 102, by a pre-determined time interval (e.g., about 20 milliseconds) to obtain a range of points for more accurate end point determination. Also shown is a black line which represents a first order polynomial fit to the region after the initial end point, about +/− 20 milliseconds, to provide an accurate estimate of the signal in this region. This black line is extended back through the point of initial trial 102 to find a point of intersection with the cubic polynomial curve illustrated in red. This point of intersection is shown as the abscissa of green vertical line 103, and measures the time in milliseconds of the end of the T-wave. Thus, the point 101 is the time that the derivative of the smoothed data (red curve) is zero, and is also the time of occurrence of the peak of the T-wave, i.e., Twmaxtime. Point 102 is the next zero value after the peak of the T-wave (Twmax), or the T-wave initial end point and point 103 is the time of the T-wave end (TwEnd).*

*As previously described, the beginning of the QRS is accurately measured for the same heart beat. The difference in time between the end of the T-wave (TwEnd) and the start of*

*the QRS (QRSStart) is the QT interval. The QT interval is important for determining if a patient is potentially susceptible to sudden death.*

Figure 23:
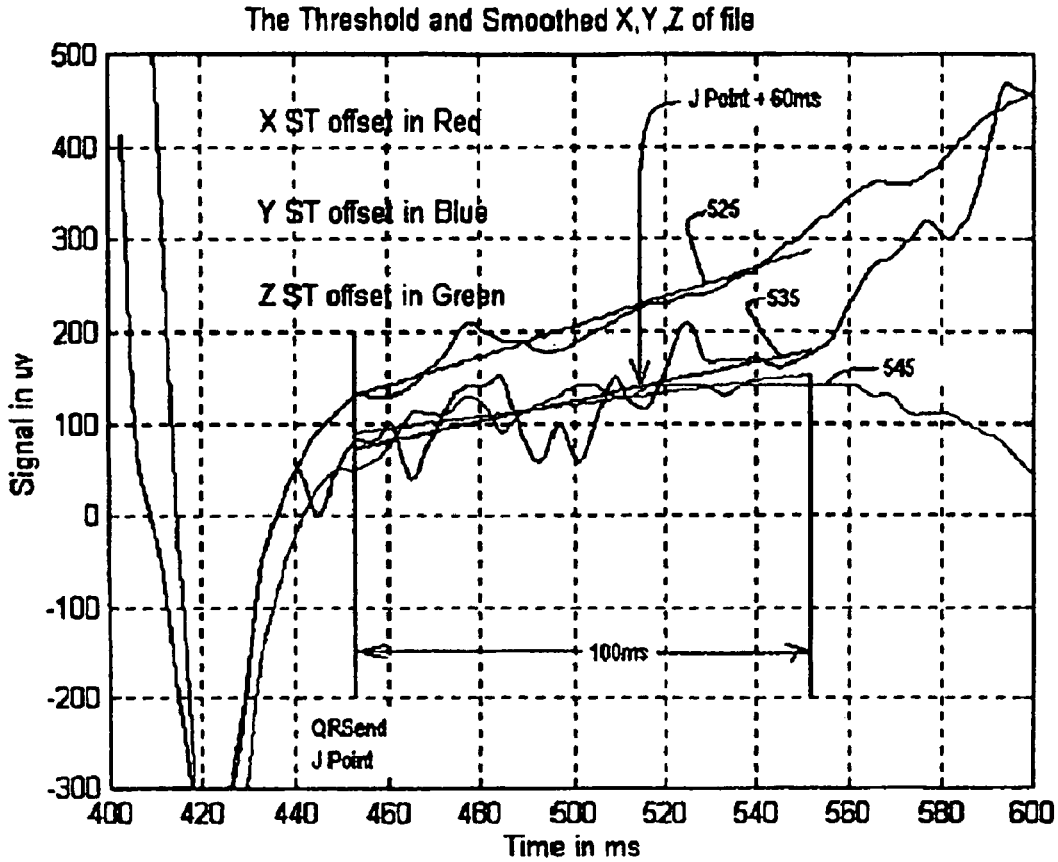
FIG. 23 is a plot showing the estimation of the ST offset in the x-lead, y-lead and z-lead utilizing a straight line smoothing technique.

Now that we know the beginning point of the ST segment is determined by the above presently disclosed method, a more accurate estimate of the ST parameters can be developed by the presently disclosed methods described below. To do this we again utilize the basic x, y and z data functions. Starting at the $QRS_{End}$ determined from above, straight line fits 525, 535 and 545 to each of these signals are calculated which determines a new best-fit estimate for all the points in this region. Thus, a new smooth estimate for the J point and also for the J point plus 60 milliseconds can be determined which are needed for the analysis herein. These new smooth estimates are illustrated in FIG. 23 wherein each of the x, y and z signals are replaced in this region by a straight line 525, 535 and 545, respectively, which forms the best least mean square estimate of the data in this region. It is clearly evident that there is a considerable variation of the raw magnitude data about these smooth estimates. From these new estimates, a vector is characterized which is represented by three components, namely, magnitude, Azimuth angle and Elevation angle. These components at the J point (453 ms) are calculated as follows:

$$\text{Magnitude}=\sqrt{(x(453)^2+y(453)^2+z(453)^2)}$$

$$\text{Azimuth Angle}=\arctan(x(453)/z(453))$$

$$\text{Elevation Angle}=\arctan(y(453)/\sqrt{(x(453)^2+z(453)^2)})$$

These components are also calculated at the J point (453 ms) plus sixty milliseconds (60 ms), i.e., 513 ms, using the same formulas.

As a result, an estimation of the ST offset can be determined for the J point and the J point plus sixty millisecond which, as mentioned above, is an essential step for accurate for heart monitoring.

Utilizing the above-identified method, a positional data set representative of the non-ischemic state may be readily determined along with a data set representative of a spontaneous ischemic event. The method results in the automatic detection of a change greater than about 100 micro-volts at the J point+60 ms in any of the 12 leads of the normal ECG or the visual detection of such a change as represented on a 3D vector cardiographic display such as FIGS. 24A and 24B. As mentioned above, the occurrence of an ischemic event is based on criteria determined from the magnitude of the vector difference and the azimuth and elevation angle consistency over the regions of the J point and the peak of the T-wave. Therefor, the maximum change will always be found by the vector magnitude whereas the 12 lead system may miss the maximum if the vector is not in the same direction as any lead.

From the present description, those skilled in the art will appreciate that various other modifications may be made without departing from the scope of the present invention. For example, while the display shows single line representations of the vectors at various time intervals over the QRS signal, in some instances it may be desirable to fill in the spaces between some or all of the vectors with a solid color, e.g., modeling, which may, in some circumstances, help in the visualization process. It is also possible to employ the technique of rendering a 3-D surface so as to show the effects of shading as the result of lighting from various sources.

Although the various figures illustrate the QRS complex portion of the ECG signal as a function time, it may be desirable to isolate or highlight other portions of the ECG signal. In fact, it is believed that other portions of the signal, if displayed in the same or similar manner as the QRS signal, may show other heart conditions which were difficult to easily recognize.

As noted in the illustrated cases, the QRS complex was sampled at 1 ms intervals. In some cases it may be desirable to sample the QRS or another portion of the signal at longer or shorter intervals, e.g., about 0.5 ms. In addition, the T-wave 42 interval is combined on the same display and sampled at 5 ms intervals since this signal does not change as rapidly. However, in some cases it may be desirable to sample the T-wave 42 at shorter or longer intervals as well.

*The methods and processes disclosed and described herein may be implemented in a processor-controlled device (e g., an electrocardiography device), or display sub-system, as software comprising one or more application programs executable within the processor commonly known to reside within processor-controlled devices (e.g., an electrocardiography device) or display sub-systems.*

*In particular, the steps of the method of determining and displaying the presence of an ischemic event, method for measuring and displaying the J-point of an electrocardiogram signal and method for determining and displaying from an electrocardiogram signal at least one of the beginning and the end of the P-wave, the P-wave duration, the start of the QRS interval, the end of the T-wave, the QT interval, the PR interval and the QRS duration are effected by instructions in the software that are executed by the processor. The programmable instructions may be formed as one or more code modules, each for performing one or more particular tasks.*

What is claimed is:

[1. A method of determining an ischemic event, said method comprising the steps of:

monitoring and storing an initial electrocardiogram vector signal (x1, y1, z1) of a known non-ischemic condition over the QRS, ST and T wave intervals;

calculating and storing a J-point of the vector signal (x1, y1, z1) and a maximum magnitude of a signal level over said T wave interval;

monitoring a subsequent electrocardiogram vector signal (x2, y2, z2) over the QRS, ST and T wave intervals;

measuring the magnitude (Mag.) of the vector difference between a subsequent vector signal (x2, y2, z2) and the initial vector signal (x1, y1, z1);

measuring the angle (Ang.) difference between a subsequent vector (x2, y2, z2) and said initial vector signal (x1, y1, z1);

regressing a line from points about 25 milliseconds prior to the J point and about 60 milliseconds after the J-point and determining the slope of the regression line and the deviation of the angle difference of said regression line;

regressing a line from points about 100 milliseconds prior to said maximum magnitude of the signal level over said T wave interval and determining the slope of the regressing line and the deviation of the angle difference of said regression line; and comparing said slope and deviation of said lines from said J point and said T wave interval to a set of known values to determine the presence of an ischemic event.]

[2. A method according to claim 1 wherein the step of measuring and storing the magnitude (Mag.) of the vector difference includes the steps of:

accessing the stored initial electrocardiogram vector signal (x1, y1, z1) of a known non-ischemic condition over the QRS, ST and T wave intervals;

measuring said subsequent electrocardiogram vector signal (x2, y2, z2) over the QRS, ST and T wave intervals;

calculating the change (Δ) in the vector signal over the QRS, ST and T wave intervals by the following formula:

$$\Delta x = x2 - x1$$

$$\Delta y = y2 - y1$$

$$\Delta z = z2 - z1;$$

and calculating the magnitude of the vector difference ($Mag_{vd}$) over the QRS, ST and T wave intervals by the following formula:

$$Mag_{vd} = \sqrt{(\Delta x^2 + \Delta y^2 + \Delta z^2)}]$$

[3. A method according to claim 1 wherein the step of measuring and storing the angle of the vector difference (Ang.) includes the steps of:

accessing the stored initial electrocardiogram vector signal (x, y, z) of a known non-ischemic condition over the QRS, ST and T wave intervals;

measuring said subsequent electrocardiogram vector signal (x, y, z) over the QRS, ST and T wave intervals;

calculating the change (Δ) in the vector signal over the QRS, ST and T wave intervals by the following formula:

$$\Delta x = x2 - x1$$

$$\Delta y = y2 - y1$$

$$\Delta z = z2 - z1,$$

calculating an Azimuth angle (Az. Ang.) of said angle vector difference over the QRS, ST and T wave intervals by the following formula:

$$\text{Az. Ang.} = \arctan(\Delta z/\Delta x); \text{ and}$$

calculating an Elevation angle (El. Ang.) of said angle vector difference over the QRS, ST and T wave intervals by the following formula:

$$\text{El. Ang.} = \arctan(\Delta y/\sqrt{(\Delta x^2 + \Delta z^2)}).]$$

[4. A method according to claim 1 wherein the step of calculating said J point includes the steps of:

calculating the magnitude of the initial vector signal ($Mag_{vs}$) over the QRS, ST and T wave intervals by the following formula:

$$Mag_{vs} = \sqrt{(x^2 + y^2 + z^2)};$$

filtering said magnitude of the vector signal ($Mag_{vs}$) over the QRS, ST and T wave intervals through a low pass filter to establish a smooth vector signal ($VS_{sm}$) and a maximum value and time of the QRS interval ($QRS_{max}$ and $QRS_{maxtime}$);

differentiating said smooth vector signal ($VS_{sm}$) from said magnitude of the vector signal ($Mag_{vs}$) over the QRS, ST and T wave intervals and establishing a derivative vector signal ($dVS_{sm}$);

calculating a set of initial parameters from the QRS interval including: the magnitude of the maximum QRS signal ($QRS_{max}1$); the maximum of the QRS time interval ($QRS_{maxtime}$); and the end point of the QRS signal ($QRS_{EndInit}$);

calculating a set of initial parameters from the T wave interval including: the magnitude of the maximum T wave signal ($Twave_{max}$); and the maximum of the T wave time interval ($Twave_{maxtime}$); and calculating an initial estimate of the end of the QRS interval ($QRS_{EndInit}$);

fitting the vector signal along a cubic polynomial curve;

calculating the change in the derived vector signal ($dVS_{sm}$) over a prescribed time period to establish a smooth test interval ($S_{Test}$);

fitting a first order polynomial curve to the initial vector signal ($Mag_{vs}$) starting at the end of the QRS interval (QRS_EndInit) to a point which is equal to the end of the QRS interval (QRS_EndInit) plus the smooth test interval ($S_{Test}$); and calculating the intersection of the cubic polynomial curve and the first order polynomial curve and selecting a point of intersection that is furthest from the time of the maximum QRS value ($QRS_{maxtime}$) to establish the J point.]

[5. A method according to claim 1 wherein after said step of monitoring and storing an initial electrocardiogram vector signal (x, y, z) of a known non-ischemic condition over the QRS, ST and T wave intervals, the method includes the step of estimating a magnitude and angle of said ST interval.]

*6. A method of determining and displaying the presence of an ischemic event implemented in a processor of a medical device, said method comprising the steps of:*

*monitoring and storing in said processor an initial electrocardiogram vector signal (x1, y1, z1), comprising a first sequence of samples, of a known non-ischemic condition over the QRS, ST, and T wave intervals;*

*calculating and storing in said processor a magnitude (Mag.) and angle (Ang.) for each sample of the first sequence of samples of the initial vector signal (x1, y1, z1) including a J-point and a maximum magnitude over each of the QRS, ST and T wave intervals;*

*monitoring a subsequent electrocardiogram vector signal (x2, y2, z2), comprising a second sequence of samples including a J-point, and calculating a magnitude (Mag.) and angle (Ang.) for each sample of the second sequence of samples over the QRS, ST and T wave intervals;*

*shifting the first sequence of samples or the second sequence of samples, where necessary, in order to substantially align the initial vector signal (x1, y1, z1) and the subsequent vector signal (x2, y2, z2) in time;*

*calculating a difference vector (Vd) as a difference in magnitude (Mag.) and a difference in angle (Ang.) between each sequenced sample of the first sequence of samples and each corresponding sequenced sample of the second sequence of samples over the QRS, ST, and T wave intervals;*

*regressing a line (A1) and a line (E1) from scalar representatives of an Azimuth angle (Az. Ang.) part and Elevation angle (El. Ang.) part of the sequenced angle (Ang.) samples of the difference vector (Vd) from about 25 milliseconds prior to the J point to about 60 milliseconds after the J-point;*

*determining slopes of said regression line (A1) and said regression line (E1);*

*determining a standard deviation of an angle difference between the samples comprising said regression line (A1) and the corresponding azimuth angle (Az. An.) samples of the difference vector (Vd), and a standard deviation of an angle difference between the samples comprising said regression line (E1) and the corresponding elevation angle (El. An.) samples of the difference vector (Vd); and*

*comparing said slopes and said standard deviations of said angle differences of said regression line (A1) and said regression line (E1) to a set of known slope values and known standard deviation values to determine the presence of an ischemic event.*

7. A method according to claim 6 wherein the step of calculating the difference vector (Vd), corresponding to the angle (Ang.) difference includes the steps of:

calculating changes (Δ) between each sample of the second sequence of samples and each corresponding sample of the first sequence of samples over the respective QRS, ST and T wave intervals by the following formulas:

$$\Delta x = x2 - x1;$$

$$\Delta y = y2 - y1;$$

$$\Delta z = z2 - z1;$$

and using the Δx, Δy and Δz for each sample change, calculating the Azimuth angle (Az. Ang.) part of said angle-(Ang.) difference by the following formula:

$$Az.\ Ang. = \arctan(\Delta z/\Delta x);\ \text{and}$$

calculating the Elevation angle (El. Ang.) part of said angle-(Ang.) difference by the following formula:

$$El.\ Ang. = \arctan\ (\Delta y/((\Delta x^2)+(\Delta z^2))^{1/2}),$$

wherein said angle (Ang.) difference for each sample of the difference vector (Vd) comprises an AZ. Ang. and an El. Ang.

8. A method according to claim 6, further comprising, after said step of monitoring and storing the first sequence of samples and, said step of monitoring the second sequence of samples, a step of utilizing the magnitude (Mag.) and angle (Ang.) at the J point of the second sequence of samples as an estimated offset of the ST interval.

9. A method according to claim 8, wherein the method further comprises the step of:

displaying, on a display in operative communication with said processor, said J point of the second sequence of samples.

10. A method according to claim 6, further comprising a step of:

displaying, on a display in operative communication with said processor, said comparison of said slopes and said standard deviations to visually communicate said determination of said presence of said ischemic event.

11. A method according to claim 6, further comprising steps of:

regressing a line (A2) and a line (E2) from scalar representations of Azimuth angle (Az. Ang.) and Elevation angle (El. An.) parts of the sequenced angle (Ang.) samples of the difference vectors (Vd), from about 100 milliseconds prior to said maximum magnitude of the signal level over said T wave interval;

determining slopes of said regression line (A2) and said regression line (E2);

determining a standard deviation of an angle difference between samples comprising said regression line (A2) and the corresponding azimuth angle (Az. An.) samples of the difference vector (Vd), and a standard deviation of an angle difference between the samples comprising said regression line (E2) and the corresponding elevation angle (El. An.) samples of the difference vector (Vd); and comparing said slopes and said standard deviations of said angle differences of said regression line (A2) and said regression line (E2) to a set of known slope values and known standard deviation values to determine the presence of an ischemic event.

12. A method according to claim 6, wherein the initial electrocardiogram vector signal (x1, y1, z1) is (0, 0, 0).

13. A method for measuring and displaying a J-point of an electrocardiogram signal implemented in a processor of a medical device, the method comprising the steps of:

monitoring and storing an electrocardiogram vector signal (x, y, z) comprising a sequence of samples over QRS, ST and T wave intervals of the electrocardiogram signal;

calculating and storing a corresponding sequence of magnitudes ($Mag_{vs}$), where each magnitude ($Mag_{vs}$) corresponds respectively to each of the sequence of samples, a J-point and a maximum magnitude of a signal level of the electrocardiogram vector signal (x, y, z) over the QRS, ST and T wave intervals;

filtering said sequence of magnitudes ($Mag_{vs}$) through a low pass filter to establish a smooth signal ($VS_{sm}$), a maximum value of the smooth signal ($VS_{sm}$) in the QRS interval ($QRSVS_{max}$) and a time of occurrence of the maximum value of the smooth signal ($VS_{sm}$) in the QRS interval ($QRSVS_{maxtime}$);

differentiating with respect to time the smooth signal ($VS_{sm}$) to establish a derivative of the smooth signal ($dVS_{sm}$) with respect to time;

calculating a set of initial parameters from the smooth signal ($VS_{sm}$) in the QRS interval including:

an initial estimated time of the start of the QRS interval ($QRS_{startInit}$) by finding the time before the time of occurrence of the maximum value of the smooth signal ($Vs_{sm}$) in the QRS interval ($QRSVS_{maxtime}$) that the derivative of the smooth signal ($dVS_{sm}$) changes polarity from negative to positive; and an initial estimated time of occurrence of the end point of the QRS interval ($QRS_{endInit}$) by finding the time of occurrence after the time of occurrence of the maximum smooth signal ($VS_{sm}$) in the QRS interval ($QRSVS_{maxtime}$) at which the derivative of the smooth signal ($dVS_{sm}$) changes polarity from negative to positive; and displaying, on a display in operative communication with said processor, said initial estimated time of the end point of the QRS interval ($QRS_{endInit}$).

14. A method according to claim 13, further comprising the steps of:

fitting said sequence of magnitudes ($Mag_{vs}$) along a cubic polynomial curve extending from a sample midway between the time of occurrence of the maximum value of the smooth signal in the QRS interval ($QRSVS_{maxtime}$) and the initial estimated time of occurrence of the end point of the QRS interval ($QRS_{endInit}$), to a sample at the initial estimated time of occurrence of the end point of the QRS interval ($QRS_{endInit}$);

calculating a change in the derivative of the smooth signal ($dVS_{sm}$) for a period extending in a range of 50 to 100 ms, beyond the initial estimated time of occurrence of the end point of the QRS interval ($QRS_{endInit}$) to establish a smooth test interval ($S_{Test}$);

fitting a first order polynomial curve to said sequence of magnitudes ($Mag_{vs}$) starting at the initial estimated time of occurrence of the end point of the QRS interval (QRSendinit) and an end point of the smooth test interval ($S_{Test}$);

calculating points of intersection of the cubic polynomial curve and the first order polynomial curve; and selecting a point of intersection that is furthest in time from the time of occurrence of the maximum value of the smooth signal ($VS_{sm}$) in the QRS interval ($QRSVS_{maxtime}$), which intersection point is a true end of the QRS interval ($QRS_{trueend}$), and identifying the true end as the J point.

15. A method according to claim 14, further comprising the step of displaying, on a display in operative communication with said processor, said J point.

16. A method for determining and displaying from an electrocardiogram signal at least one of a beginning and an end of the P-wave interval, a duration of the P-wave interval, a start of the QRS interval, an end of the T-wave interval, a QT interval, a PR interval, and a duration of the QRS interval, the method implemented in a processor within a medical device and comprising the steps of:

monitoring and storing an electrocardiogram vector signal (x, y, z), comprising a sequence of samples, from the electrocardiogram signal over an entire heart beat cycle including the P-wave, QRS, and T-wave intervals;

calculating a magnitude for each of the samples of the electrocardiogram vector signal (x, y, z) over the P-wave, QRS and T-wave intervals, to realize a corresponding sequence of magnitude values comprising a magnitude signal (Mag), by the following formula:

$$Mag=((x^2)+(y^2)+(z^2))^{1/2}$$

filtering the calculated magnitude signal (Mag) over the P-wave, QRS, and T-wave intervals to establish:

a smooth signal ($VS_{sm}$);

a time of occurrence of a maximum value of the smooth signal ($VS_{sm}$) during the P-wave interval (Pwmaxtime);

a magnitude of the maximum value of the smooth signal ($VS_{sm}$) during the P-wave interval (Pwmax);

a time of occurrence of the maximum value of the smooth signal ($VS_{sm}$) during the QRS interval (QRSVSmaxtime);

a magnitude of the maximum value of the smooth signal ($VS_{sm}$) during the QRS interval (QRSVSmaxtime);

a time of occurrence of the maximum value of the smooth signal ($VS_{sm}$) during the T-wave interval (Twmax); and a magnitude of the maximum value of the smooth signal ($VS_{sm}$) during the T-wave interval (Twmaxtime);

establishing a derivative vector signal ($dVS_{sm}$) with respect to time of the smooth signal ($VS_{sm}$);

calculating from the smooth signal ($VS_{sm}$) over the P-wave interval an initial estimated time of the start of the P-wave interval (PwStInit) at a point where the derivative signal ($dVS_{sm}$) changes from negative to positive, before the time of occurrence of the maximum value of the smooth signal ($VS_{sm}$) during the P-wave interval (Pwmaxtime) and the initial estimated time of the end point of the P-wave interval (PwEndInit) where the derivative signal changes from negative to positive after the time of occurrence of the maximum value of the smooth signal ($VS_{sm}$) during the P-wave interval (Pwmaxtime); and displaying, on a display in operative communication with said processor, the magnitude of the maximum value of the smooth signal ($VS_{sm}$) during the P-wave interval (Pwmax), the time of occurrence of the maximum value of the smooth signal ($VS_{sm}$) during the P-wave interval (Pwmaxtime), the initial estimated time of the start of the P-wave interval (PwTimeStInit), and the initial estimated time of the end of the P-wave interval (PwTimeEndInit).

17. A method according to claim 16, further comprising the steps of:

calculating from the smooth signal ($VS_{sm}$) over the QRS interval an initial estimated time of the start of the QRS interval (QRSStInit) at a point where the derivative signal ($dVS_{sm}$) has a first zero value, before the time of occurrence of the maximum value of the smooth vector signal ($VS_{sm}$) of the electrocardiogram vector signal (x, y, z) during the QRS interval (QRSVSmaxtime).

18. A method according to claim 17, further comprising the steps of:

calculating from the smooth signal ($V_{sm}$) over the T-wave interval an initial estimated time of occurrence of the end point of the T-wave interval (TwTimeEndInit) at a point in time where the derivative of the smooth signal ($dVS_{sm}$) changes from negative to positive after the time of occurrence of the maximum smooth signal ($VS_{sm}$) during the T-wave interval (Twmaxtime).

19. A method according to claim 18, further comprising the steps:

fitting a first cubic polynomial curve to the smooth signal ($VS_{sm}$), from the initial estimated time of the start of the P-wave interval (PwaveTimeStInit) to the time of occurrence of the maximum smooth signal ($VS_{sm}$) during the P-wave interval (Pwmaxtime); and finding a point (1) within the first cubic polynomial curve displaying a magnitude equivalent to an average of the signal magnitude ($Mag_{vs}$) averaged over a region that starts 20 ms before the initial estimated time of the start of the P-wave interval (PwaveTimeStInit) and ends at the initial estimated time of the start of the P-wave interval (PwaveTimeStInit), wherein said point (1) comprises a refined estimate of the start of the P-wave interval (PwStart).

20. A method according to claim 19, further comprising the steps:

fitting a second cubic polynomial curve to the smooth signal ($VS_{sm}$), from the time of occurrence of the maximum smooth signal ($VS_{sm}$) during the P-wave interval (Pwmaxtime) to the initial estimated time of the end of the P-wave interval (PwaveTimeEndInit); and finding a point (2) within the second cubic polynomial curve equal to a magnitude equivalent to an average of the magnitude signal ($Mag_{vs}$) averaged over a region that begins at the initial estimated time of the end of the P-wave interval (PwaveTimeEndInit) and ends at the initial start time of the QRS interval (QRStime StartInit), wherein said point (2) comprises a refined estimate of the time of occurrence of the end of the P-wave interval (PwEnd).

21. A method according to claim 20, further comprising the steps:

fitting a third cubic polynomial curve to the smooth signal ($VS_{sm}$), from the initial start time of the QRS interval (QRStimeStartInit) to the time of occurrence of the maximum value of the smooth signal ($VS_{sm}$) during the QRS interval (QRSVSmaxtime); and finding a point (3) within the third cubic polynomial curve equal to a magnitude equivalent to an average of the magnitude signal ($Mag_{vs}$) averaged over a region that starts from the initial estimated time of the end of the P-wave interval (PwTimeEndInit) and extends to the initial estimated time of the start of the QRS interval (QRSStInit), wherein said point (3) comprises a refined estimate of the start time of the QRS interval (QRSStart).

22. A method according to claim 21, further comprising the step of:

*calculating the PR interval, using the following formula:*

$$PR\ interval = QRSStart - PwStart.$$

*23. A method according to claim 21, further comprising the step of:*

*fitting a fourth cubic polynomial curve to a portion of the smooth signal ($VS_{sm}$) that extends from a point midway between the time of occurrence of the maximum smooth signal ($VS_{sm}$) in the Twave interval (Twmaxtime) and the initial estimated time of occurrence of the end point of the Twave interval (TwTimeEndInit).*

*24. A method according to claim 23, further comprising the steps of:*

*calculating a change in the derivative of the smooth signal ($dVS_{sm}$) over a prescribed time period after the initial estimated time of occurrence of the end point of the T wave interval (TwTimeEndInit) when the derivative of the smooth signal ($dVS_{sm}$) exhibits a substantially constant magnitude to establish a post T wave smooth test interval (Twtime endInit+Post Twsmoothtest);*

*fitting a first order polynomial curve to a portion of the smooth signal ($VS_{sm}$) that starts at the initial estimated time of occurrence of the end point of the T wave interval (TwTimeEndInit) and extends through the initial estimated time of occurrence of the end point of the T wave interval (TwTimeEndInit) for about another 20 ms;*

*calculating points of intersection of the fourth cubic polynomial curve and the first order polynomial curve; and*

*selecting one of the points of intersection that is furthest in time from the time occurrence of the maximum smooth signal ($VS_{sm}$) during the Twave interval (Twavemaxtime), which said one of the points comprises the time of occurrence of the end point of the T wave interval (TwaveEnd).*

*25. A method according to claim 24, further comprising the step of displaying, on a display in operative communication with said processor, said time of occurrence of the end point of the T wave interval (TwaveEnd).*

* * * * *